(12) United States Patent
Sidi et al.

(10) Patent No.: US 10,113,170 B2
(45) Date of Patent: Oct. 30, 2018

(54) PREVENTING AND TREATING INFLAMMATORY SKIN DISEASES

(71) Applicant: TEL HASHOMER MEDICAL RESEARCH INFRASTRUCTURE AND SERVICES LTD., Ramat Gan (IL)

(72) Inventors: Yechezkel Sidi, Petah Tikva (IL); Dror Avni, Zichron Yaakov (IL); Gali Lerman, Alpharetta, GA (US)

(73) Assignee: TEL HASHOMER MEDICAL RESEARCH INFRASTRUCTURE AND SERVICES LTD., Ramat Gan (IL)

(*) Notice: Subject to any disclaimer, the term of this patent is extended or adjusted under 35 U.S.C. 154(b) by 0 days.

(21) Appl. No.: 15/328,602

(22) PCT Filed: Jul. 23, 2015

(86) PCT No.: PCT/IL2015/050764
§ 371 (c)(1),
(2) Date: Jan. 24, 2017

(87) PCT Pub. No.: WO2016/013019
PCT Pub. Date: Jan. 28, 2016

(65) Prior Publication Data
US 2017/0335328 A1 Nov. 23, 2017

Related U.S. Application Data

(60) Provisional application No. 62/028,328, filed on Jul. 24, 2014.

(51) Int. Cl.
A61K 48/00 (2006.01)
C12N 15/113 (2010.01)
A61K 31/7105 (2006.01)
A61K 31/713 (2006.01)
A61K 9/00 (2006.01)
A61K 41/00 (2006.01)
A61P 17/06 (2006.01)
A61P 17/00 (2006.01)

(52) U.S. Cl.
CPC ........ *C12N 15/1136* (2013.01); *A61K 9/0014* (2013.01); *A61K 31/713* (2013.01); *A61K 31/7105* (2013.01); *A61K 41/0047* (2013.01); *A61P 17/00* (2018.01); *A61P 17/06* (2018.01); *C12N 15/113* (2013.01); *C12N 2310/141* (2013.01); *C12N 2310/531* (2013.01); *C12N 2330/50* (2013.01)

(58) Field of Classification Search
None
See application file for complete search history.

(56) References Cited

U.S. PATENT DOCUMENTS 5,912,120 A 6/1999 Goldstein et al.
2010/0202973 A1* 8/2010 Pivarcsi ............... C12Q 1/6883
424/9.2

FOREIGN PATENT DOCUMENTS

WO 2008/142567 11/2008
WO 2009/137505 11/2009

OTHER PUBLICATIONS

Azagury et al. (Advanced Drug Delivery Review 72 (2014) 127-143).*
Altschul et al., "Gapped BLAST and PSI-BLAST: a new generation of protein database search programs", Nucleic Acids Research, 25(17): (1997) 3389-3402.
Ghosh, "Object-oriented transcription factors database (ooTFD)", Nucleic Acids Research, 28(1): (2000) 308-310.
Heinemeyer et al., "Databases on transcriptional regulation: TRANSFAC, TRRD and COMPEL", Nucleic Acids Research, 26(1): (1998) 362-367.
Lerman et al., "MiRNA expression in psoriatic skin: reciprocal regulation of hsa-miR-99a and IGF-1R", PLoS One, 6(6): (2011) e20916; 13 pages.
Lerman et al., "The crosstalk between IL-22 signaling and miR-197 in human keratinocytes", PLoS One, 9(9): (2014) e107467; 13 pages.
Needleman and Wunsch, "A general method applicable to the search for similarities in the amino acid sequence of two proteins", J Mol Biol, 48(3): (1970) 443-453.
Pearson and Lipman, "Improved tools for biological sequence comparison", Proc Natl Acad Sci USA, 85(8): (1988) 2444-2448.
Smith and Waterman, "Comparison of biosequences", Advances in Applied Mathematics, 2(4): (1981) 482-489.
Sonnenberg et al., "Functional biology of the IL-22-IL-22R pathway in regulating immunity and inflammation at barrier surfaces", Adv. Immunol., 107: (2010) 1-29.
Voorhoeve et al., "A genetic screen implicates miRNA-372 and miRNA-373 as oncogenes in testicular germ cell tumors", Cell, 124(6): (2006) 1169-1181.
Xu et al., "MiR-125b, a microRNA downregulated in psoriasis, modulates keratinocyte proliferation by targeting FGFR2", J Invest Dermatol, 131(7): (2011) 1521-1529.
International Search Report dated Nov. 18, 2015, in corresponding application No. PCT/IL2015/050764.

(Continued)

*Primary Examiner* — Kimberly Chong
(74) *Attorney, Agent, or Firm* — Wenderoth, Lind & Ponack, L.L.P.

(57) ABSTRACT

The present invention relates to methods of treating, preventing, reducing the severity of, reducing the incidence of, delaying the onset of, or reducing pathogenesis of an inflammatory skin disease, condition or lesion in a human subject, which include the step of administering to the subject a therapeutically effective amount of mi RNA compositions. In addition, methods of this invention may be used to treat symptoms of inflammatory skin diseases and reduce and/or inhibit keratinocyte proliferation.

19 Claims, 30 Drawing Sheets

Specification includes a Sequence Listing.

(56) References Cited

OTHER PUBLICATIONS

Bostjancic et al., "Importance of microRNAs in skin morphogenesis and diseases", Acta Dermatovenerol Alp Pannonica Adriat, 17(3): 95-102 (2008).

Sonkoly et al., "MicroRNAs: novel regulators in skin inflammation", Clinical and Experimental Dermatology, 33(3): 312-315 (2008).

* cited by examiner

IL22RA1 3'UTR

```
             mir-197 binding site
       920........930........940........950........960........970........980........990
SEQ ID NO. 41  Hsa  UGGGGAUCAUAACACCUACCUCA                UU  GAUGAA---AUGAAGUCAUGUCUUUAAAGUGCUUAAUAGU
SEQ ID NO. 42  Pti  UGGGGAUCAUAACACCUACCUCA                UU  GAUGAA---AUGAAGUCAUGUCUUUAAAGUGCUUAAUAGU
SEQ ID NO. 43  Mml  UGGGCAUCAUAACACCUACCUCA                G UU  GAUGAA---AUGAAGUCAUGUCUUUAAAGCGCUUAAUAAU
SEQ ID NO. 44  Oga  UGGCAACAAUACCUACCCUUACA U UU           GGAUGAC---AUUGAAUAAUGUCGAAGUGCGAAGUGCUUAACUA-U
                                                    ||||||  ||||||
SEQ ID NO. 8   3'--CGACCCACUCUCCACCACUU-5'   miR-197
```

FIGURE 5A

```
                 ...390.......400.......410.......420.......430........440
SEQ ID NO. 45    Hsa     GUUCAAGAGACCAGCCUGGCCAAUA    ACCCAGUCUCUACUAAAAAUACAAAAAUUAGCUAG
SEQ ID NO. 46    Ptr     GUUCAAGAGACCAGCCUGGCCAACA    ACCCAGUCUCUACUAAAAAUACAAAAAUUAGCUAG
                                                   ||||||
SEQ ID NO. 8     hsa-miR-197  3'-CGACCCACCUCUUCCAACCACUCU-5'
```

FIGURE 6A

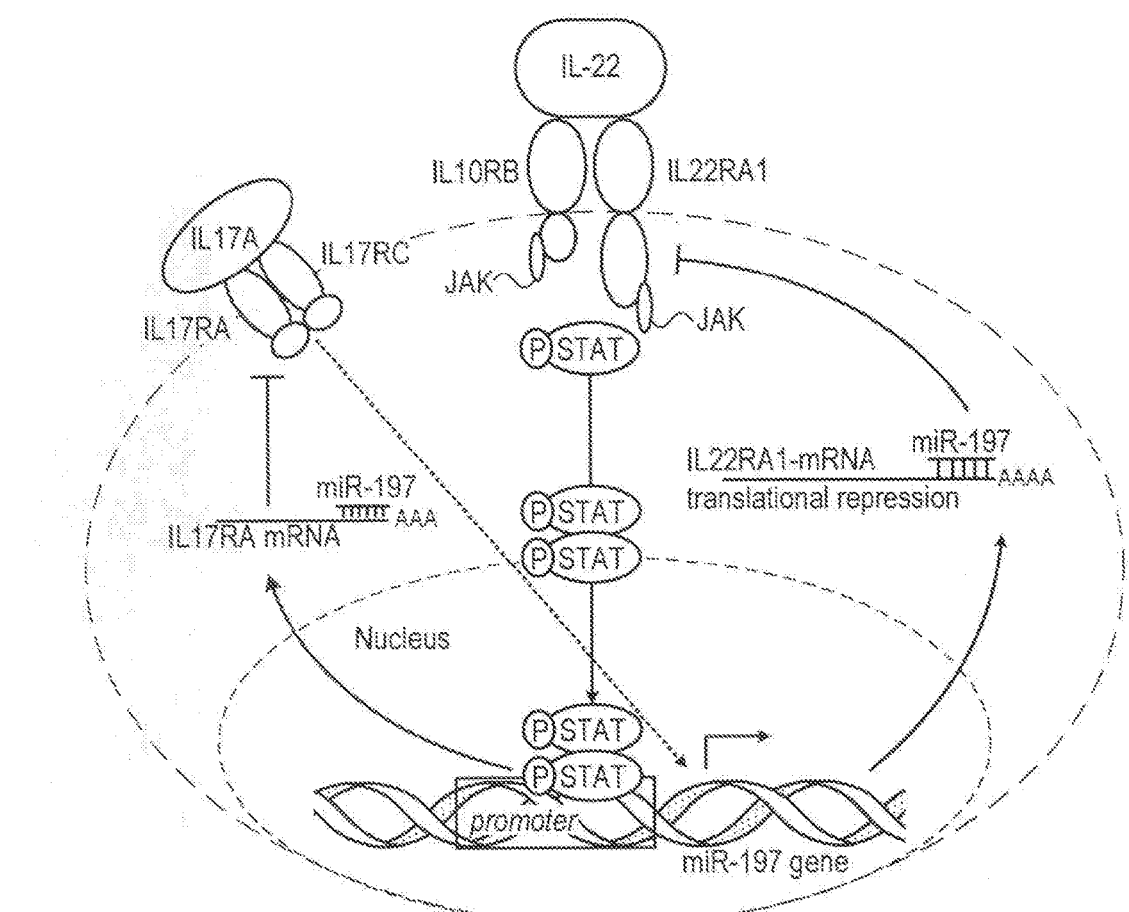
FIGURE 7
FIGURE 8A
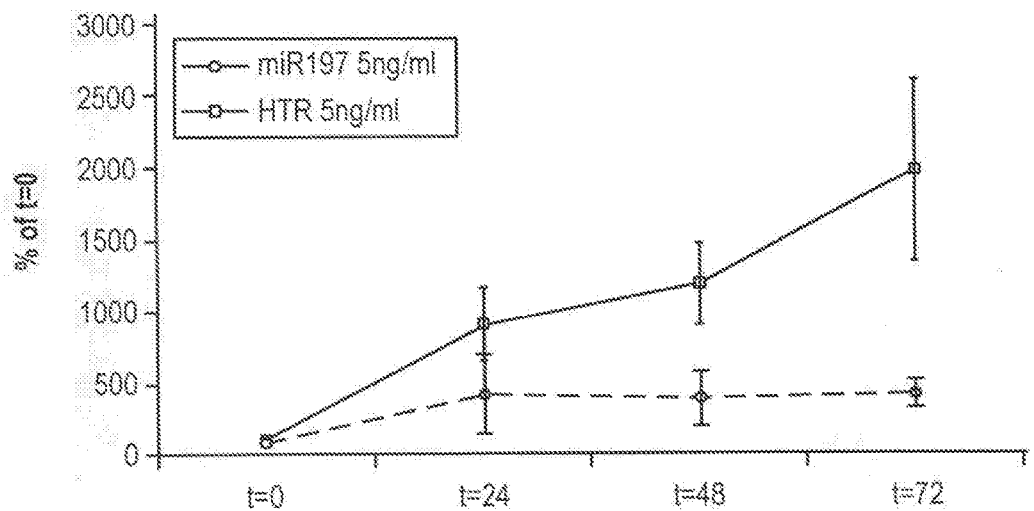

FIGURE 10B

FIGURE 10C (SEQ ID NO: 72)

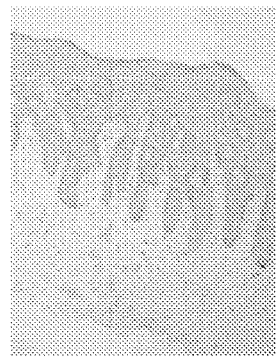 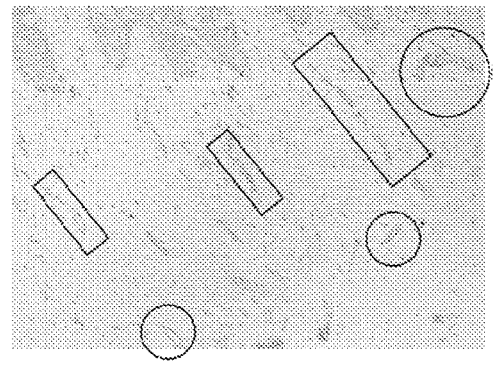
FIGURE 20A  FIGURE 20B
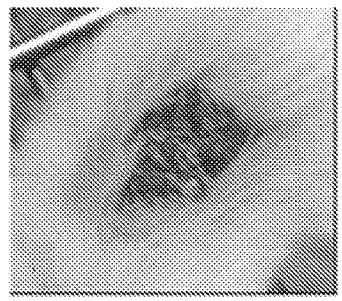 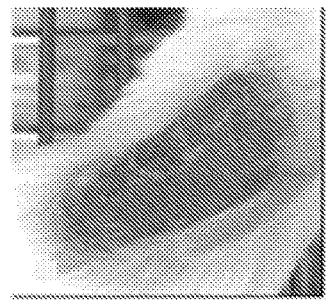
FIGURE 21A  FIGURE 21B
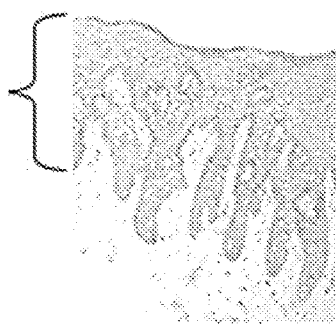 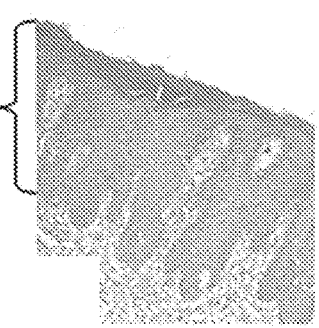
FIGURE 21C  FIGURE 21D
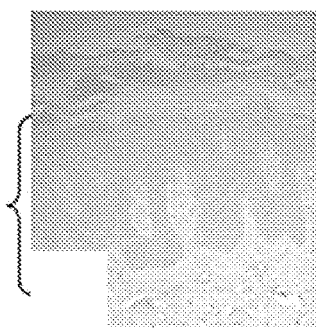 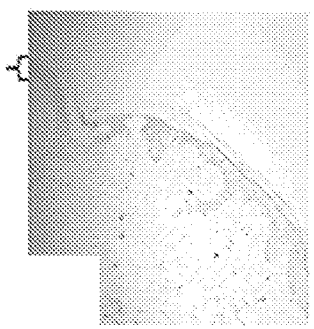
FIGURE 21E  FIGURE 21F

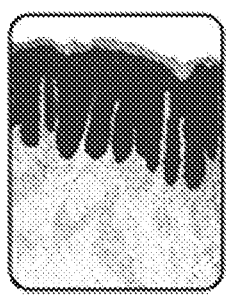
FIGURE 22A    FIGURE 22B    FIGURE 22C
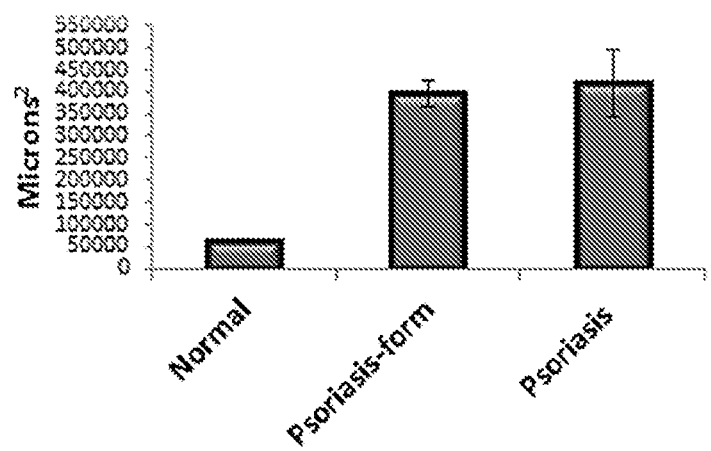
FIGURE 22D

SEQUENCE LISTING

<160> NUMBER OF SEQ ID NOS: 77

<210> SEQ ID NO 1
<211> LENGTH: 33
<212> TYPE: DNA
<213> ORGANISM: Artificial Sequence
<220> FEATURE:
<223> OTHER INFORMATION: Forward primer with Xho

<400> SEQUENCE: 1
ccgctcgagc ggggaatggg aaaggcttgg tgc                              33

<210> SEQ ID NO 2
<211> LENGTH: 45
<212> TYPE: DNA
<213> ORGANISM: Artificial Sequence
<220> FEATURE:
<223> OTHER INFORMATION: Reverse primer with NotI

<400> SEQUENCE: 2
atagtttagc ggccgcattc ttatgctacc gtttattggg cactg                 45

<210> SEQ ID NO 3
<211> LENGTH: 28
<212> TYPE: DNA
<213> ORGANISM: Artificial Sequence
<220> FEATURE:
<223> OTHER INFORMATION: Mutant primer

<400> SEQUENCE: 3
ctcatggagt tgtaacaaag atgaaatg                                    28

<210> SEQ ID NO 4
<211> LENGTH: 21
<212> TYPE: DNA
<213> ORGANISM: Artificial Sequence
<220> FEATURE:
<223> OTHER INFORMATION: Forward Primer

<400> SEQUENCE: 4
agtgggtggt cttttacagc a                                           21

<210> SEQ ID NO 5
<211> LENGTH: 20
<212> TYPE: DNA
<213> ORGANISM: Artificial Sequence
<220> FEATURE:
<223> OTHER INFORMATION: Reverse primer

<400> SEQUENCE: 5

```
gaccttttca ccctgcttca                                                    20

<210> SEQ ID NO 6
<211> LENGTH: 35
<212> TYPE: DNA
<213> ORGANISM: Artificial Sequence
<220> FEATURE:
<223> OTHER INFORMATION: Forward primer

<400> SEQUENCE: 6
ttttattaaa aatataaaaa ttagttaggt atggt                                   35

<210> SEQ ID NO 7
<211> LENGTH: 27
<212> TYPE: DNA
<213> ORGANISM: Artificial Sequence
<220> FEATURE:
<223> OTHER INFORMATION: Reverse primer

<400> SEQUENCE: 7
atagagtgag tttgtttttt ttttgtt                                            27

<210> SEQ ID NO 8
<211> LENGTH: 22
<212> TYPE: RNA
<213> ORGANISM: Homo sapiens

<400> SEQUENCE: 8
uucaccaccu ucuccaccca gc                                                 22

<210> SEQ ID NO 9
<211> LENGTH: 75
<212> TYPE: RNA
<213> ORGANISM: Homo sapiens

<400> SEQUENCE: 9
ggcugugccg gguagagagg gcagugggag guaagagcuc uucacccuuc accaccuucu        60
ccacccagca uggcc                                                         75

<210> SEQ ID NO 10
<211> LENGTH: 21
<212> TYPE: DNA
<213> ORGANISM: Artificial Sequence
<220> FEATURE:
<223> OTHER INFORMATION: Forward primer

<400> SEQUENCE: 10
agtgggtggt cttttacagc a                                                  21

<210> SEQ ID NO 11
<211> LENGTH: 20
<212> TYPE: DNA
<213> ORGANISM: Artificial Sequence
<220> FEATURE:
<223> OTHER INFORMATION: Reverse primer

<400> SEQUENCE: 11
tgaagcaggg tgaaaaggtc                                                    20

<210> SEQ ID NO 12
<211> LENGTH: 22
<212> TYPE: RNA
<213> ORGANISM: Homo sapiens
```

<400> SEQUENCE: 12
ugagguagua gguuguaugg uu                                        22

<210> SEQ ID NO 13
<211> LENGTH: 89
<212> TYPE: RNA
<213> ORGANISM: Homo sapiens

<400> SEQUENCE: 13
accagacuuu uccuaguccc ugagacccua acuugugagg uauuuuagua acaucacaag   60
ucaggcucuu gggaccuagg cggagggga                                    89

<210> SEQ ID NO 14
<211> LENGTH: 22
<212> TYPE: RNA
<213> ORGANISM: Homo sapiens

<400> SEQUENCE: 14
ucccugagac ccuaacuugu ga                                        22

<210> SEQ ID NO 15
<211> LENGTH: 84
<212> TYPE: RNA
<213> ORGANISM: Homo sapiens

<400> SEQUENCE: 15
gcauccgggu ugagguagua gguuguaugg uuuagaguua cacccuggga guuaacugua   60
caaccuucua gcuuuccuug gagc                                         84

<210> SEQ ID NO 16
<211> LENGTH: 81
<212> TYPE: RNA
<213> ORGANISM: Homo sapiens

<400> SEQUENCE: 16
cccauuggca uaaacccgua gauccgaucu ugguggugaag uggaccgcac aagcucgcuu   60
cuaugggucu gugucagugu g                                            81

<210> SEQ ID NO 17
<211> LENGTH: 22
<212> TYPE: RNA
<213> ORGANISM: Homo sapiens

<400> SEQUENCE: 17
aacccguaga uccgaucuug ug                                        22

<210> SEQ ID NO 18
<211> LENGTH: 94
<212> TYPE: RNA
<213> ORGANISM: Homo sapiens

<400> SEQUENCE: 18
auaaaggaag uuaggcugag gggcagagag cgagacuuuu cuauuuucca aaagcucggu   60
cugaggcccc ucagucuugc uuccuaaccc gcgc                              94

<210> SEQ ID NO 19
<211> LENGTH: 23
<212> TYPE: RNA
<213> ORGANISM: Homo sapiens

<400> SEQUENCE: 19
agcucggucu gaggccccuc agu                                                23

<210> SEQ ID NO 20
<211> LENGTH: 84
<212> TYPE: RNA
<213> ORGANISM: Homo sapiens

<400> SEQUENCE: 20
cuccccaugg cccugucucc caacccuugu accagugcug ggcucagacc cugguacagg        60 ccuggggac agggaccugg ggac                                                84

<210> SEQ ID NO 21
<211> LENGTH: 22
<212> TYPE: RNA
<213> ORGANISM: Homo sapiens

<400> SEQUENCE: 21
ucucccaacc cuuguaccag ug                                                 22

<210> SEQ ID NO 22
<211> LENGTH: 22
<212> TYPE: RNA
<213> ORGANISM: Homo sapiens

<400> SEQUENCE: 22
cugguacagg ccuggggac ag                                                  22

<210> SEQ ID NO 23
<211> LENGTH: 89
<212> TYPE: DNA
<213> ORGANISM: Homo sapiens
<220> FEATURE:
<221> NAME/KEY: misc_feature
<223> OTHER INFORMATION: n is ~ 550 bp
<220> FEATURE:
<221> NAME/KEY: misc_feature
<222> LOCATION: (60)..(60)
<223> OTHER INFORMATION: n is a, c, g, or t

<400> SEQUENCE: 23
agcctttgta tgcccagtgc tagtgttttc ctgaaatcta gtgagaatca caaggtaccn        60
agtgggtggt cttttacagc attactttg                                          89

<210> SEQ ID NO 24
<211> LENGTH: 89
<212> TYPE: DNA
<213> ORGANISM: Macaca nemestrina
<220> FEATURE:
<221> NAME/KEY: misc_feature
<223> OTHER INFORMATION: n is ~ 550 bp
<220> FEATURE:
<221> NAME/KEY: misc_feature
<222> LOCATION: (60)..(60)
<223> OTHER INFORMATION: n is a, c, g, or t

<400> SEQUENCE: 24
agcctttgta tgctcagtgc tagtgttttt ctgaaattca gtgagaatca caaggtaccn        60
agtgggtggt cttttacagc attactttg                                          89

<210> SEQ ID NO 25
<211> LENGTH: 89
<212> TYPE: DNA
<213> ORGANISM: Pan troglodytes
<220> FEATURE:

<221> NAME/KEY: misc_feature
<223> OTHER INFORMATION: n is ~ 550 bp
<220> FEATURE:
<221> NAME/KEY: misc_feature
<222> LOCATION: (60)..(60)
<223> OTHER INFORMATION: n is a, c, g, or t

<400> SEQUENCE: 25
agcctttgta tgcccagtgc tagtgttttc ctgaaatcta gtgagaatca caaggtaccn    60
agtgggtggt cttttacagc attactttg                                      89

<210> SEQ ID NO 26
<211> LENGTH: 89
<212> TYPE: DNA
<213> ORGANISM: Nomascus leucogenys
<220> FEATURE:
<221> NAME/KEY: misc_feature
<223> OTHER INFORMATION: n is ~ 550 bp
<220> FEATURE:
<221> NAME/KEY: misc_feature
<222> LOCATION: (60)..(60)
<223> OTHER INFORMATION: n is a, c, g, or t

<400> SEQUENCE: 26
agcctttgta tgcccagtgc tagtgttttc ctgaaatcta gtgagaatca caaggtaccn    60
agtgggtggt cttttacagc attactttg                                      89

<210> SEQ ID NO 27
<211> LENGTH: 90
<212> TYPE: DNA
<213> ORGANISM: Callithrix jacchus
<220> FEATURE:
<221> NAME/KEY: misc_feature
<223> OTHER INFORMATION: n is ~ 550 bp
<220> FEATURE:
<221> NAME/KEY: misc_feature
<222> LOCATION: (61)..(61)
<223> OTHER INFORMATION: n is a, c, g, or t

<400> SEQUENCE: 27
atgcctgtgt atgcccagtg ctagtgtttt ccttaaatct aataggactc acaaggtacc    60
nagtgggtgg tcttttacag cattactttg                                     90

<210> SEQ ID NO 28
<211> LENGTH: 37
<212> TYPE: DNA
<213> ORGANISM: Pan paniscus
<220> FEATURE:
<221> NAME/KEY: misc_feature
<223> OTHER INFORMATION: n is ~ 550 bp
<220> FEATURE:
<221> NAME/KEY: misc_feature
<222> LOCATION: (8)..(8)
<223> OTHER INFORMATION: n is a, c, g, or t

<400> SEQUENCE: 28
atgctttnag tgggtggtct tttacagcat tactttg                             37

<210> SEQ ID NO 29
<211> LENGTH: 94
<212> TYPE: DNA
<213> ORGANISM: Homo sapiens
<220> FEATURE:
<221> NAME/KEY: misc_feature
<223> OTHER INFORMATION: n is 177 bp
<220> FEATURE:
<221> NAME/KEY: misc_feature
<222> LOCATION: (79)..(79)

<223> OTHER INFORMATION: n is a, c, g, or t

<400> SEQUENCE: 29
cccatattca ttttgaagac ctgaaatgaa gttgaactat aaattgctct aaaattcgtg    60
aagcagggtg aaaaggtcnc tggcccaaca ccga                                94

<210> SEQ ID NO 30
<211> LENGTH: 94
<212> TYPE: DNA
<213> ORGANISM: Macaca nemestrina
<220> FEATURE:
<221> NAME/KEY: misc_feature
<223> OTHER INFORMATION: n is 177 bp
<220> FEATURE:
<221> NAME/KEY: misc_feature
<222> LOCATION: (79)..(79)
<223> OTHER INFORMATION: n is a, c, g, or t

<400> SEQUENCE: 30
cccatattca ttttgaagac ctgaaatgaa gttgaactat aaattgctct aaaattcgtg    60
aagcagggtg aaaaggtcnc tggcccaaca ccga                                94

<210> SEQ ID NO 31
<211> LENGTH: 94
<212> TYPE: DNA
<213> ORGANISM: Pan troglodytes
<220> FEATURE:
<221> NAME/KEY: misc_feature
<223> OTHER INFORMATION: n is 177 bp
<220> FEATURE:
<221> NAME/KEY: misc_feature
<222> LOCATION: (79)..(79)
<223> OTHER INFORMATION: n is a, c, g, or t

<400> SEQUENCE: 31
cccatattca ttttgaagac ctgaaatgaa gttgaactat aaattgctct aaaattcgtg    60
aagcagggtg aaaaggtcnc tggcccaaga ccga                                94

<210> SEQ ID NO 32
<211> LENGTH: 88
<212> TYPE: DNA
<213> ORGANISM: Nomascus leucogenys
<220> FEATURE:
<221> NAME/KEY: misc_feature
<223> OTHER INFORMATION: n is 177 bp
<220> FEATURE:
<221> NAME/KEY: misc_feature
<222> LOCATION: (73)..(73)
<223> OTHER INFORMATION: n is a, c, g, or t

<400> SEQUENCE: 32
cccatattca ttttgaagac gtgaagttga actataaatt gctctaaaat tcgtgaagca    60
gtgtgaaaag tcnctggccc aacaccga                                       88

<210> SEQ ID NO 33
<211> LENGTH: 94
<212> TYPE: DNA
<213> ORGANISM: Callithrix jacchus
<220> FEATURE:
<221> NAME/KEY: misc_feature
<223> OTHER INFORMATION: n is 177 bp
<220> FEATURE:
<221> NAME/KEY: misc_feature
<222> LOCATION: (79)..(79)
<223> OTHER INFORMATION: n is a, c, g, or t

<400> SEQUENCE: 33
cccgtattca ttttgaagac ctgaaatgaa gttgaactgt aaattgctct aaaatgcatg    60
aagcagtgtg aaaaggtcnc tggcccaaca ccga                               94

<210> SEQ ID NO 34
<211> LENGTH: 94
<212> TYPE: DNA
<213> ORGANISM: Pan paniscus
<220> FEATURE:
<221> NAME/KEY: misc_feature
<223> OTHER INFORMATION: n is 177 bp
<220> FEATURE:
<221> NAME/KEY: misc_feature
<222> LOCATION: (79)..(79)
<223> OTHER INFORMATION: n is a, c, g, or t

<400> SEQUENCE: 34
cccatattca ttttgaagac ctgaaatgaa gttgaactat aaattgctct aaaattcgtg    60
aagcagggtg aaaaggtcnc tggcccaaga ccga                               94

<210> SEQ ID NO 35
<211> LENGTH: 103
<212> TYPE: DNA
<213> ORGANISM: Homo sapiens

<400> SEQUENCE: 35
aatccttctg gaatctgtgc tctgggggct gtgccgggta gagagggcag tgggaggtaa    60
gagctcttca cccttcacca ccttctccac ccagcatggc cgg                    103

<210> SEQ ID NO 36
<211> LENGTH: 103
<212> TYPE: DNA
<213> ORGANISM: Macaca nemestrina

<400> SEQUENCE: 36
aatcctgctg gaatctgtgc tccgggggct gtgccgggta gagagggcag tgggaggtaa    60
gagctcttca cccttcacca ccttctccac ccagcatggc cgg                    103

<210> SEQ ID NO 37
<211> LENGTH: 103
<212> TYPE: DNA
<213> ORGANISM: Pan troglodytes

<400> SEQUENCE: 37
aatcctgctg gaatctgtgc tctgggggct gtgccgggta gagagggcag tgggaggtaa    60
gagctcttca cccttcacca ccttctccac ccagcatggc cgg                    103

<210> SEQ ID NO 38
<211> LENGTH: 103
<212> TYPE: DNA
<213> ORGANISM: Nomascus leucogenys

<400> SEQUENCE: 38
aatcctgctg gaatctgtgc tccaggggct gtgccgggta gagagggcag tgggaggtaa    60
gagctcttca cccttcacca ccttctccac ccagcatggc cgg                    103

<210> SEQ ID NO 39
<211> LENGTH: 106
<212> TYPE: DNA
<213> ORGANISM: Callithrix jacchus

<400> SEQUENCE: 39
agtcctcctg ctggaatctg tgctccgggg gctgtgccgg gtagagaggg cagtgggagg    60
taagagctct tcacccttca ccaccttctc cacccagcat ggccgg    106

<210> SEQ ID NO 40
<211> LENGTH: 103
<212> TYPE: DNA
<213> ORGANISM: Pan paniscus

<400> SEQUENCE: 40
aatcctgctg gaatctgtgc tctgggggct gtgccgggta gagagggcag tgggaggtaa    60
gagctcttca cccttcacca ccttctccac ccagcatggc cgg    103

<210> SEQ ID NO 41
<211> LENGTH: 75
<212> TYPE: RNA
<213> ORGANISM: Homo sapiens

<400> SEQUENCE: 41
uggggaucau aacaccuacc ucauggaguu guggugaaga ugaaaugaag ucaugucuuu    60
aaagugcuua auagu    75

<210> SEQ ID NO 42
<211> LENGTH: 75
<212> TYPE: RNA
<213> ORGANISM: Pan troglodytes

<400> SEQUENCE: 42
uggggaucau aacaccuacc ucauggaguu guggugaaga ugaaaugaag ucaugucuuu    60
aaagugcuua auagu    75

<210> SEQ ID NO 43
<211> LENGTH: 75
<212> TYPE: RNA
<213> ORGANISM: Macaca mulatta

<400> SEQUENCE: 43
uggggaucau aacaccuacc ucauggggu guggugaaga ugaaauuaag ucaugucuuu    60
aaagcgcuua auaau    75

<210> SEQ ID NO 44
<211> LENGTH: 74
<212> TYPE: RNA
<213> ORGANISM: Otolemur garnetti

<400> SEQUENCE: 44
uggggacaac aauaccuacc uuacaguguu guggugagga ugacauugaa uaaugucugc    60
gaagugcuua cuau    74

<210> SEQ ID NO 45
<211> LENGTH: 65
<212> TYPE: RNA
<213> ORGANISM: Homo sapiens

<400> SEQUENCE: 45
guucaagacc agccuggcca auauggugaa acccagucuc uacuaaaaau acaaaaauua    60
gcuag    65

<210> SEQ ID NO 46

```
<211> LENGTH: 65
<212> TYPE: RNA
<213> ORGANISM: Pan troglodytes

<400> SEQUENCE: 46
guucaagacc agccuggcca acauggugaa acccagucuc uacuaaaaau acaaaaauua      60
gcuag                                                                 65

<210> SEQ ID NO 47
<211> LENGTH: 49
<212> TYPE: DNA
<213> ORGANISM: Homo sapiens

<400> SEQUENCE: 47
ctactcggga ggctgaggca ggagaatcgc ttgaacccgg gaggcggag                 49

<210> SEQ ID NO 48
<211> LENGTH: 49
<212> TYPE: DNA
<213> ORGANISM: Homo sapiens

<400> SEQUENCE: 48
ttattcggga ggttgaggta ggagaatcgt ttgaattcgg gaggcggag                 49

<210> SEQ ID NO 49
<211> LENGTH: 81
<212> TYPE: DNA
<213> ORGANISM: Homo sapiens

<400> SEQUENCE: 49
ggggctgtgc cgggtagaga gggcagtggg aggtaagagc tcttcaccct tcaccacctt      60
ctccacccag catggccggc a                                                81

<210> SEQ ID NO 50
<211> LENGTH: 81
<212> TYPE: DNA
<213> ORGANISM: Pan troglodytes

<400> SEQUENCE: 50
ggggctgtgc cgggtagaga gggcagtggg aggtaagagc tcttcaccct tcaccacctt      60
ctccacccag catggccggc a                                                81

<210> SEQ ID NO 51
<211> LENGTH: 81
<212> TYPE: DNA
<213> ORGANISM: Gorilla gorilla

<400> SEQUENCE: 51
ggggctgtgc cgggtagaga gggcagtggg aggtaagagc tcttcaccct tcaccacctt      60
ctccacccag catggccggc a                                                81

<210> SEQ ID NO 52
<211> LENGTH: 81
<212> TYPE: DNA
<213> ORGANISM: Pongo abelii

<400> SEQUENCE: 52
ggggctgtgc cgggtagaga gggcagtggg aggtaagagc tcttcaccct tcaccacctt      60
ctccacccag catggccggc a                                                81
```

```
<210> SEQ ID NO 53
<211> LENGTH: 81
<212> TYPE: DNA
<213> ORGANISM: Macaca mulatta

<400> SEQUENCE: 53
ggggctgtgc cgggtagaga gggcagtggg aggtaagagc tcttcaccct tcaccacctt      60
ctccacccag catggccggc a                                                81

<210> SEQ ID NO 54
<211> LENGTH: 81
<212> TYPE: DNA
<213> ORGANISM: Callithrix jacchus

<400> SEQUENCE: 54
ggggctgtgc cgggtagaga gggcagtggg aggtaagagc tcttcaccct tcaccacctt      60
ctccacccag catggccggc a                                                81

<210> SEQ ID NO 55
<211> LENGTH: 45
<212> TYPE: DNA
<213> ORGANISM: Mus musculus

<400> SEQUENCE: 55
ggggatgtgc tgggcagacc ccttctcctc ctagcattgc cagca                      45

<210> SEQ ID NO 56
<211> LENGTH: 78
<212> TYPE: DNA
<213> ORGANISM: Rattus norvegicus

<400> SEQUENCE: 56
ggggctgtgc tgggcagaga ggacagtggg agatcagtgt ccttcatgat tggctccctt      60
ctcccagcgc tgccagca                                                    78

<210> SEQ ID NO 57
<211> LENGTH: 81
<212> TYPE: DNA
<213> ORGANISM: Bos taurus

<400> SEQUENCE: 57
ggggctgtgc cgggtagaga gggcagtggg aggtaagagc tcttcaccct tcaccacctt      60
ctccacccag cagggccagc a                                                81

<210> SEQ ID NO 58
<211> LENGTH: 81
<212> TYPE: DNA
<213> ORGANISM: Canis lupus familiaris

<400> SEQUENCE: 58
ggggctgtgc cgggtagaga gggcagtggg aggtaagagc tcttcaccct tcaccacctt      60
ctccacccag catggccggc a                                                81

<210> SEQ ID NO 59
<211> LENGTH: 81
<212> TYPE: DNA
<213> ORGANISM: Equus caballus

<400> SEQUENCE: 59
ggggctgtgc cgggtagaga gggcagtggg aggtaagagc tcttcaccct tcaccacctt      60
```

| | |
|---|---|
| ctccacccag catggccggc a | 81 |

<210> SEQ ID NO 60
<211> LENGTH: 81
<212> TYPE: DNA
<213> ORGANISM: Cavia porcellus

<400> SEQUENCE: 60

| | |
|---|---|
| ggggctgtgc cgggtagaga gggcagtggg aggtaagagc tcttcaccct tcaccacctt | 60 |
| ctccacccag catggccagc a | 81 |

<210> SEQ ID NO 61
<211> LENGTH: 74
<212> TYPE: RNA
<213> ORGANISM: Homo sapiens

<400> SEQUENCE: 61

| | |
|---|---|
| aucuguaaug uggggaucau aacaccuacc ucauggaguu guggugaaga ugaaaugaag | 60 |
| ucaugucuuu aaag | 74 |

<210> SEQ ID NO 62
<211> LENGTH: 74
<212> TYPE: RNA
<213> ORGANISM: Pan troglodytes

<400> SEQUENCE: 62

| | |
|---|---|
| aucuguaaca uggggaucau aacaccuacc ucauggaguu guggugaaga ugaaaugaag | 60 |
| ucaugucuuu aaag | 74 |

<210> SEQ ID NO 63
<211> LENGTH: 74
<212> TYPE: RNA
<213> ORGANISM: Gorilla gorilla

<400> SEQUENCE: 63

| | |
|---|---|
| aucuguaacg uggggaucac aacaccuacc ucauggaguu guggugaaga ugaaaugaag | 60 |
| ucacgucuuu aaag | 74 |

<210> SEQ ID NO 64
<211> LENGTH: 74
<212> TYPE: DNA
<213> ORGANISM: Pongo abelii

<400> SEQUENCE: 64

| | |
|---|---|
| aucuguaaca uggggaucau aacaccuacc ucauggaguu guggugaaga ggaaauuaag | 60 |
| tcatgtcttt caag | 74 |

<210> SEQ ID NO 65
<211> LENGTH: 74
<212> TYPE: RNA
<213> ORGANISM: Rhesus macaque

<400> SEQUENCE: 65

| | |
|---|---|
| auuuguaaca uggggaucau aacaccuacc ucauggguu guggugaaga ugaaauuaag | 60 |
| ucaugucuuu aaag | 74 |

<210> SEQ ID NO 66
<211> LENGTH: 70
<212> TYPE: RNA
<213> ORGANISM: Mus musculus

```
<400> SEQUENCE: 66
aucaaugaaa ugggcgucau cacacuuacc uucuggggug gugccaagga uggcauuaau    60
gucugggaau                                                          70

<210> SEQ ID NO 67
<211> LENGTH: 70
<212> TYPE: RNA
<213> ORGANISM: Rattus norvegicus

<400> SEQUENCE: 67
aucaaugaaa ugggcacuau cacacuuacc uucugaggca gugccgagga ugacauuaau    60
gucuggaaau                                                          70

<210> SEQ ID NO 68
<211> LENGTH: 67
<212> TYPE: RNA
<213> ORGANISM: Bos taurus

<400> SEQUENCE: 68
aucuguauaa uggggauagu acugcauggg guugugguga ggcugagauu aaaucauguc    60
uguaaag                                                             67

<210> SEQ ID NO 69
<211> LENGTH: 73
<212> TYPE: RNA
<213> ORGANISM: Canis lupus familiaris

<400> SEQUENCE: 69
aucuguaaaa uggggauagu gacgccugcu ucaaggggau guggugagga ugacauucau    60
aaugucuaua aag                                                      73

<210> SEQ ID NO 70
<211> LENGTH: 74
<212> TYPE: RNA
<213> ORGANISM: Equus caballus

<400> SEQUENCE: 70
auccguaaag uggggaugau aacaccuacc ucacuggguu gcggugagga agaaaucaca    60
uggugucugu aagg                                                     74

<210> SEQ ID NO 71
<211> LENGTH: 22
<212> TYPE: RNA
<213> ORGANISM: Artificial Sequence
<220> FEATURE:
<223> OTHER INFORMATION: miR-197 antago

<400> SEQUENCE: 71
gcugggugga gaagguggug aa                                            22

<210> SEQ ID NO 72
<211> LENGTH: 44
<212> TYPE: DNA
<213> ORGANISM: Artificial Sequence
<220> FEATURE:
<223> OTHER INFORMATION: Synthesized

<400> SEQUENCE: 72
ggtctggagt ttgacccagc ctggccaaca tggtgaaacc ccat                    44
```

```
<210> SEQ ID NO 73
<211> LENGTH: 32
<212> TYPE: DNA
<213> ORGANISM: Artificial Sequence
<220> FEATURE:
<223> OTHER INFORMATION: Synthesized

<400> SEQUENCE: 73
gagccagcct ggccaacatg gtgaaacccc at                                 32

<210> SEQ ID NO 74
<211> LENGTH: 32
<212> TYPE: DNA
<213> ORGANISM: Artificial Sequence
<220> FEATURE:
<223> OTHER INFORMATION: Synthesized

<400> SEQUENCE: 74
gagcgatcct cccttcatc cacatacccc at                                  32

<210> SEQ ID NO 75
<211> LENGTH: 30
<212> TYPE: DNA
<213> ORGANISM: Artificial Sequence
<220> FEATURE:
<223> OTHER INFORMATION: Forward Primer

<400> SEQUENCE: 75
gcgcctcgag ccagctttga gagaggagtg                                    30

<210> SEQ ID NO 76
<211> LENGTH: 30
<212> TYPE: DNA
<213> ORGANISM: Artificial Sequence
<220> FEATURE:
<223> OTHER INFORMATION: Reverse Primer

<400> SEQUENCE: 76
atgcggccgc gaggctcatc agacgaaagg                                    30

<210> SEQ ID NO 77
<211> LENGTH: 45
<212> TYPE: DNA
<213> ORGANISM: Artificial Sequence
<220> FEATURE:
<223> OTHER INFORMATION: Mutant Primer

<400> SEQUENCE: 77
gtggagatgg ggtatgtgga tgaaggggag gatcgctcaa actcc                   45
```

PREVENTING AND TREATING INFLAMMATORY SKIN DISEASES

FIELD OF THE INVENTION

This invention relates to the use of miRNAs for treating, preventing, reducing the severity of, reducing the incidence of, delaying the onset of, or reducing pathogenesis of inflammatory skin diseases, for example psoriasis, in a human subject.

BACKGROUND OF THE INVENTION

Psoriasis is a very common chronic inflammatory skin disorder with an estimated prevalence of 2%. Susceptibility to psoriasis has been mapped to loci on several chromosomes. This multigenic disease is characterized by abnormally increased keratinocyte proliferation, abnormal differentiation of the epidermis and systemic and local inflammation, which result in the formation of chronic erythematous and scaly lesions. Psoriatic epidermal hyper proliferation is characterized by over representation of basal keratinocytes, increased number of mitoses and their presence above the basal layer, evenly thickened epidermis with persistence of cell nuclei in the upper cornified layer, and loss of the granular layer. Keratinocyte transit time through the epidermis is accelerated 10-fold compared to normal skin, and differentiated characteristics do not develop.

MicroRNAs (miRNA) are short (20-24 nucleotides) noncoding RNAs that are involved in post-transcriptional regulation of gene expression in multicellular organisms by affecting both the stability and translation of mRNAs. miRNAs are transcribed by RNA polymerase II as part of capped and polyadenylated primary transcripts that can be either protein-coding or non-coding. The primary transcript is cleaved by the Drosha ribonuclease III enzyme to produce an approximately 70-nt stem-loop precursor miRNA (pre-miRNA), which is further cleaved by the cytoplasmic Dicer ribonuclease to generate the two matures miRNAs the miRNA-5p and the miRNA-3p, also known as miRNA star (miRNA*) product. Both forms of the mature miRNA may be active. The mature miRNA is incorporated into an RNA-induced silencing complex (RISC), which recognizes target mRNAs through imperfect base pairing with the miRNA and most commonly results in translational inhibition or destabilization of the target mRNA.

miRNAs were found to be essential for skin development in a conditional knock-out mouse model of Dicer, a cardinal enzyme for miRNA processing. Loss of keratinocyte-specific Dicer expression produces several distinct defects in the skin that affect both the epithelium and epithelial-mesenchymal signaling. These phenotypes include hyper proliferation in the absence of increased apoptosis. Hence, the importance of miRNAs in skin development is evident, although their precise functions in normal skin development and pathogenic conditions are unknown.

One of the characteristics of psoriasis is the cross talk between activated immunocytes and keratinocytes (KC) that begins early upon lesion formation and culminates in the mature psoriatic plaque. Pathogenic T cells, releasing a cascade of cytokines, infiltrate the skin and trigger a hyper-proliferative response of KC. A discrete population of lymphocytes, namely Th17 cells, was significantly more abundant in the psoriatic skin and seems to play a major role in the pathogenesis of psoriasis. Th17 cells depend on IL-23 for their development, survival and proliferation, they produce IL-17A, IL-17F, TNF-α, IL-21 and IL-22.

Experimental evidence points to the importance of the cytokine interleukin-17A (IL-17A) in the pathogenesis of several inflammatory diseases including psoriasis. IL-17A is produced by few subtype of T cells, it is found at high levels associated with mast cells and neutrophils at sites of skin disease. IL-17A up-regulates expression of numerous inflammation-related genes in target cells such as keratinocytes and fibroblasts, leading to increased production of chemokines, cytokines, antimicrobial peptides and other mediators that contribute to clinical disease features. IL-17A exerts its effects through a heterodimeric receptor complex consisting of IL17RA and IL17RC. Bioinformatics analysis using the Web-based tool 'target scan' (www.targetscan.org) revealed that IL17RA subunit is a potential targets of miR-197.

Th22 cells, which lack the ability to produce IL-17 and IFN-γ, also, produce IL-22. Th22 cells express the chemokine receptor CCR6 and the skin homing receptors CCR4 and CCR10, allowing for infiltration into the skin. They are enriched in the lesional skin of inflammatory skin diseases. This indicates the importance of IL-22 in skin homeostasis and the pathogenesis of skin diseases. Psoriatic patients have markedly elevated IL-22 plasma levels, which correlate with disease severity. IL-22 triggered KC hyperplasia in an in vitro reconstituted human epidermis system. Moreover, neutralization of IL-22 prevented the development of psoriasis in a SCID mouse model of the disease.

Currently, there is no available cure for psoriasis, though there are many treatment options. Topical agents are typically used for mild disease, phototherapy for moderate disease, and systemic agents for severe disease. Psoriasis is known to have a negative impact on the quality of life of both the affected person and the individual's family members. Depending on the severity and location of outbreaks, individuals may experience significant physical discomfort and some disability. Itching and pain can interfere with basic functions, such as self-care and sleep. Participation in sporting activities, certain occupations, and caring for family members can become difficult activities for those with plaques located on their hands and feet. Plaques on the scalp can be particularly embarrassing, as flaky plaque in the hair can be mistaken for dandruff.

Individuals with psoriasis may feel self-conscious about their appearance and have a poor self-image that stems from fear of public rejection and psychosexual concerns. Psoriasis has been associated with low self-esteem and depression is more common among those with the condition. People with psoriasis often feel prejudiced against due to the commonly held incorrect belief that psoriasis is contagious.

There is an unmet need in the art to provide a therapy to treat, prevent, reduce the severity of, reduce the incidence of, delay the onset of, or reduce the pathogenesis of inflammatory skin diseases including psoriasis.

The methods of this invention provide, for example, compositions comprising nucleic acid molecules comprising nucleic acid sequences comprising miRNA sequences, or comprising nucleic acid sequences that express miRNA sequences, for administration to a subject in need to provide a therapy to treat, prevent, reduce the severity of, reduce the incidence of, delay the onset of, or reduce the pathogenesis of inflammatory skin diseases including psoriasis.

SUMMARY OF THE INVENTION

In one embodiment, this invention provides methods of treating, preventing, reducing the severity of, reducing the incidence of, delaying the onset of, or reducing pathogenesis of an inflammatory skin disease, condition or lesion in a human subject, comprising the step of administering to the subject a therapeutically effective amount of a composition comprising a nucleic acid molecule comprising a nucleic acid sequence that is at least 80% identical to an miRNA sequence or wherein the nucleic acid sequence expresses a ribonucleic acid sequence that is at least 80% identical to an miRNA sequence. In one embodiment, the composition comprises a vector comprising a nucleic acid molecule comprising a nucleic acid sequence that is at least 80% identical to an miRNA sequence, or wherein the nucleic acid sequence expresses a ribonucleic acid sequence that is at least 80% identical to an miRNA sequence. In one embodiment, a vector is a viral vector. In another embodiment, a vector is a plasmid vector.

In one embodiment, this invention provides methods of reducing at least one symptom of an inflammatory skin lesion or disease, in a human subject, comprising the step of administering to the subject a therapeutically effective amount of a composition comprising a ribonucleic acid molecule comprising a nucleic acid sequence that is at least 80% identical to an miRNA sequence, or wherein the nucleic acid sequence expresses a ribonucleic acid sequence that is at least 80% identical to an miRNA sequence.

In one embodiment, this invention provides methods of reducing or inhibiting keratinocyte proliferation in a human subject, comprising the step of administering to the subject a therapeutically effective amount of a composition comprising a nucleic acid molecule that comprises a nucleic acid molecule comprising a ribonucleic acid sequence that is at least 80% identical to an miRNA sequence, or wherein the nucleic acid molecule expresses a ribonucleic acid sequence that is at least 80% identical to an miRNA sequence.

In one embodiment, an miRNA sequence comprises a pre-miRNA sequence or a mature miRNA sequence. In one embodiment, nucleic acid sequence comprises at least two miRNA sequences. In one embodiment, an miRNA sequence comprises a hairpin structure. In one embodiment an miRNA sequence of this invention has reduced expression in psoriatic skin lesions.

In one embodiment, an miRNA sequence comprises a sequence selected from the group comprising pre-miR-197 [SEQ ID NO: 9], mature miR-197 [SEQ ID NO: 8], pre-miR-99a [SEQ ID NO: 16], mature miR-99a [SEQ ID NO: 17], pre-miR-Let7c [SEQ ID NO: 12], mature miR-Let7c [SEQ ID NO: 13], pre-miR-125b-2 [SEQ ID NO: 14] or mature miR-125b-2[SEQ ID NO: 15], or any combination thereof, wherein in one embodiment an miRNA sequence comprises miR-197 [SEQ ID NO: 8], in other embodiment an miRNA sequence comprises miR-99a [SEQ ID NO: 17], in yet another embodiment an miRNA sequence comprises miR-Let7c [SEQ ID NO: 13], and in still another embodiment an miRNA sequence comprises miR-125b-1 [SEQ ID NO: 15].

In one embodiment, an inflammatory skin disease, condition or lesion comprised in a method of this invention is selected from the group comprising eczema, psoriasis, atopic dermatitis, lichen planus, bullous pemphigoid, vasculitis, granuloma annulare, acne, keloid formation, abnormalities in skin pigmentation, solar keratosis, solar elastosis, wound healing, epithelial inflammation, and cosmetic indications, or any combination thereof. In one embodiment, an inflammatory skin disease comprises psoriasis. In one embodiment, psoriasis comprises plaque psoriasis, guttate psoriasis, inverse psoriasis, pustular psoriasis, or erythrodermic psoriasis, or any combination thereof. In one embodiment, the psoriasis may be mild, moderate or severe.

In one embodiment, method of this invention for treating, preventing, reducing the severity of, reducing the incidence of, delaying the onset of, or reducing pathogenesis of the inflammatory skin disease, condition or lesion, reduces at least one symptom of the inflammatory skin disease, condition or lesion. In one embodiment, at least one symptom of an inflammatory skin disease, condition or lesion comprises scaly patches on the skin, itchy skin, burning skin, stinging skin or pain, abnormal scar formation, abnormal pigmentation, skin creases, sun exposure damage or any combination thereof.

In one embodiment, an inflammatory skin disease, condition or lesion is present at least on an outside surface of skin. In certain embodiments, a skin surface comprises an elbow, knee, hand, finger, leg, foot, face, nail, genital or scalp, or any combination thereof.

In one embodiment, methods of this invention treating, reducing the severity of, reducing the incidence of, delaying the onset of, or reducing pathogenesis of the inflammatory skin disease, condition or lesion, reduces the number of lesions, reduces the size of the lesions, reduces the spread of a lesion, increases healing of a lesions, or reduces the depth of the lesions, or any combination thereof.

In one embodiment, methods of this invention include topical, transdermal, sub-dermal, enteral, parental or intravenous administration of compositions of this invention. In one embodiment, topical administration comprises use of a cream, gel, ointment, spray, lip-balm, balm, emulsion, liposome, liquid crystal preparation or lotion, or any combination thereof. In one embodiment, administration comprises an at least a once a day administration for at least one day. In another embodiment, administration comprises an at least a twice a day administration for at least one day. In yet another embodiment, administration comprises an at least a once a day administration for at least one week. In still another embodiment, administration comprises an at least a twice a day administration for at least one week. In a further embodiment, administration comprises an at least a once a day administration for at least one month. In another embodiment, administration comprises an at least a twice a day administration for at least one month.

In one embodiment an miRNA of this invention comprises a sequence length of about of about 22 nucleotides wherein miRNA is mature miRNA, or about 60-120 nucleotides wherein miRNA is precursor miRNA. In one embodiment a nucleotide sequence of an miRNA comprises a nucleotide analog or a modified nucleotide. In one embodiment, a nucleic acid molecule is expressed from a viral expression vector, wherein another embodiment a nucleic acid is expressed from a plasmid expression vector. In one embodiment a composition of this invention may comprise a lipid or viral delivery vehicle.

In one embodiment, methods of this invention may promote wound healing.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 1A presents a bar graph showing the results of HaCaT cells transfected with miR-197 (pre-miR-197 expressing plasmid or HTR plasmid (control)). The plasmid expresses the pre-miR-197 [SEQ ID NO.: 9] but in the cells the pre-miR-197 is processed into the mature miR-197 [SEQ ID NO.: 8]. Total RNA was extracted from each cell line, subjected to qPCR analysis using Applied Biosystems TaqMan kits and normalized by RNU48 (*P<0.049988). FIG. 1B presents the graphical results of cell proliferation measured by BrdU incorporation using Cell Proliferation ELISA, BrdU (colorimetric) kit from (Roche). Proliferation was calculated relative to the OD measurement at seeding time (T=0), which was set to be 100%. Mean and standard deviation were calculated from 3 independent experiments (*P<0.0232). FIG. 1C shows involucrin expression measured using total RNA isolated from HaCaT-miR-197 or HaCaT-HTR and subjected to qPCR analysis for involucrin and normalized by Rplp0. Y bars are arbitrary units that define fold change * p=0.05.

FIG. 2A shows BrdU incorporation in HaCat cells in the presence of antago-miR-197 (SEQ ID NO.: 71) or scrambled nucleic acid sequence. FIG. 2B and FIG. 2C show minimal change in % proliferation (BrdU incorporation) in KC following addition of IL-22.

FIG. 3A shows the miR-197 expression 1 h post IL-22 addition *p=0.022. FIG. 3B shows the miR-197 expression 48 h post IL-22 addition, *p=0.01 p=0.017 *p=0.03. (The mean–/+SD was calculated from 4 independent experiments.)

FIG. 4A shows the results of qPCR detecting the mature miR-197 [SEQ ID NO: 8] expression 1 h after IL-22 addition. The mean–/+SD was calculated from 4 independent experiments; *p=0.047699. FIG. 4B shows an alignment of the genomic miR-197 gene region from six primates (Pri) as follows: HSA—*Homo sapiens* [SEQ ID NO: 23; SEQ ID NO: 29; SEQ ID NO: 35]; MNE—*Macaca nemestrina* (Old World monkey) [SEQ ID NO: 24; SEQ ID NO: 30; SEQ ID NO: 36]; PTR—*Pan troglodytes* (chimpanzee) [SEQ ID NO: 25; SEQ ID NO: 31; SEQ ID NO: 37]; NL—*Nomascus leucogenys* (white-cheeked gibbon) [SEQ ID NO: 26; SEQ ID NO: 32; SEQ ID NO: 38]; CJ—*Callithrix jacchus* (New World monkey) [SEQ ID NO: 27; SEQ ID NO: 33; SEQ ID NO: 39]; and PPA—*Pan paniscus* (gracile chimpanzee) [SEQ ID NO: 28; SEQ ID NO: 34; SEQ ID NO: 40]. Pri-miR-197 marked in italic small letters; mature miR-197 marked in bold underline; miRNA "seed" marked in dark gray box; different bases forming consensuses are in black box(es) with white letter. The putative promoter region has 3 conserved STAT sites and one un-conserved (light gray boxes). FIG. 4C shows ChIP-phopho STAT3 antibody binding results. Primary human kidney (PHK) cells were treated or not with 5 ng/ml IL-22 for 30 min, then were subject to ChIP assay using phosphorylated STAT-3 antibody. The results present the amount of immune precipitated DNA by the anti pSTAT3 antibody as measured by PCR divided by the amount of input DNA, as measured by PCR. All PCR assays were performed with qPCR SYBR® Green dye. The mean–/+SD was calculated from 4 independent experiments (t test *P=0.016). Primers that were used in the ChIP assay are marked by underline in FIG. 4B. Forward primer—AGTGGGTGGTCTTTTACAGCA (SEQ ID NO: 10) Reverse primer—TGAAGCAGGGTGAAAAGGTC (SEQ ID NO: 11).

FIGS. 5A-D show miR-197 (SEQ ID NO: 8) suppresses the expression of IL22RA1 by binding to its 3'UTR. FIG. 5A shows the alignment of the miR-197 binding site in the 3' UTR of 1122RA1 from 4 primate species, as follows: HSA—*Homo sapiens* (SEQ ID NO: 41); PTR—*Pan troglodytes* (chimpanzee) (SEQ ID NO: 42); Mm1 *rhesus macaque* (*Macaca mulatta*) (SEQ ID NO: 43); and Oga (*Otolemur garnettii*) (Bushbaby) (SEQ ID NO: 44). Bases forming the consensus binding site of miR-197 to the mRNA 3'UTR of IL22RA1 are in the grey box with white letters. FIG. 5B shows the effect of miR-197 (SEQ ID NO: 8) on IL22RA1-3' UTR. Human embryonic kidney cells (HEK-293 cells) were cotransfected with Luciferase-vector or Luciferase-IL22RA1-3'UTR or Luciferase-IL22RA1-3'UTR mutant for miR-197 binding site plasmid, concomitant with a miR-197 expressing plasmid at different concentrations. Each experiment was done in triplicate. The average of 3 wells transfected with vector lacking the IL22RA1 3'UTR and without miR-197 expressing plasmid was valued as 100%. The error bars are calculated as standard error of at least 6 independent experiments. FIG. 5C shows a Western blot (WB) analysis of IL22RA1 protein 48 h after transfection with 5/10 nM pre-miR-197 (Ambion) (SEQ ID NO: 9). FIG. 5D shows densitometry scan analysis of three WBs analyses of IL22RA1 protein 48 h after transfection with 5/10 nM pre-miR-197 (Ambion) *p= 0.0180 (EZQuant Gel).

FIGS. 6A-C provide results demonstrating that IL1 ORB subunit is not a target of miR-197. FIG. 6A shows the IL10RB 3' UTR position 408-414 of 858 bases, with the miR-197 (SEQ ID NO: 8) binding site in the IL10RB 3' UTR marked by the grey box. Hsa—*Homo sapiens* (SEQ ID NO: 45) and Ptr—*Pan troglodytes* (SEQ ID NO: 46). Bases forming a consensus binding site of miR-197 to the mRNA 3'UTR of IL10RB are in the grey box with white letters. FIG. 6B shows the effect of miR-197 (SEQ ID NO: 8) on IL10RB-3'UTR. HaCaT cells were co-transfected with vector or IL10RB-3'UTR plasmid with a miR-197 expressing plasmid at different concentrations. In each experiment the same set of plasmids were transfected in triplicates. The graph presents the average of 4 independent experiments. The results of cells transfected with vector lacking the IL10RB-3'UTR and without miR-197 expressing plasmid was valued as 100%. FIG. 6C shows the effect of miR-197 (SEQ ID NO: 8) on IL22RA1 3'UTR. HaCaT cells were co-transfected with vector plasmid or luciferase-IL22RA1-3'UTR plasmid and 5 nM of scrambled or mimic miR-197. In parallel one set of cells was transfected with antago-miR-197. Comparison is with a control scrambled nucleic acid sequence.

FIG. 7 presents an embodiment of a feedback loop model depicting the role of miR-197 in the regulation of IL-22 effects and IL-17 effects in normal healthy keratinocytes.

FIGS. 8A-C show that miR-197 (SEQ ID NO: 8) slows proliferation and migration of keratinocytes (KC). FIG. 8A shows the BrdU incorporation in the DNA of HaCaT-miR-197 and control HaCaT-HTR cells following IL-22 addition. BrdU incorporation was carried out as in FIG. 1A. 24 h after seeding, at the 0 time point, 5 ng/ml IL-22 was added. Cell proliferation was calculated as in FIG. 1A. Mean and standard deviation were calculated from 3 independent experiments (*p<0.0145). FIG. 8B shows cell migration in miR-197 overexpressing cells versus control HRT cells. 24,000 cells were seeded on platypus 96 wells plate to reach 80% confluence. Then cells were serum starved for 24 h, afterward, IL-22 was added. 48 h later, cells were washed and fixed. FIG. 8C presents representative micrographs of cell migration: percentage migration was calculated based on the reduction of area, as marked, from the area at time 0. Area was determined using imageJ program. (p<0.001 **p<0.000001).

FIG. 9A provides a schematic presentation of miR-197 promoter. The 8 circles represent the CpG, of the CpG Island. Sequence from −1544 to −1594 of the miR-197 promoter before (SEQ ID NO: 47) and after bisulfite conversion (SEQ ID NO: 48) is shown. The specific CpG assayed are boxed bases; FIG. 9B shows a representative sequencing chromatogram of the bisulfite conversion region, analysis by BioEdit, C and T residues at the CpG are marked.

Figure 10C:
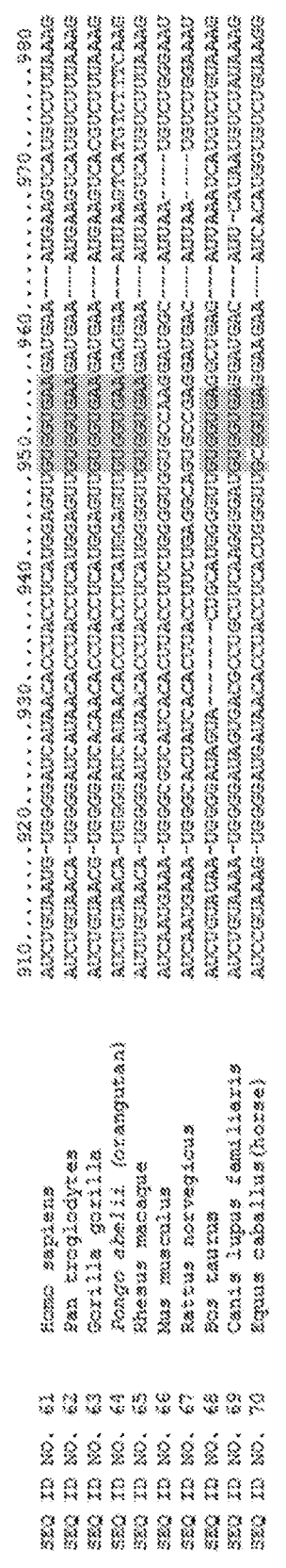

FIGS. 10A-C show the evolutionary conservation of miR-197 (SEQ ID NO: 8) and its putative binding site on IL22RA1 3'UTR. FIG. 10A shows the expression of miR-197 in a range of animal species using the miReviewer program. The name of the species is written above each block. The white dot in box indicates that this miRNA are present in miRbase. Grey box indicates that the miRNA was not identified in the genome of the specific species, under stringent parameters. The degree of conservation is denoted by the greyscale ruler in the bottom section of the figure. Species are as follows: HSA—*Homo sapiens*; PTR—*Pan troglodytes*; GGO—*Gorilla gorilla*; PPY—*Pongo abelii*; MML—*Macaca mulatta*; CJA—*Callithrix jacchus*; TSY—*Tarsius syrichta*; MMR—*Microcebus murinus*; OGA—*Otolemur garnettii*; TBE—*Tupaia belangeri*; CPO—*Cavia porcellus*; DOR—*Dipodomys ordii*; MMU—*Mus musculus*; RNO—*Rattus norvegicus*; STR—*Ictidomys tridecemlineatus*; OPR—*Ochotona princeps*; OCU—*Oryctolagus cuniculus*; BTA—*Bos taurus*; TTR-*Tursiops truncatus*; VPA—*Vicugna pacos*; SSC—*Sus scrofa*; CFA—*Canis lupus familiaris*; FCA-*Felis catus*; ECA—*Equus caballus*; MLU—*Myotis lucifugus*; PVA—*Pteropus vampyrus*; EEU-*Erinaceus europaeus*; SAR—*Sorex araneus*; CHO—*Choloepus hoffmanni*; ETE—*Echinops telfairi*; LAF—*Loxodonta africana*; PCA—*Procavia capensis*; MEU—*Macropus eugenii*; MDO—*Monodelphis domestica*; OAN—*Ornithorhynchus anatinus*; GGA—*Gallus gallus*; MGA—*Meleagris gallopavo*; TGU—*Taeniopygia guttata*; ACA—*Anolis carolinensis*; XTR—*Xenopus tropicalis*; DRE—*Danio rerio*; GAC—*Gasterosteus aculeatus*; OLA—*Oryzias latipes*; TRU—*Takifugu rubripes*; TNI-*Tetraodon nigroviridis*; CIN—*Ciona intestinalis*; CSA—*Ciona savignyi*; DME—*Drosophila melanogaster*; and CEL *Caenorhabditis elegans*. FIG. 10B presents the alignment of pre-miR-197 gene sequences of a few primates including mouse, rat, cow, dog, horse, and guinea pig. *Homo sapiens* (SEQ ID NO: 49); *Pan troglodytes* (SEQ ID NO: 50); *Gorilla gorilla* (SEQ ID NO: 51); *Pongo abelii* (SEQ ID NO: 52); *Macaca mulatta* (SEQ ID NO: 53); *Callithrix jacchus* (SEQ ID NO: 54); *Mus musculus* (SEQ ID NO: 55); *Rattus norvegicus* (SEQ ID NO: 56); *Bos Taurus* (SEQ ID NO: 57); *Canis lupusfamiliaris* (SEQ ID NO: 58); *Equus caballus* (SEQ ID NO: 59); and *Cavia porcellus* (SEQ ID NO: 60). The sequence encoding miR-197 mature miRNA sequence is underlined in each sequence. FIG. 10C presents the alignment of the IL22RA1 3'UTR of some of the above species wherein the mir-197 putative binding site is marked in the shaded regions. *Homo sapiens* (SEQ ID NO: 61); *Pan troglodytes* (SEQ ID NO: 62); *Gorilla gorilla* (SEQ ID NO: 63); *Pongo abelii* (SEQ ID NO: 64); *Rhesus macaque* (SEQ ID NO: 65); *Mus musculus* (SEQ ID NO: 66); *Rattus norvegicus* (SEQ ID NO: 67); *Bos Taurus* (SEQ ID NO: 68); *Canis lupusfamiliaris* (SEQ ID NO: 69); and *Equus caballus* (SEQ ID NO: 70).

FIG. 12A presents a bar graph showing that increasing expression of human Let7c results in decreased expression from the IGF-1R 3'UTR. FIG. 12B presents Western blot data demonstrating down regulation of IGF-1R corresponding with expression of human Let7c and not expression of random miRNA sequence.

FIG. 14D shows the miRNA expression of human mir-99a, mir-125b-2 and mir-Let7c with increasing concentrations of IL-22 after one hour of treatment with IL-22.

FIG. 16B presents that over expression of miR-197 effect the expression of report luciferase gene only if to the luciferase mRNA attach 3'UTR of the IL17RA contained WT binding side to miR-197. FIG. 16C presents Western Blot Data showing the decreased presence of IL17RA with increasing concentrations of miR-197.

FIG. 19A shows the human skin before implantation on mice. FIG. 19B shows the implanted human skin on the mouse 8 days after implantation. FIG. 19C shows the implanted human skin on the mouse 22 days after implantation of psoriasis skin, and two weeks after injection of psoriasis patient activated immune cells into the implanted human skin.

FIGS. 20A and 20B shows tissue sections demonstrating that histologically the implanted skin resembles psoriatic skin. FIG. 20A presents formalin fixed paraffin embedded (FFPE) biopsies of the human skin implanted on the mouse model. FIG. 20B presents FFPE biopsies stained with Von Willebrand factor (marked by circles and rectangles), which is a marker of endothelial blood vessels, and which are known to increase in psoriasis lesion.

FIGS. 21A-21F show comparison of the model when transplanted with normal or psoriasis human skin. FIG. 21A show psoriasis human skin transplanted onto a SCID mouse, two week after injection of psoriasis activated lymphocytes into the implanted skin. While FIG. 21B shows normal, non-psoriatic skin from a human, transplanted onto a SCID mouse, two week after injection of psoriasis activated lymphocytes into the implanted skin FIG. 21C shows a FFPE section of biopsies taken from the skin lesion generated in the mouse implanted with psoriasis skin. FIG. 21D shows a FFPE section of s biopsy taken from the mouse implanted with normal skin. FIG. 21E shows a FFPE section of a biopsy that was taken from a human psoriasis lesion. FIG. 21F shows a FFPE section of a biopsy taken from healthy human. The magnification of all images is the same, and the epidermal thickness is marked in each picture by the side bracket.

FIGS. 22A-D show that the epidermal thickness of implanted human skin in the two mouse models is similar. FIGS. 22A-22C present representative FFPE sections of biopsies that were taken from healthy skin (FIG. 22A), psoriasis-form model (implanted with normal skin) (FIG. 22B), or psoriasis model (FIG. 22C). Quantitation of the epidermal thickness in the psoriasis mouse model is presented in FIG. 22D. The graph represents the average measurement of the epidermis area of 5 health skin FFPE biopsies (normal), or 5 biopsies taken for mice transplanted with healthy skin and injected activated lymphocytes from psoriatic patient (psoriasis-form) or 5 FFPE biopsies taken from mice transplanted with psoriatic skin and injected with activated lymphocytes from psoriatic patient (psoriasis). The area were measure using ImageJ program, from images of the biopsies taken at the same magnitude The magnifications of the picture are the same and the epidermal is marked in each picture.  $p<0.01$; * $p<0.001$ calculated by t-test.

FIG. 23A presents the results of a control transfection. After development of the psoriatic lesion in the mouse the skin was exposed to scrambled unlabeled RNA for 24 h. Next, the mouse was sacrificed and FFPE slides were prepared. Image presents slides that were stained with an antibody against IL22RA1 (green). IL22RA1 staining (circular ring shape) is shown in the enlargement of part of the figure by the white arrows. Images were taken with a confocal microscope. FIG. 23B presents the results of transfection with miR-197. Panel (I): After development of the psoriatic lesion in the mouse, the lesion was sonicated and exposed to miR-197-labeled RNA for 24 h. Next the mouse was sacrificed and FFPE slides were prepared. As can be seen almost all of the cytoplasm of cells in the epidermis is stained with the labeled miRNA, suggesting for miR-197 penetration. Panel (II): The slides were stained with antibody against IL22RA1 (green). There is very low staining of IL22RA1, as compared to FIG. 23A. Images were taken with a confocal microscope.

Figure 1A:
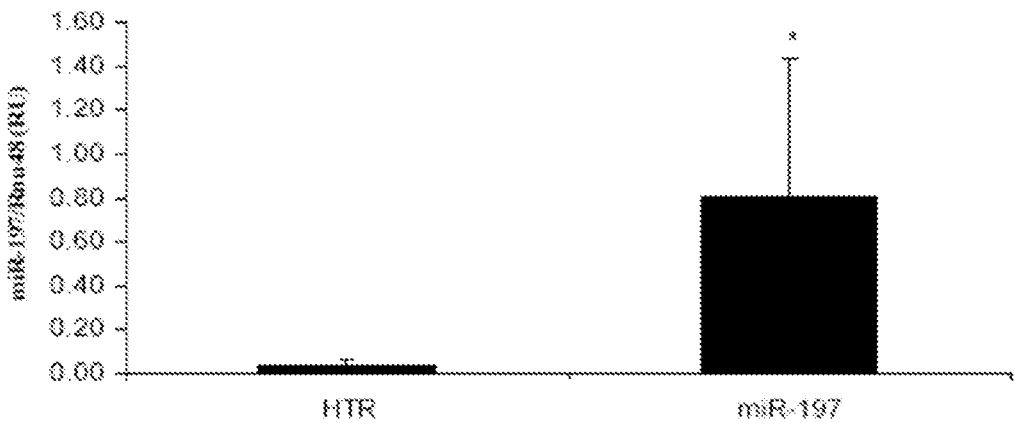
FIGS. 1A-C show the effect of miR-197 on proliferation and differentiation of keratinocytes (KC).

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Inflammatory Skin Diseases, Lesions and Conditions

In one embodiment this invention provides a method of treating, preventing, reducing the severity of, reducing the incidence of, delaying the onset of, or reducing pathogenesis of an inflammatory skin disease, condition or lesion in a human subject, comprising the step of administering to the subject a therapeutically effective amount of a composition comprising a nucleic acid molecule comprising a nucleic acid sequence that is at least 80% identical to an miRNA sequence or wherein the nucleic acid sequence expresses a ribonucleic acid sequence that is at least 80% identical to an miRNA sequence. In one embodiment, treating, preventing, reducing the severity of, reducing the incidence of, delaying the onset of, or reducing pathogenesis of the inflammatory skin disease, condition or lesion, reduces at least one symptom of the inflammatory skin disease, condition or lesion. Each possibility represents a separate embodiment of the present invention.

In another embodiment, a method of this invention comprises treating, preventing, reducing the severity of, reducing the incidence of, delaying the onset of, or reducing pathogenesis of an inflammatory skin disease, condition or lesion in a human subject, comprising the step of administering to the subject a therapeutically effective amount of a composition comprising a vector comprising a nucleic acid molecule comprising a nucleic acid sequence that is at least 80% identical to an miRNA sequence, or wherein the nucleic acid sequence expresses a ribonucleic acid sequence that is at least 80% identical to an miRNA sequence. In one embodiment, the method reduces at least one symptom of the inflammatory skin disease, condition or lesion. Each possibility represents a separate embodiment of the present invention.

As used herein, "treating" refers to both therapeutic treatment and prophylactic or preventative measures, wherein the object is to prevent or lessen the targeted pathologic condition or disorder as described herein, for example an inflammatory skin condition such as psoriasis. Thus, in one embodiment, treating may include directly affecting or curing, suppressing, inhibiting, preventing, reducing the severity of, delaying the onset of, reducing symptoms associated with the disease, disorder or condition, reducing the spread of the disease, disorder or condition, or reducing the pathogenesis of the disease, disorder or condition, or any combination thereof. Thus, in one embodiment, "treating" refers inter alia to delaying progression, expediting remission, inducing remission, augmenting remission, speeding recovery, increasing efficacy of or decreasing resistance to alternative therapeutics, or a combination thereof. In one embodiment, "preventing" refers, inter alia, to delaying the onset of symptoms, preventing relapse to a disease, decreasing the number or frequency of relapse episodes, increasing latency between symptomatic episodes, or a combination thereof. In one embodiment, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

In one embodiment, treating an inflammatory skin disease may include directly affecting or curing, suppressing, inhibiting, preventing, reducing the severity of, delaying the onset of, reducing symptoms associated with lesion formation, reducing the spread of lesions or reduce the pathogenesis of lesions, or any combination thereof.

In one embodiment, a method of this invention comprises reducing at least one symptom of an inflammatory skin lesion or disease, in a human subject, comprising the step of administering to the subject a therapeutically effective amount of a composition comprising a nucleic acid molecule comprising a nucleic acid sequence that is at least 80% identical to an miRNA sequence, or wherein the nucleic acid sequence expresses a ribonucleic acid sequence that is at least 80% identical to an miRNA sequence.

In one embodiment, an inflammatory skin disease treated by the methods of this invention is selected from the group comprising eczema, psoriasis, atopic dermatitis, lichen planus, bullous pemphigoid, vasculitis, granuloma annulare, acne, keloid formation, abnormalities in skin pigmentation, solar keratosis, solar elastosis, wound healing, epithelial inflammation, and cosmetic indications, or any combination thereof. In one embodiment, a method of this invention treats, prevents, reduces the severity of, reduces the incidence of, delays the onset of, or reduces pathogenesis of an inflammatory skin disease selected from the group comprising eczema, psoriasis, atopic dermatitis, lichen planus, bullous pemphigoid, vasculitis, granuloma annulare, acne, keloid formation, abnormalities in skin pigmentation, solar keratosis, solar elastosis, wound healing, epithelial inflammation, and cosmetic indications, or any combination thereof. Each possibility represents a separate embodiment of the present invention.

In one embodiment, an inflammatory skin disease is psoriasis. In one embodiment, a method of this invention treats, prevents, reduces the severity of, reduces the incidence of, delays the onset of, or reduces pathogenesis of psoriasis. In one embodiment, psoriasis comprises plaque psoriasis, guttate psoriasis, inverse psoriasis, pustular psoriasis, or erythrodermic psoriasis, or any combination thereof. In one embodiment, psoriasis is mild, moderate or severe. Each possibility represents a separate embodiment of the present invention.

Symptoms of inflammatory skin diseases may be overlapping. In one embodiment, symptoms of an inflammatory skin disease, for example psoriasis, include raised, red, scaly patches to appear on the skin. These patches may be itchy, may burn or sting, or a combination thereof. In one embodiment, an at least one symptom of an inflammatory skin disease, for example, psoriasis, comprises scaly patches on the skin, itchy skin, burning skin, stinging skin or pain, or any combination thereof. In one embodiment, an at least one symptom of an inflammatory skin disease comprises scaly patches on the skin, itchy skin, burning skin, stinging skin or pain, abnormal scar formation, abnormal pigmentation, skin creases, sun exposure damage or any combination thereof. Each possibility represents a separate embodiment of the present invention.

Keratinocyte hyper proliferation is often present in inflammatory skin diseases, conditions or disorders. As used herein, the term "hyper proliferation" may in some embodiments be termed "proliferation" having all the same qualities and meanings. In one embodiment, a method of this invention comprises reducing or inhibiting keratinocyte proliferation in a human subject, comprising the step of administering to the subject a therapeutically effective amount of a composition comprising a nucleic acid molecule that comprises a nucleic acid molecule comprising a nucleic acid sequence that is at least 80% identical to an miRNA sequence, or wherein the nucleic acid sequence expresses a ribonucleic acid sequence that is at least 80% identical to an miRNA sequence.

Thus, compositions and methods of the present invention can be used to reduce and/or inhibit keratinocyte proliferation, wherein the reduction and or/inhibition of keratinocyte proliferation, in one embodiment, treats, prevents, reduces the severity of, reduces the incidence of, delays the onset of, or reduces pathogenesis of an inflammatory skin disease, or any combination thereof. In another embodiment, reduction and or/inhibition of keratinocyte proliferation, treats, prevents, reduces the severity of, reduces the incidence of, delays the onset of, or reduces pathogenesis of at least one symptom of an inflammatory skin disease. These embodiments are not exclusive. Each possibility represents a separate embodiment of the present invention.

In one embodiment, a method of this invention treating, reducing the severity of, reducing the incidence of, delaying the onset of, or reducing pathogenesis of the inflammatory skin disease, condition or lesion, reduces the number of lesions, reduces the size of the lesions, reduces the spread of lesions, or reduces the depth of the lesions, or any combination thereof. Each possibility represents a separate embodiment of the present invention. As used herein, the term "lesions" refers in one embodiment to any abnormality in the tissue of an organism usually caused by disease or trauma. For example abnormalities in and on the skin caused by inflammatory skin diseases. In certain embodiments, lesions are psoriatic lesions. In one embodiment, a method of this invention promotes healing of lesions. In certain embodiments, a lesion involves a break or wound to the skin. In some embodiments, lesions on the skin comprise wounds, open sores, cuts, deep scrapes or puss-filled gashes. In one embodiment, a method of this invention promotes wound healing.

Inflammatory skin disease lesions may be either asymptomatic or pruritic and are most often localized on the scalp, extensor surfaces of the elbows and knees, sacrum, buttocks (commonly the gluteal cleft), and genitals. The nails, eyebrows, axillae, umbilicus, and perianal region may also be affected. The disease can be widespread, involving confluent areas of skin extending between these regions. Lesions differ in appearance depending on type.

Psoriasis typically affects the outside of the elbows, knees or scalp, though it can appear on any location. In one embodiment, a method of this invention to directed to an outside surface of skin. In one embodiment, an outside surface of the skin includes but is not limited to an elbow, a knew, a hand, a finger a leg, a foot, a face, a nail, a genital or scalp, or any combination thereof. Each possibility represents a separate embodiment of the present invention. Psoriatic lesions, for example those observed in plaque psoriasis (psoriasis vulgaris or chronic plaque psoriasis) may be discrete, erythematous papules or plaques covered with thick, silvery, shiny scales. Lesions appear gradually and remit and recur spontaneously or with the appearance and resolution of triggers. Thus, in one embodiment, methods of this invention reduce and or inhibit the reoccurrence of lesions present in an inflammatory skin disease.

In one embodiment, an miRNA of this invention is selected from those differentially expressed in an inflammatory skin disease. In one embodiment, an miRNA of this invention is selected from those differentially expressed in psoriatic skin lesions. In one embodiment, an miRNA has reduced expression in psoriatic skin lesions, compared with normal skin.

The present invention discloses methods of using compositions comprising at least one miRNA for treating a variety of diseases with an inflammatory skin component, for example psoriasis, (hereinafter collectively referred to as "inflammatory skin diseases" or "conditions associated with an inflammatory skin disease") or other similar phrases. In one embodiment, the present invention provides a method of treating pathological conditions resulting from increased keratinocyte proliferation comprising administration of an effective amount of a composition comprising an at least one miRNA. In one embodiment, the present invention provides methods of treating symptoms associated with inflammatory skin conditions.

Nucleic Acid Molecules

As used herein, the term "miRNA" refers, in one embodiment, to a microRNA molecule found in eukaryotes that is involved in RNA-based gene regulation. In some embodiments, "miRNA" refers to the single-stranded RNA molecule processed from a precursor, wherein the processed miRNA may be the final mature miRNA molecule. In other embodiments, an miRNA of this invention may be an miRNA molecule having a nucleic acid sequence less than that of a precursor miRNA and more than that of a mature miRNA. In one embodiment, an miRNA of this invention may be a precursor miRNA (pre-miRNA). Pre-miRNA molecules known in the art are about 60-70 nucleotides long and include stem and loop sequences, wherein in their native configuration they form a stem loop structure. Pre-miRNA molecules may be processed to form mature miRNA molecules of about 22 nucleotides. In one embodiment, an miRNA may be a mature miRNA. In one embodiment, an miRNA may be double stranded and include both miRNA products, the miRNA-5p strand and its miRNA-3p strand, (miRNA*). A double stranded miRNA may comprise a stem loop structure containing the two miRNAs, one on each side of the stem, wherein the sequences of the two sides of the stem is always, only partially complementary. In one embodiment, an miRNA of this invention is a human miRNA.

As used throughout, the term "miRNA" may be used interchangeably with "MiRNA", "miR", "mir" or "MiR" having all the same meanings and qualities.

In certain embodiments, nucleic acid molecules of this invention will include an miRNA and may additionally encompass a region or an additional strand that is partially (between 10 and 50% complementary across length of strand), substantially (greater than 50% but less than 100% complementary across length of strand) or fully complementary to another region of the same single-stranded molecule or to another nucleic acid. Thus, miRNA nucleic acids may encompass a molecule that comprises one or more complementary or self-complementary strand(s) or "complement(s)" of a particular sequence. For example, precursor miRNA may have a self-complementary region, which is up to 100% complementary. miRNA probes or nucleic acids of the invention can include, can be or can be at least 60, 65, 70, 75, 80, 85, 90, 95, 96, 97, 98, 99 or 100% complementary to their target.

A composition comprising a nucleic acid molecule comprising a nucleic acid sequence comprising an miRNA may be administered wherein the miRNA is not a mature miRNA but is capable of becoming or functioning as a mature miRNA under the appropriate physiological conditions. Administration of a therapeutically effective amount of a composition comprising a nucleic acid comprising a nucleic acid sequence comprising an miRNA or comprising a nucleic acid sequence expressing an miRNA may, in some embodiments, treat, prevent, reduce the severity of, reduce the incidence of, reduce the spread of, delay the onset of, reduce the pathogenesis of an inflammatory skin disease or condition with minimal adverse effect to a subject. In one embodiment, the inflammatory skin disease or condition is psoriasis.

Nucleic acid molecules of this invention may in certain embodiments include naturally occurring nucleic acids, modified nucleic acids, nucleic acid mimetics, miRNAs, and segments thereof that can be employed in therapeutic applications, particularly those applications related to pathogenesis of inflammatory skin conditions. The molecules may have been endogenously produced by a cell and isolated, or synthesized or produced chemically or recombinantly. They may be isolated and/or purified. Each possibility represents a separate embodiment of the present invention.

Each of the miRNAs described herein includes the corresponding SEQ ID NO and accession numbers for these miRNA sequences. The name of a miRNA is often abbreviated and referred to without a "hsa-" prefix and will be understood as such, depending on the context, wherein the term "hsa-" refers to the source or sequence of the miRNA being human (*homo sapiens*). Unless otherwise indicated, miRNAs referred to in the application are human sequences identified as miR-X or mir-X or let-X or LetX, where X is a number(s) and/or letter(s).

In one embodiment, nucleic acids present within a nucleic acid molecule or an miRNA sequence may be synthetic or non-synthetic nucleic acids. As used herein, the term "synthetic nucleic acid" refers in one embodiment to a nucleic acid that does not have a chemical structure or sequence of a naturally occurring nucleic acid. As used herein, the term "synthetic miRNA" refers in one embodiment, to a "synthetic nucleic acid" that functions in a cell or under physiological conditions as a naturally occurring miRNA.

While embodiments of the invention may involve synthetic miRNAs or synthetic nucleic acids, in some embodiments of the invention, the nucleic acid molecule(s) need not be "synthetic." In certain embodiments, a non-synthetic nucleic acid or miRNA employed in methods and compositions of the invention may have the entire sequence and structure of a naturally occurring mRNA or miRNA precursor or the mature mRNA or miRNA. For example, non-synthetic miRNAs used in methods and compositions of the invention may not have one or more modified nucleotides or nucleotide analogs. In these embodiments, the non-synthetic miRNA may or may not be recombinantly produced. Any embodiments discussed with respect to the use of synthetic miRNAs can be applied with respect to non-synthetic miRNAs, and vice versa.

As used herein, the term "naturally occurring" refers in one embodiment, to something found in an organism without any intervention by a person; it could refer to a naturally-occurring wild-type or mutant molecule. In some embodiments a synthetic miRNA molecule does not have the sequence of a naturally occurring miRNA molecule. In other embodiments, a synthetic miRNA molecule may have the sequence of a naturally occurring miRNA molecule, but the chemical structure of the molecule, particularly in the part unrelated specifically to the precise sequence (non-sequence chemical structure) differs from chemical structure of the naturally occurring miRNA molecule with that sequence. In some cases, the synthetic miRNA has both a sequence and non-sequence chemical structure that are not found in a naturally-occurring miRNA. Moreover, the sequence of the synthetic molecules will identify which miRNA is effectively being provided; the endogenous miRNA will be referred to as the "corresponding miRNA." Corresponding miRNA sequences that can be used in the context of the invention include, but are not limited to, all or a portion of those sequences in the SEQ IDs provided herein, as well as any other miRNA sequence, miRNA precursor sequence, or any sequence complementary thereof. In some embodiments, the sequence is or is derived from or contains all or part of a sequence identified herein to target a particular miRNA (or set of miRNAs) that can be used with that sequence.

In some embodiments, an miRNA designated by a suffix "5P" or "3P" can be used. "5P" indicates that the mature miRNA derives from the 5' end of the precursor and a corresponding "3P" indicates that it derives from the 3' end of the precursor, as described on the world-wide-web at sanger.ac.uk. Moreover, in some embodiments, a miRNA molecule of this invention does not correspond exactly to a known human miRNA. In one embodiment, these non-human miRNA molecules may be used in embodiments of the invention.

In one embodiment, an amount of a composition comprising a nucleic acid molecule administered is an "effective amount" or a "therapeutically effective amount" or an "amount sufficient" for a particular result, which refers to an amount needed (or a sufficient amount) to achieve a desired goal, such as inducing a particular cellular characteristic(s). For example, in one embodiment a therapeutically effective amount of a composition comprising a nucleic acid molecule of this invention treats, prevents, reduces the severity of, reduces the incidence of, delays the onset of, reducing the spread of or reduces pathogenesis of an inflammatory skin disease. In another embodiment, a therapeutically effective amount of a composition of this invention reduces at least one symptom of an inflammatory skin lesion or disease. In yet another embodiment, therapeutically effective amount of a composition of this invention reduces or inhibits keratinocyte proliferation. As used herein, the term "composition" refers in one embodiment to a composition comprising a nucleic acid comprising an miRNA. In another embodiment, a composition comprises a vector comprising a nucleic acid molecule comprising an miRNA. In yet another embodiment, a composition comprises a nucleic acid molecule expressing an miRNA. In still another embodiment, a composition comprises a vector comprising a nucleic acid molecule expressing an miRNA. In some embodiments, the composition may be referred to as an "miRNA composition" having all the same meanings and qualities.

In another embodiment a therapeutically effective amount of a composition comprising a nucleic acid molecule comprising an miRNA treats, prevents, reduces the severity of, reduces the incidence of, delays the onset of, reducing the spread of or reduces pathogenesis of an inflammatory skin disease. In yet another embodiment, a therapeutically effective amount of a composition of this invention comprising a nucleic acid molecule comprising an miRNA reduces at least one symptom of an inflammatory skin lesion or disease. In still another embodiment, therapeutically effective amount of a composition comprising a nucleic acid comprising an miRNA reduces or inhibits keratinocyte proliferation. In a further embodiment, a therapeutically effective amount of a composition comprising a nucleic acid molecule that expresses an miRNA treats, prevents, reduces the severity of, reduces the incidence of, delays the onset of, reducing the spread of or reduces pathogenesis of an inflammatory skin disease. In another embodiment, a therapeutically effective amount of a composition of this invention comprising a nucleic acid molecule that expresses an miRNA reduces at least one symptom of an inflammatory skin lesion or disease. In still another embodiment, therapeutically effective amount of a composition comprising a nucleic acid that expresses an miRNA reduces or inhibits keratinocyte proliferation. In one embodiment, an miRNA sequence of this invention has reduced expression in psoriatic skin lesions compared with expression in normal skin (Example 7). Each possibility represents a separate embodiment of the present invention.

In certain embodiments, the methods include providing or introducing to a cell a nucleic acid molecule corresponding to a mature miRNA in the cell in an amount effective to achieve a desired physiological result. Moreover, methods can involve providing synthetic or nonsynthetic miRNA molecules. In certain embodiments, synthetic miRNA of the invention include RNA or RNA analogs.

The present invention, in some embodiments, includes use of short nucleic acid molecules that function as miRNAs in a cell. The term "short" refers to a length of a single polynucleotide that is at least, at most, or about 6, 7, 8, 9, 10, 11, 12, 13, 14, 15, 16, 17, 18, 19, 20, 21, 22, 23, 24, 25, 50, 100, or 150 nucleotides, including all integers or ranges derivable there between. The nucleic acid molecules are typically synthetic. In certain aspects the sequence (the entire sequence) and/or chemical structure deviates from a naturally-occurring nucleic acid molecule, such as an endogenous precursor miRNA or miRNA molecule or complement thereof. While in some embodiments, nucleic acids of the invention do not have an entire sequence that is identical or complementary to a sequence of a naturally-occurring nucleic acid, such molecules may encompass all or part of a naturally-occurring sequence or a complement thereof. In some embodiments, a synthetic nucleic acid administered to a subject may subsequently be modified or altered in the cells of the subject such that its structure or sequence is the same as non-synthetic or naturally occurring nucleic acid, such as a mature miRNA sequence. For example, a synthetic nucleic acid may have a sequence that differs from the sequence of a precursor miRNA, but that sequence may be altered once in a cell to be the same as an endogenous, processed miRNA.

The term "isolated" means that the nucleic acid molecules of the invention may initially be separated from different (in terms of sequence or structure) from unwanted nucleic acid molecules such that a population of isolated nucleic acids is at least about 80% homogenous, and may be at least about 85%, 87%, 90%, 95, 96, 97, 98, 99, or 100% homogenous with respect to other polynucleotide molecules. In many embodiments of the invention, a nucleic acid molecule is isolated by virtue of it having been synthesized in vitro separate from endogenous nucleic acids. In certain embodiments, isolated nucleic acids may be subsequently mixed or pooled together. In one embodiment, a nucleic acid molecule comprises a nucleic acid sequence of an miRNA sequence. In another embodiment, a nucleic acid molecule comprises a nucleic acid sequence comprising at least two miRNA sequences. In yet another embodiment, a nucleic acid molecule comprises a nucleic acid sequence comprising at least three miRNA sequences. In still another embodiment, a nucleic acid molecule comprises a nucleic acid sequence comprising at least four miRNA sequences.

In one embodiment, an miRNA sequence comprises a pre-miR-197 [SEQ ID NO: 9](NCBI Reference Sequence No.: NR_029583; miRBase (www.mirbase.org) Reference No.: MI0000239), or mature miR-197-3p [SEQ ID NO: 8] (NCBI Reference Sequence No.: AJ560754; miRBase (www.mirbase.org) Reference No.: MIMAT0000227) or pre-miR-99a [SEQ ID NO: 16] (NCBI Reference Sequence No.: NR_029514; miRBase (www.mirbase.org) Reference No.: MI0000101), or mature miR-99a-5p [SEQ ID NO: 17] (miRBase (www.mirbase.org) Reference No.: MIMAT0000097), or pre-Let7c [SEQ ID NO: 12] (NCBI Reference Sequence No.: NR_029480; miRBase (www.mirbase.org) Reference No.: MI0000064), or mature Let7c-5p [SEQ ID NO: 13] (miRBase (www.mirbase.org) Reference No.: MIMAT0000064), or pre-miR-125b-2 [SEQ ID NO: 14] (miRBase (www.mirbase.org) Reference No.: MI0000470), or mature miR-125b-2-5p [SEQ ID NO: 15] (miRBase (www.mirbase.org) Reference No.: MIMAT0000423), or a mature-miR-423 [SEQ ID NO: 19] (hsa-miR-423-3p MIMAT0001340), or a pre-miRNA miR-423 [SEQ ID NO: 18] (hsa-mir-423 MI0001445), or a mature-miR-150 [SEQ ID NO: 21 (hsa-miR-150-5p MIMAT0000451); SEQ ID NO: 22 (hsa-miR-150-3p MIMAT0004610)], or a pre-miRNA miR-150 [SEQ ID NO: 20] (hsa-mir-150 MI0000479), or any combination thereof. In another embodiment, an miRNA sequence of the methods described here comprises any precursor miRNA down-regulated in psoriatic skin lesions, or any mature miRNA down-regulated in psoriatic skin lesions, or any combination thereof. In one embodiment, an miRNA sequence comprises a pre-miR-197 [SEQ ID NO: 9]. In one embodiment, an miRNA sequence comprises a mature miR-197 [SEQ ID NO: 8]. In one embodiment, an miRNA sequence comprises a pre-miR-99a [SEQ ID NO: 16]. In one embodiment, an miRNA sequence comprises a mature miR-99a [SEQ ID NO: 17] In one embodiment, an miRNA sequence comprises a pre-Let7c [SEQ ID NO: 12]. In one embodiment, an miRNA sequence comprises a mature Let7c [SEQ ID NO: 13]. In one embodiment, an miRNA sequence comprises a pre-miR-125b-2 [SEQ ID NO: 14]. In one embodiment, an miRNA sequence comprises a mature miR-125b-2 [SEQ ID NO: 15]. In one embodiment, an miRNA sequence comprises any precursor miRNA down-regulated in psoriatic skin lesions. In one embodiment, an miRNA sequence comprises any mature miRNA down-regulated in psoriatic skin lesions.

In one embodiment, an miRNA sequence of this invention comprises a combination of miRNA sequences. In one embodiment, administration of an miRNA sequence of this invention inhibits keratinocyte proliferation. In one embodiment, administration of an miRNA sequence of this invention inhibits keratinocyte migration. Each possibility represents a separate embodiment of the present invention.

In some embodiments, there is an miRNA or a synthetic miRNA having a length of between 10 and 130 residues. The present invention concerns miRNA or synthetic miRNA molecules that are, are at least, or are at most 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 140, 145, 150, 160, 170, 180, 190, 200 or more nucleotides in length, including any integer or any range there between. In one embodiment, an mRNA comprises a sequence length of about of about 22 nucleotides wherein miRNA is mature miRNA, or about 60-120 nucleotides wherein miRNA is precursor miRNA.

In certain embodiments, synthetic miRNA have (a) a "miRNA region" whose sequence or binding region from 5' to 3' is identical or complementary to all or a segment of a mature miRNA sequence, and (b) a "complementary region" whose sequence from 5' to 3' is between 60% and 100% complementary to the miRNA sequence in (a). In certain embodiments, these synthetic miRNA are also isolated. The term "miRNA region" or complement thereof refers to a region on the synthetic miRNA that is at least 75, 80, 85, 90, 95, or 100% identical, including all integers there between, to the entire sequence of a mature, naturally occurring miRNA sequence or a complement thereof. In certain embodiments, the miRNA sequence is or is at least 70, 75, 80, 85, 87, 90, 91, 92, 93, 94, 95, 96, 97, 98, 99, 99.1, 99.2, 99.3, 99.4, 99.5, 99.6, 99.7, 99.8, 99.9 or 100% identical to the sequence of a naturally-occurring miRNA or complement thereof. In certain embodiments, a double stranded RNA can comprise a miRNA sequence that is 70 to 100%, 70%, 75%, 80%, 85%, 87%, 90%, 92%, 95%, 97%, or 100% identical to sequences described herein, for example as described directly above miRNA sequences down regulated is psoriatic skin lesions.

In certain embodiments, a nucleic acid molecule of this invention is a ribonucleic acid (RNA) encoding an miRNA sequence. In other embodiments, a nucleic acid molecule is an RNA encoding a complementary miRNA sequence. In one embodiment, a nucleic acid molecule is a double stranded RNA including an miRNA and its complementary strand. In an alternative embodiment, a nucleic acid molecule of this invention is a deoxyribonucleic acid (DNA) encoding at least an miRNA sequence. In another embodiment, a nucleic acid molecule of this invention is a DNA encoding at least a complementary miRNA* sequence. In one embodiment, a nucleic acid molecule is a DNA encoding at least an miRNA and its complementary miRNA* sequence. In one embodiment, a nucleic acid molecule is single stranded. In another embodiment, a nucleic acid molecule is double stranded. In yet another embodiment, a nucleic acid molecule is single stranded yet is configured to include double stranded regions, for example stems with hairpin turns.

The term "complementary region" or "complement" refers to a region of a nucleic acid or mimetic that is or is at least 60% complementary to the mature, naturally occurring miRNA sequence. The complementary region can be at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9 or 100% complementary including all values and ranges there between. With single polynucleotide sequences, there may be a hairpin loop structure as a result of chemical bonding between the miRNA region and the complementary region. In other embodiments, the complementary region is on a different nucleic acid molecule than the miRNA region, in which case the complementary region is on the complementary strand and the miRNA region is on the active strand.

In some embodiments of the invention a synthetic miRNA contains one or more design element(s). These design elements include, but are not limited to: (i) a replacement group for the phosphate or hydroxyl of the nucleotide at the 5' terminus of the complementary region; (ii) one or more sugar modifications in at least one residue of the complementary region; or, (iii) noncomplementarity between one or more nucleotides in the 3' end of the complementary region and the corresponding nucleotides of the miRNA region. A variety of design modifications are known in the art.

In certain embodiments, a synthetic miRNA has a nucleotide at its 5' end of the complementary region in which the phosphate and/or hydroxyl group has been replaced with another chemical group (referred to as the "replacement design"). In some cases, the phosphate group is replaced, while in others, the hydroxyl group has been replaced. In particular embodiments, the replacement group is biotin, an amine group, a lower alkylamine group, an acetyl group, 2'O-Me (2' oxygen-methyl), DMTO (4,4'-dimethoxytrityl with oxygen), fluoroscein, a thiol, or acridine, though other replacement groups are well known to those of skill in the art and can be used as well.

Additional embodiments concern a synthetic miRNA having one or more sugar modifications at least one of its residues of the complementary region (referred to as the "sugar replacement design"). In certain cases, there is one or more sugar modifications in the first 1, 2, 3, 4, 5, 6 or more residues of the complementary region, or any range derivable therein. In additional cases, there are one or more sugar modifications in the last 1, 2, 3, 4, 5, 6 or more residues of the complementary region, or any range derivable therein, have a sugar modification. It will be understood that the terms "first" and "last" are with respect to the order of residues from the 5' end to the 3' end of the region. In particular embodiments, the sugar modification is a 2'O-Me modification, a 2° F. modification, a 2'H modification, a 2'amino modification, a 4'thioribose modification or a phosphorothioate modification on the carboxy group linked to the carbon at position 6'. In further embodiments, there are one or more sugar modifications in the first or last 2 to 4 residues of the complementary region or the first or last 4 to 6 residues of the complementary region.

In other embodiments of the invention, there is a synthetic miRNA in which one or more nucleotides in the last 1 to 5 residues at the 3' end of the complementary region are not complementary to the corresponding nucleotides of the miRNA region ("noncomplementarity") (referred to as the "noncomplementarity design"). The noncomplementarity may be in the last 1, 2, 3, 4, and/or 5 residues of the complementary miRNA. In certain embodiments, there is noncomplementarity with at least 2 nucleotides in the complementary region.

In some embodiments, synthetic miRNA of the invention have one or more of the replacement, sugar modification, or noncomplementarity designs. In certain cases, synthetic RNA molecules have two of them, while in others these molecules have all three designs in place. Each possibility represents a separate embodiment of the present invention.

The miRNA region and the complementary region may be on the same or separate polynucleotides. In cases in which they are contained on or in the same polynucleotide, the miRNA molecule will be considered a single polynucleotide. In embodiments in which the different regions are on separate polynucleotides, the synthetic miRNA will be considered to be comprised of two polynucleotides.

When the RNA molecule is a single polynucleotide, there can be a linker region between the miRNA region and the complementary region. In some embodiments, the single polynucleotide is capable of forming a hairpin loop structure as a result of bonding between the miRNA region and the complementary region. The linker constitutes the hairpin loop. It is contemplated that in some embodiments, the linker region is, is at least, or is at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 residues in length, or any range derivable therein. In certain embodiments, the linker is between 3 and 30 residues (inclusive) in length.

In addition to having a miRNA region and a complementary region, there may be flanking sequences as well at either the 5' or 3' end of the region. In some embodiments, there is or is at least 1, 2, 3, 4, 5, 6, 7, 8, 9, 10 nucleotides or more, or any range derivable therein, flanking one or both sides of these regions.

In some embodiments of the invention, methods and compositions involving miRNA may concern nucleic acids comprising miRNA nucleotide sequences. Nucleic acid molecules may be, be at least, or be at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides, or any range derivable therein, in length. Such lengths cover the lengths of processed miRNA, precursor miRNA, miRNA containing vectors, and therapeutic miRNA. In many embodiments, miRNA are about 14-35 nucleotides in length. In other embodiments, miRNA are about 20-24 nucleotides in length. In one embodiment, miRNA are about 20 nucleotides in length. In another embodiment, miRNA are about 21 nucleotides in length. In another embodiment, miRNA are about 22 nucleotides in length. In another embodiment, miRNA are about 23 nucleotides in length. In another embodiment, miRNA are about 24 nucleotides in length.

In some embodiments, nucleic acids are derived from genomic sequences or a gene. In this respect, the term "gene" is used for simplicity to refer to the genomic sequence encoding the precursor nucleic acid or miRNA for a given miRNA or gene. However, embodiments of the invention may involve genomic sequences of a miRNA that are involved in its expression, such as a promoter or other regulatory sequences.

The term "recombinant" as used herein refers in one embodiment, to a molecule that has been manipulated in vitro or that is a replicated or expressed product of such a molecule.

The term "nucleic acid" is well known in the art. As used herein, the term "nucleic acid" refer to a molecule (one or more strands) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompasses the terms "oligonucleotide" and "polynucleotide," each as a subgenus of the term "nucleic acid."

As known in the art, the building blocks of nucleic acid molecules may include nucleobases, nucleosides, nucleotides and modified nucleotides.

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in a manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, carboxyalkyl, amino, hydroxyl, halogen (i.e., fluoro, chloro, bromo, or iodo), thiol or alkylthiol moiety. Alkyl (e.g., alkyl, carboxyalkyl, etc.) moieties may comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-diemethyladenine, an azaadenines, a 8-bromoadenine, a 8-hydroxyadenine, a 6-hydroxyaminopurine, a 6-thiopurine, a 4-(6-aminohexyl/cytosine), and the like. Other examples are well known to those of skill in the art.

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring. Different types of covalent attachment(s) of a nucleobase to a nucleobase linker moiety are known in the art.

As used herein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

A nucleic acid may comprise, or be composed entirely of, a derivative or analog of a nucleobase, a nucleobase linker moiety and/or backbone moiety that may be present in a naturally occurring nucleic acid. RNA with nucleic acid analogs may also be labeled according to methods of the invention. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art.

Labeling methods contemplate the use of nucleotides that are both modified for attachment of a label and can be incorporated into a miRNA molecule. Such nucleotides include those that can be labeled with a dye, including a fluorescent dye, or with a molecule such as biotin. Labeled nucleotides are readily available; they can be acquired commercially or they can be synthesized by reactions known to those of skill in the art.

Modified nucleotides for use in the invention are not naturally occurring nucleotides, but instead, refer to prepared nucleotides that have a reactive moiety on them. Specific reactive functionalities of interest include: amino, sulfhydryl, sulfoxyl, aminosulfhydryl, azido, epoxide, isothiocyanate, isocyanate, anhydride, monochlorotriazine, dichlorotriazine, mono- or dihalogen substituted pyridine, mono- or disubstituted diazine, maleimide, epoxide, aziridine, sulfonyl halide, acid halide, alkyl halide, aryl halide, alkylsulfonate, N-hydroxysuccinimide ester, imido ester, hydrazine, azidonitrophenyl, azide, 3-(2-pyridyl dithio)-propionamide, glyoxal, aldehyde, iodoacetyl, cyanomethyl ester, p-nitrophenyl ester, o-nitrophenyl ester, hydroxypyridine ester, carbonyl imidazole, and the other such chemical groups. In some embodiments, the reactive functionality may be bonded directly to a nucleotide, or it may be bonded to the nucleotide through a linking group. The functional moiety and any linker cannot substantially impair the ability of the nucleotide to be added to the miRNA or to be labeled. Representative linking groups include carbon containing linking groups, typically ranging from about 2 to 18, usually from about 2 to 8 carbon atoms, where the carbon containing linking groups may or may not include one or more heteroatoms, e.g. S, O, N etc., and may or may not include one or more sites of unsaturation. Of particular interest in many embodiments is alkyl linking groups, typically lower alkyl linking groups of 1 to 16, usually 1 to 4 carbon atoms, where the linking groups may include one or more sites of unsaturation. The functionalized nucleotides (or primers) used in the above methods of functionalized target generation may be fabricated using known protocols or purchased from commercial vendors, e.g., Sigma, Roche, Ambion, Biosearch Technologies and NEN. Functional groups may be prepared according to ways known to those of skill in the art.

The amine-modified nucleotide is a nucleotide that has a reactive amine group for attachment of the label. It is contemplated that any ribonucleotide (G, A, U, or C) or deoxyribonucleotide (G, A, T, or C) can be modified for labeling. Examples include, but are not limited to, the following modified ribo- and deoxyribo-nucleotides: 5-(3-aminoallyl)-UTP; 8-[(4-amino)butyl]-amino-ATP and 8-[(6-amino)butyl]-amino-ATP; N6-(4-amino)butyl-ATP, N6-(6-amino)butyl-ATP, N4-[2,2-oxy-bis-(ethylamine)]-CTP; N6-(6-Amino)hexyl-ATP; 8-[(6-Amino)hexyl]-amino-ATP; 5-propargylamino-CTP, 5-propargylamino-UTP; 5-(3-aminoallyl)-dUTP; 8-[(4-amino)butyl]-amino-dATP and 8-[(6-amino)butyl]-amino-dATP; N6-(4-amino)butyl-dATP, N6-(6-amino)butyl-dATP, N4-[2,2-oxy-bis-(ethylamine)]-dCTP; N6-(6-Amino)hexyl-dATP; 8-[(6-Amino)hexyl]-amino-dATP; 5-propargy lamino-dCTP, and 5-propargylamino-dUTP. Such nucleotides can be prepared according to methods known to those of skill in the art. Moreover, a person of ordinary skill in the art could prepare other nucleotide entities with the same amine-modification, such as a 5-(3-aminoallyl)-CTP, GTP, ATP, dCTP, dGTP, dTTP, or dUTP in place of a 5-(3-aminoallyl)-UTP.

A nucleic acid may be made by any technique known to one of ordinary skill in the art, such as for example, chemical synthesis, enzymatic production, or biological production. It is specifically contemplated that miRNA probes of the invention are chemically synthesized.

In some embodiments, nucleic acid molecules comprising miRNA sequences may be modified to increase the stability of an miRNA. In one embodiment stability of an miRNA within a cell is increased.

In some embodiments, miRNA molecules used in the methods of this invention may be synthesized by an outside provider, for example Sigma-Aldrich; Dharmacon Research, Inc.; Applied Biosystems; or Exiqon.

In some embodiments of the invention, miRNAs are recovered or isolated from a biological sample. The miRNA may be recombinant or it may be natural or endogenous to the cell (produced from the cell's genome). It is contemplated that a biological sample may be treated in a way so as to enhance the recovery of small RNA molecules such as miRNA. Generally, methods involve lysing cells with a solution having guanidinium and a detergent.

Alternatively, nucleic acid synthesis is performed according to standard methods. Non-limiting examples of a synthetic nucleic acid (e.g., a synthetic oligonucleotide), include a nucleic acid made by in vitro chemical synthesis using phosphotriester, phosphite, or phosphoramidite chemistry and solid phase techniques, or via deoxynucleoside H-phosphonate intermediates.

A non-limiting example of an enzymatically produced nucleic acid include one produced by enzymes in amplification reactions such as PCR™. See also Sambrook et al., 2001, incorporated herein by reference). Oligonucleotide synthesis is well known to those of skill in the art.

Recombinant methods for producing nucleic acids in a cell are well known to those of skill in the art. These include the use of vectors (viral and non-viral), plasmids, cosmids, and other vehicles for delivering a nucleic acid to a cell, which may be the target cell (e.g., a cancer cell) or simply a host cell (to produce large quantities of the desired RNA molecule). Alternatively, such vehicles can be used in the context of a cell free system so long as the reagents for generating the RNA molecule are present. Such methods include those described in Sambrook, 2003, Sambrook, 2001 and Sambrook, 1989, which are hereby incorporated by reference.

Nucleic acids may be isolated using techniques well known to those of skill in the art, though in particular embodiments, methods for isolating small nucleic acid molecules, and/or isolating RNA molecules can be employed. Chromatography is a process often used to separate or isolate nucleic acids from protein or from other nucleic acids. Such methods can involve electrophoresis with a gel matrix, filter columns, alcohol precipitation, and/or other chromatography. If miRNA from cells is to be used or evaluated, methods generally involve lysing the cells with a chaotropic (e.g., guanidinium isothiocyanate) and/or detergent (e.g., N-lauroyl sarcosine) prior to implementing processes for isolating particular populations of RNA.

In particular methods for separating miRNA from other nucleic acids, a gel matrix is prepared using polyacrylamide, though agarose can also be used. The gels may be graded by concentration or they may be uniform. Plates or tubing can be used to hold the gel matrix for electrophoresis. Usually one-dimensional electrophoresis is employed for the separation of nucleic acids. Plates are used to prepare a slab gel, while the tubing (glass or rubber, typically) can be used to prepare a tube gel. The phrase "tube electrophoresis" refers to the use of a tube or tubing, instead of plates, to form the gel. Materials for implementing tube electrophoresis can be readily prepared by a person of skill in the art or purchased, such as from C.B.S. Scientific Co., Inc. or Scie-Plas.

Methods may involve the use of organic solvents and/or alcohol to isolate nucleic acids, particularly miRNA used in methods and compositions of the invention. In general, methods for efficiently isolating small RNA molecules from cells comprising: adding an alcohol solution to a cell lysate and applying the alcohol/lysate mixture to a solid support before eluting the RNA molecules from the solid support. In some embodiments, the amount of alcohol added to a cell lysate achieves an alcohol concentration of about 55% to 60%. While different alcohols can be employed, ethanol works well. A solid support may be any structure, and it includes beads, filters, and columns, which may include a mineral or polymer support with electronegative groups. A glass fiber filter or column has worked particularly well for such isolation procedures.

In some embodiments, miRNA isolation processes include: (a) lysing cells in the sample with a lysing solution comprising guanidinium, wherein a lysate with a concentration of at least about 1 M guanidinium is produced; (b) extracting miRNA molecules from the lysate with an extraction solution comprising phenol; (c) adding to the lysate an alcohol solution for forming a lysate/alcohol mixture, wherein the concentration of alcohol in the mixture is between about 35% to about 70%; (d) applying the lysate/alcohol mixture to a solid support; (e) eluting the miRNA molecules from the solid support with an ionic solution; and, (f) capturing the miRNA molecules. Typically the sample is dried and resuspended in a liquid and volume appropriate for subsequent manipulation.

miRNA Based Therapy

Embodiments of the invention concern nucleic acids that perform the activities of endogenous miRNAs when introduced into cells. In certain embodiments, nucleic acids are synthetic or non-synthetic miRNA. Sequence-specific miRNA can be used to regulate sequentially or in combination the activities of one or more endogenous mRNAs in cells. In one embodiment, miRNAs of this invention up-regulate an activity of one or more endogenous mRNAs. In another embodiment, miRNAs of this invention down-regulate an activity of one or more endogenous mRNAs. In still another embodiment, an miRNA of this invention may up-regulate activity of at least one endogenous mRNA and down-regulate activity of at least one other endogenous mRNA.

Methods of the invention include supplying the activity of one or more miRNAs to a cell. Embodiments of the invention may include inducing certain cellular characteristics, such as reduced or inhibited keratinocyte proliferation, by providing to a cell a particular nucleic acid molecule that comprises a specific miRNA or expresses a specific miRNA. However, in methods of the invention, the miRNA molecule may be an isolated version of the miRNA, a recombinant miRNA, or a synthetic miRNA, or part of a longer nucleic acid sequence. In addition, in some embodiments, methods of this invention include use of compositions comprising miRNA to evaluate treatment efficacy of an inflammatory skin disease. In one embodiment, a method of this invention includes use of a composition comprising an miRNA to evaluated treatment efficacy of psoriasis.

Nucleic acids comprising miRNA may comprise a sequence that is identical to a naturally occurring miRNA or they may have design modifications. In other embodiments, miRNAs may comprise a sequence 75%, 80%, 85%, 90%, 91%, 92%, 93%, 94%. 95%, 96%, 97%, 98% or 99% identical to a naturally occurring miRNA. In alternate embodiments, nucleic acids expressing an miRNA may express a sequence that is identical to a naturally occurring miRNA or they may have design modifications. In other embodiments, nucleic acids expressing an miTNA may express a sequence comprising 75%, 80%, 85%, 90%, 91%, 92%, 93%, 94%. 95%, 96%, 97%, 98% or 99% identity to a naturally occurring miRNA.

Nucleic acids consisting essentially of an miRNA may consist essentially of a sequence that is identical to a naturally occurring miRNA or they may have design modifications. In other embodiments, miRNAs may consist essentially of a sequence 75%, 80%, 85%, 90%, 91%, 92%, 93%, 94%. 95%, 96%, 97%, 98% or 99% identical to a naturally occurring miRNA. In alternate embodiments, nucleic acids expressing an miRNA may express a sequence that is identical to a naturally occurring miRNA or they may have design modifications. In other embodiments, nucleic acids expressing an miRNA may express a sequence consisting essentially of 75%, 80%, 85%, 90%, 91%, 92%, 93%, 94%. 95%, 96%, 97%, 98% or 99% identity to a naturally occurring miRNA.

Nucleic acids consist of an miRNA may consist of a sequence that is identical to a naturally occurring miRNA or they may have design modifications. In other embodiments, miRNAs may consist of a sequence 75%, 80%, 85%, 90%, 91%, 92%, 93%, 94%. 95%, 96%, 97%, 98% or 99% identical to a naturally occurring miRNA. In alternate embodiments, nucleic acids expressing an miRNA may express a sequence that is identical to a naturally occurring miRNA or they may have design modifications. In other embodiments, nucleic acids expressing an miRNA may express a sequence consisting of 75%, 80%, 85%, 90%, 91%, 92%, 93%, 94%. 95%, 96%, 97%, 98% or 99% identity to a naturally occurring miRNA.

In one embodiment, a miRNA molecule introduced into a cell is a mature miRNA. In another embodiment, an miRNA is not a mature miRNA but is capable of becoming or functioning as a mature miRNA under the appropriate physiological conditions. In some embodiments, multiple corresponding miRNAs may be used. An miRNA may have a minimal adverse effect on a subject or patient while supplying a sufficient therapeutic effect, such as amelioration of a condition, growth inhibition of a cell for example reduction or inhibition of keratinocyte proliferation, death of a targeted cell, alteration of cell phenotype or physiology, slowing of cellular growth, or inhibition of cell growth.

In one embodiment, the term "identity" refers to the relatedness of two nucleotide sequences on a nucleotide-by-nucleotide basis over a particular comparison window or segment. Thus, identity is defined as the degree of sameness, correspondence or equivalence between the same strands (either sense or antisense) of two DNA segments (or two amino acid sequences as described herein below). Percentage of sequence identity is calculated by comparing two optimally aligned sequences over a particular region, determining the number of positions at which the identical base or amino acid occurs in both sequences in order to yield the number of matched positions, dividing the number of such positions by the total number of positions in the segment being compared and multiplying the result by 100. Thus, two copies of exactly the same sequence have 100% identity, while sequences that are less highly conserved and have deletions, addition, or replacements have a lower degree of identity. Optimal alignment of sequences may be conducted by the algorithm of Smith & Waterman, Appl. Math. 2:482 (1981), by the algorithm of Needleman & Wunsch, J. Mol. Biol. 48:443 (1970), by the method of Pearson & Lipman, Proc. Natl. Acad. Sci. (USA) 85:2444 (1988) and by computer programs which implement the relevant algorithms (e.g., Clustal Macaw Pileup; Higgins et al., CABIOS. 5L151-153 (1989)), FASTDB (Intelligenetics), BLAST (National Center for Biomedical Information; Altschul et al., Nucleic Acids Research 25:3389-3402 (1997)), PILEUP (Genetics Computer Group, Madison, Wis.) or GAP, BEST-FIT, FASTA and TFASTA (Wisconsin. Genetics Software Package Release 7.0, Genetics Computer Group, Madison, Wis.). (See U.S. Pat. No. 5,912,120.) The two nucleotide sequences may differ by copy error difference that normally occurs during the replication of a nuclear DNA.

Methods include identifying a cell or patient in need of inducing those cellular characteristics. In one embodiment, "a therapeutically effective dose" or "a therapeutically effective amount", refers to the amount of a composition comprising an miRNA or encoding an miRNA, which results in a reduction in keratinocyte proliferation in a subject. In another embodiment, "a therapeutically effective dose" or "a therapeutically effective amount", refers to the amount of a composition comprising an miRNA or encoding an miRNA, which results in the inhibition of in keratinocyte proliferation in a subject. In one embodiment, reduction and/or inhibition of keratinocyte proliferation is localized to a specific area of treatment. In another embodiment, reduction and/or inhibition of keratinocyte proliferation is systematic.

In one embodiment, methods of this invention comprise introducing into or providing a subject, tissue, or cell an effective amount of a synthetic or non-synthetic miRNA molecule that corresponds to an miRNA sequence disclosed therein. In one embodiment, methods of this invention comprise introducing into or providing a subject, tissue, or cell an effective amount of a synthetic or a non-synthetic miRNA molecule that regulates expression of at least one mRNA within said subject or region of the subject receiving treatment. In one embodiment, methods of this invention comprise introducing into or providing a subject, tissue, or cell an effective amount of a synthetic or a non-synthetic miRNA molecule that reduces and/or inhibits keratinocyte proliferation in a subject or a region of a subject receiving treatment.

Certain embodiments of the invention include methods of treating a pathologic condition. In one aspect, the method comprises contacting a target cell with one or more nucleic acid, synthetic miRNA, or miRNA comprising at least one nucleic acid segment having all or a portion of a miRNA sequence. The segment may be 5, 6, 7, 8, 9, 10, 11, 12, 13, 14, 15, 16, 17, 18, 19, 20, 21, 22, 23, 24, 25, 30 or more nucleotides or nucleotide analog including all integers there between. In certain embodiments, one or more nucleotides of a nucleic acid can be modified. In one embodiment, methods of this invention include modulation of gene expression, or mRNA expression or function within a target subject, tissue, or cell.

Typically, an endogenous gene or mRNA is modulated in the cell. In particular embodiments, the nucleic acid sequence comprises at least one segment that is at least 70, 75, 80, 85, 90, 95, 96, 97, 98, 99, or 100% identical in nucleic acid sequence to one or more mRNA or gene sequence. Modulation of the expression or processing of an endogenous gene or mRNA can be through modulation of the processing of a mRNA, such processing including transcription, transportation and/or translation in a cell. In still other embodiments, a nucleic acid sequence can comprise a modified nucleic acid sequence. In certain aspects, one or more miRNA sequence may include or comprise a modified nucleobase or nucleic acid sequence.

It will be understood that embodiments of methods of this invention include providing a cell or other biological matter such as an organism (including patients or subjects) with an miRNA by administering to the cell or organism a nucleic acid molecule that functions as the corresponding miRNA once inside the cell or expressing an miRNA once inside the cell. In certain embodiments, it is specifically contemplated that the miRNA molecule provided to the biological matter is not a mature miRNA molecule but a nucleic acid molecule that can be processed into the mature miRNA once it is accessible to miRNA processing machinery. As used herein, the term "providing" an miRNA or nucleic acid encoding an miRNA or a composition comprising a nucleic acid encoding an miRNA or a composition comprising a vector comprising a nucleic acid comprising or encoding an miRNA, refers in on embodiment to "administering" the composition to a patient.

Pharmaceutical Compositions and Delivery Thereof

Methods of the present invention include the delivery of an effective amount of a miRNA or an expression construct encoding the same. An "effective amount" of the pharmaceutical composition, generally, is defined as that amount sufficient to detectably achieve a desired result, for example, to ameliorate, reduce, minimize or limit the extent of a disease or its symptoms, for example an inflammatory skin disease and symptoms thereof. Other more rigorous definitions may apply, including elimination, eradication or cure of disease or symptoms thereof. Each possibility represents a separate embodiment of the present invention.

In some embodiments, this invention provides methods of use which comprise administering a composition comprising the described miRNAs or nucleic acids comprising or encoding these miRNAs. As used herein, "pharmaceutical composition" means a composition comprising a "therapeutically effective amount" of the active ingredient, i.e. the miRNAs of this invention, together with a pharmaceutically acceptable carrier or diluent. A "therapeutically effective amount" as used herein refers to that amount which provides a therapeutic effect for a given condition and administration regimen. As used throughout, the term "composition" is used interchangeably with "pharmaceutical composition" having all the same meanings and qualities.

As used herein, the term "administering" refers to bringing a subject in contact with a composition comprising an miRNA or expressing an miRNA of the present invention. As used herein, "administration" can be accomplished in vivo, i.e. in cells or tissues of living organisms, for example humans. In one embodiment, administration comprises topical, sub-dermal, transdermal, enteral, parental or intravenous administration. In another embodiment, administration comprises injection or local injection at a target site.

In one embodiment, methods of this invention utilize a topical administration. In one embodiment topical administration comprises use of a cream, gel, ointment, spray, lip-balm, balm, emulsion, liposome, liquid crystal preparation or lotion, or any combination thereof. In one embodiment, topical administration includes the use technology to assist entry of the topical cream, gel, ointment, spray, lip-balm, emulsion, liposome, liquid crystal preparations or lotions. These delivery agents might be used in addition to physical aids for example ultrasound based technologies or special dressings. Each possibility represents a separate embodiment of the present invention.

Numerous standard references are available that describe procedures for preparing various formulations suitable for administering the miRNAs according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

Compositions comprising nucleic acids comprising an miRNA sequence ("miRNA compositions") can be introduced into the skin or other external tissues with agents that can facilitate uptake into epithelial cells using a variety of techniques that are available in the art. The term, "miRNA compositions", as used herein, in one embodiment refers to compositions comprising nucleic acids comprising an miRNA sequence. The term, "miRNA compositions", as used herein, in another embodiment refers to compositions comprising nucleic acids expressing an miRNA sequence. For example, miRNA compositions can be introduced into cells using mechanical methods, such as microinjection, liposome-mediated transfection, iontophoresis, or calcium phosphate precipitation. In some embodiments, the disclosed miRNA compositions are formulated in the form of a controlled release formulation or sustained release formulation administered topically or injected directly into the skin adjacent to or within the area to be treated (intradermally or subcutaneously). In certain embodiments, an area to be treated is a lesion from an inflammatory skin disease. In other embodiments, an area to be treated encompasses multiple lesions from an inflammatory skin disease. In one embodiment, an area to be treated is a psoriatic lesion. In another embodiment, an area to be treated includes multiple psoriatic lesions. In other embodiments, the disclosed miRNA compositions comprise vector systems for expression within cells following administration.

The mode of administration and dosage forms is closely related to the therapeutic amounts of the miRNA or miRNA compositions which are desirable and efficacious for the given treatment application.

To prepare such pharmaceutical dosage forms, the active ingredient, for example a nucleic acid or miRNA may be mixed with a pharmaceutical carrier according to conventional pharmaceutical compounding techniques. The carrier may take a wide variety of forms depending on the form of preparation desired for administration.

In some embodiments, miRNA compositions may comprise a condensing agent to form a nucleic acid delivery vehicle. Suitable polycations include, for example, polylysine, polyarginine, polyornithine, protamine, spermine, spermidine, and putrescine. Many suitable methods for making linkages between condensing agents and nucleic acids are known in the art.

In other embodiments, miRNA compositions may comprise a liposome to form a nucleic acid delivery vehicle. Liposomes are small, lipid vesicles comprised of an aqueous compartment enclosed by a lipid bilayer, typically spherical or slightly elongated structures several hundred angstroms in diameter. Under appropriate conditions, a liposome can fuse with the plasma membrane of a cell or with the membrane of an endocytic vesicle within a cell that has internalized the liposome, thereby releasing its contents into the cytoplasm. Prior to interaction with the surface of a cell, however, the liposome membrane acts as a relatively impermeable barrier that sequesters and protects its contents, for example, from degradative enzymes. Additionally, because a liposome is a synthetic structure, specially designed liposomes can be produced that incorporate desirable features.

Liposomal preparations include cationic (positively charged), anionic (negatively charged) and neutral preparations. Cationic liposomes have been shown to mediate intracellular delivery of plasmid DNA, mRNA, and purified transcription factors, in functional form. Cationic liposomes are readily available. For example, N[1-2,3-dioleyloxy)propyl]-N,N,N-triethylammonium (DOTMA) liposomes are available under the trademark Lipofectin™, (GIBCO BRL, Grand Island, N.Y.), Transfectace (DDAB/DOPE) and DOTAP/DOPE (Boerhinger). Other cationic liposomes can be prepared from readily available materials using techniques available in the art.

Similarly, anionic and neutral liposomes are readily available, such as from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), and dioleoylphoshatidyl ethanolamine (DOPE). These materials can also be mixed with the DOTMA and DOTAP starting materials in appropriate ratios. Methods for making liposomes using these materials are well known in the art.

The liposomes can comprise multilamellar vesicles (MLVs), small unilamellar vesicles (SUVs), or large unilamellar vesicles (LUVs). The various liposome-nucleic acid complexes are prepared using methods known in the art.

In addition, lipoproteins can be included with a nucleic acid for delivery to a cell. Examples of such lipoproteins include chylomicrons, HDL, IDL, LDL, and VLDL. Mutants, fragments, or fusions of these proteins can also be used. Modifications of naturally occurring lipoproteins can also be used, such as acetylated LDL. These lipoproteins can target the delivery of nucleic acids to cells expressing lipoprotein receptors. In some embodiments, if lipoproteins are included with a nucleic acid, no other targeting ligand is included in the composition. Receptor-mediated targeted delivery of miRNA compositions to specific tissues can also be used.

Controlled or sustained release can be achieved by the addition of time-release additives, such as polymeric structures, matrices, that are available in the art. An insert, transdermal patch, bandage or article used to deliver the disclosed miRNA compositions can comprise a mixture or coating of polymers that provide release of the active agents at a constant rate over a prolonged period of time.

In some embodiments, the article, transdermal patch, bandage or insert comprises water-soluble pore forming agents, such as polyethylene glycol (PEG) that can be mixed with water insoluble polymers to increase the durability of the insert and to prolong the release of the active ingredients. Such a water-soluble pore-forming agent can be polyethylene glycol, polypropylene glycol, a mixture or polymer of sugars (lactose, sucrose, dextrose, etc.), salts, poloxamers, hydroxypropylcellulose, polyvinyl alcohol and other water-soluble food grade and other excipients.

The inserts, articles, transdermal patches and bandages may also comprise a water insoluble polymer. Examples of such polymers are ethylcellulose, acrylic resins, co-polymer of methacrylic acid and acrylic acid ethyl ester, polylactic acid, PLGA, polyurethane, polyethylene vinyl acetate copolymer, polystyrene-butadiene copolymer and silicone rubber, or mixtures thereof.

These rate controlling polymers can be applied using a continuous coating film during the process of spraying and drying with active agents. The rate controlling film prepared with such a polymer is stable during implantation. The film should have enough strength to withstand tear and inner osmotic pressure, and have the stability not to swell or hydrate during the implantation life. In one embodiment, the coating formulation is used to coat pellets comprising the active ingredients that are compressed to form a solid, biodegradable insert.

Alternatively, miRNA compositions can be delivered using a sustained release device. Either non-biodegradable or biodegradable matrices can be used for delivery of nucleic acids, in addition to biodegradable matrices. These may be natural or synthetic polymers, although synthetic polymers may have better characterization of degradation and release profiles. The polymer is selected based on the period over which release is desired, generally in the range of at least two to six weeks, although longer periods may be desirable. In some cases linear release may be most useful, although in others a pulse release or "bulk release" may provide more effective results. The polymer may be in the form of a hydrogel (typically absorbing up to about 90% by weight of water), and can optionally be crosslinked with multivalent ions or polymers.

miRNA comprised within a composition of this invention can be delivered partially by diffusion but mainly by degradation of the polymeric system. In this case, biodegradable polymers, bioerodible hydrogels, and protein delivery systems are particularly embodiments. Examples of non-biodegradable polymers include ethylene vinyl acetate, poly (meth)acrylic acid, polyamides, copolymers and mixtures thereof. Examples of biodegradable polymers include synthetic polymers such as hydroxyacid polymers, for example, polymers of lactic acid and glycolic acid, polyanhydrides, poly(ortho)esters, polyurethanes, poly(butic acid), poly(valeric acid), and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

In one embodiment, the polymeric matrix is in the form of microparticles or nanoparticles. Microparticles can be in the form of microspheres, where the miRNA is dispersed within a solid polymeric matrix, or microcapsules, where the core is of a different material than the polymeric shell, and the miRNA composition is dispersed or suspended in the core, which may be liquid or solid in nature. Unless specifically defined herein, microparticles, microspheres, microcapsules, nanoparticles, nanospheres, and nanocapsules are used interchangeably.

Alternatively, the polymer may be cast as a thin slab or film, ranging from nanometers to four centimeters, a powder produced by grinding or other standard techniques, or even a gel such as a hydrogel. The matrices can be formed by solvent evaporation, spray drying, solvent extraction and other methods known to those skilled in the art.

In another embodiment, sustained release miRNA matrices are formed using fibrin. Fibrin-based biomaterial preparations can be used as provisional growth matrices for cells important in tissue repair during wound healing in vivo.

Another embodiment provides miRNA compositions incorporated in a conventional hydrophobic polymer matrix, e.g. of a polylactide, which is made more accessible for water by introducing a hydrophilic unit, e.g. of polyethyleneglycol, polyvinylalcohol, dextran or polymethacrylamide. The hydrophilic contribution to the amphipathic polymer is given by all the ethylene oxide groups in case of a polyethylene glycol unit, by the free hydroxyl groups in the case of a polyvinylalcohol unit or of a dextran unit, and by the amide groups in the case of a polymethyacrylamide unit.

In another embodiment, single-stranded miRNA can be expressed from transcription units within cells using eukaryotic promoters in appropriate DNA/RNA vectors from miRNA compositions comprising a vector. Suitable vectors include, but are not limited to, DNA plasmids and viral vectors. miRNA composition-expressing viral vectors can be constructed based on, but not limited to, adeno-associated virus, retrovirus, adenovirus, lentivirus, or alphavirus. In another embodiment, pol III based constructs are used to express nucleic acid molecules of the invention. Viral vectors capable of producing either persistent or transient expression of miRNA compositions in cells can be used.

The disclosed miRNA compositions can be administered using a syringe, bandage, transdermal patch, insert, syringe-like applicator, or any means known in the art, as a liquid, spray, aerosol, ointment, foam, cream, gel, balm, paste, or powder/talc or other solid.

The miRNA compositions may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents include water and physiologically acceptable buffered saline solutions such as phosphate buffered saline solutions with a substantially neutral pH. Additives may be mixed in with the formulation for maximum or desired efficacy of the delivery system or for the comfort of the patient. Such additives include, for example, lubricants, plasticizing agents, preservatives, gel formers, film formers, cream formers, disintegrating agents, coatings, binders, vehicles, coloring agents, odor controlling agents, humectants, viscosity controlling agents, pH-adjusting agents, and similar agents.

In one embodiment, the compositions contain sufficient amounts of at least one pH buffering agent to ensure that the composition has a final pH of about 3 to about 11, preferably between 6 and 8, most preferably at or near the pH of the skin. Suitable pH modifying agents include, but are not limited to, sodium hydroxide, citric acid, hydrochloric acid, acetic acid, phosphoric acid, succinic acid, sodium hydroxide, potassium hydroxide, ammonium hydroxide, magnesium oxide, calcium carbonate, magnesium carbonate, magnesium aluminum silicates, hydroxyapatite, malic acid, potassium citrate, sodium citrate, sodium phosphate, lactic acid, gluconic acid, tartaric acid, 1,2,3,4-butane tetracarboxylic acid, fumaric acid, diethanolamine, monoethanolamine, sodium carbonate, sodium bicarbonate, triethanolamine, and combinations thereof.

Preservatives can be used to prevent the growth of fungi and other microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetypyridinium chloride, chlorobutanol, phenol, phenylethyl alcohol, thimerosal, and combinations thereof.

The percent by weight of the active agents present in a formulation will depend on various factors, but generally will be from about 0.01% to about 98% of the total weight of the formulation, and typically about 0.1 to about 90% by weight, more typically less than 50%, most typically in the range of 0.5 to 10%.

The compositions can be formulated as emulsions for topical application. An emulsion contains one liquid distributed the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. In certain embodiment, excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

Suitable surfactants include, but are not limited to, anionic surfactants, non-ionic surfactants, cationic surfactants, and amphoteric surfactants. Examples of anionic surfactants include, but are not limited to, ammonium lauryl sulfate, sodium lauryl sulfate, ammonium laureth sulfate, sodium laureth sulfate, alkyl glyceryl ether sulfonate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, potassium lauryl sulfate, potassium laureth sulfate, sodium lauryl sarcosinate, sodium lauroyl sarcosinate, lauryl sarcosine, cocoyl sarcosate, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium and ammonium salts of coconut alkyl triethylene glycol ether sulfate; tallow alkyl triethylene glycol ether sulfate, tallow alkyl hexaoxyethylene sulfate, disodium N-octadecylsulfosuccinnate, disodium lauryl sulfosuccinate, diammonium lauryl sulfosuccinate, tetrasodium N-(1,2-dicarboxyethyl)-N-octadecylsulfosuccinnate, diamyl ester of sodium sulfosuccinic acid, dihexyl ester of sodium sulfosuccinic acid, dioctyl esters of sodium sulfosuccinic acid, docusate sodium, and combinations thereof.

Examples of nonionic surfactants include, but are not limited to, polyoxyethylene fatty acid esters, sorbitan esters, cetyl octanoate, cocamide DEA, cocamide MEA, cocamido propyl dimethyl amine oxide, coconut fatty acid diethanol amide, coconut fatty acid monoethanol amide, diglyceryl diisostearate, diglyceryl monoisostearate, diglyceryl monolaurate, diglyceryl monooleate, ethylene glycol distearate, ethylene glycol monostearate, ethoxylated castor oil, glyceryl monoisostearate, glyceryl monolaurate, glyceryl monomyristate, glyceryl monooleate, glyceryl monostearate, glyceryl tricaprylate/caprate, glyceryl triisostearate, glyceryl trioleate, glycol distearate, glycol monostearate, isooctyl stearate, lauramide DEA, lauric acid diethanol amide, lauric acid monoethanol amide, lauric/myristic acid diethanol amide, lauryl dimethyl amine oxide, lauryl/myristyl amide DEA, lauryl/myristyl dimethyl amine oxide, methyl gluceth, methyl glucose sesquistearate, oleamide DEA, PEG-distearate, polyoxyethylene butyl ether, polyoxyethylene cetyl ether, polyoxyethylene lauryl amine, polyoxyethylene lauryl ester, polyoxyethylene lauryl ether, polyoxyethylene nonylphenyl ether, polyoxyethylene octyl ether, polyoxyethylene octylphenyl ether, polyoxyethylene oleyl amine, polyoxyethyelen oleyl cetyl ether, polyoxyethylene oleyl ester, polyoxyethylene oleyl ether, polyoxyethylene stearyl amine, polyoxyethylene stearyl ester, polyoxyethylene stearyl ether, polyoxyethylene tallow amine, polyoxyethylene tridecyl ether, propylene glycol monostearate, sorbitan monolaurate, sorbitan monooleate, sorbitan monopalmitate, sorbitan monostearate, sorbitan sesquioleate, sorbitan trioleate, stearamide DEA, stearic acid diethanol amide, stearic acid monoethanol amide, laureth-4, and combinations thereof.

Examples of amphoteric surfactants include, but are not limited to, sodium N-dodecyl-.gamma.-alanine, sodium N-lauryl-.gamma.-iminodipropionate, myristoamphoacetate, lauryl betaine, lauryl sulfobetaine, sodium 3-dodecylaminopropionate, sodium 3-dodecylaminopropane sulfonate, sodium lauroamphoacetate, cocodimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, oleamidopropyl betaine, coco dimethyl sulfopropyl betaine, stearyl dimethyl sulfopropyl betaine, lauryl dimethyl sulfoethyl betaine, lauryl bis-(2-hydroxyethyl) sulfopropyl betaine, and combinations thereof.

Examples of cationic surfactants include, but are not limited to, behenyl trimethyl ammonium chloride, bis(acyloxyethyl)hydroxyethyl methyl ammonium methosulfate, cetrimonium bromide, cetrimonium chloride, cetyl trimethyl ammonium chloride, cocamido propylamine oxide, distearyl dimethyl ammonium chloride, ditallowedimonium chloride, guar hydroxypropyltrimonium chloride, lauralkonium chloride, lauryl dimethylamine oxide, lauryl dimethylbenzyl ammonium chloride, lauryl polyoxyethylene dimethylamine oxide, lauryl trimethyl ammonium chloride, lautrimonium chloride, methyl-1-oleyl amide ethyl-2-oleyl imidazolinium methyl sulfate, picolin benzyl ammonium chloride, polyquaternium, stearalkonium chloride, sterayl dimethylbenzyl ammonium chloride, stearyl trimethyl ammonium chloride, trimethylglycine, and combinations thereof.

Suitable suspending agents include, but are not limited to, alginic acid, bentonite, carbomer, carboxymethylcellulose and salts thereof, hydroxyethylcellulose, hydroxypropylcellulose, microcrystalline cellulose, colloidal silicon dioxide, dextrin, gelatin, guar gum, xanthan gum, kaolin, magnesium aluminum silicate, maltitol, triglycerides, methylcellulose, polyoxyethylene fatty acid esters, polyvinylpyrrolidone, propylene glycol alginate, sodium alginate, sorbitan fatty acid esters, tragacanth, and combinations thereof.

Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

Suitable antioxidants include, but are not limited to, butylated hydroxytoluene, alpha tocopherol, ascorbic acid, fumaric acid, malic acid, butylated hydroxyanisole, propyl gallate, sodium ascorbate, sodium metabisulfite, ascorbyl palmitate, ascorbyl acetate, ascorbyl phosphate, Vitamin A, folic acid, flavons or flavonoids, histidine, glycine, tyrosine, tryptophan, carotenoids, carotenes, alpha-Carotene, beta-Carotene, uric acid, pharmaceutically acceptable salts thereof, derivatives thereof, and combinations thereof.

Suitable chelating agents include, but are not limited to, EDTA, disodium edetate, trans-1,2-diaminocyclohexane-N,N,N,N'-tetraaceticacid monohydrate, N,N-bis(2-hydroxyethyl)glycine, 1,3-diamino-2-hydroxypropane-N,N,N',N'-te-traacetic acid, 1,3-diaminopropane-N,N,N,N'-tetraacetic acid, ethylenediamine-N,N'-diacetic acid, ethylenediamine-N,N'-dipropionic acid, ethylenediamine-N,N'-bis(methylenephosphonic acid), N-(2-hydroxyethyl)ethylenediamine-N,N,N',N'-triacetic acid, ethylenediamine-N,N,N',N'-tetrakis(methylenephosphonic acid), O,O'-bis(2-aminoethyl)ethyleneglycol-N,N,N',N'-tetraacetic acid, N,N-bis(2-hydroxybenzyl)ethylenediamine-N,N-diacetic acid, 1,6-hexamethylenediamine-N,N,N,N'-tetraacetic acid, N-(2-hydroxyethyl)iminodiacetic acid, iminodiacetic acid, 1,2-diaminopropane-N,N,N',N'-tetraacetic acid, nitrilotriacetic acid, nitrilotripropionic acid, nitrilotris(methylenephosphoric acid), 7,19,30-trioxa-1,4,10,13,16,22,27,33-octaazabicyclo[11,11,11] pentatriacontane hexahydrobromide, triethylenetetramine-N,N,N',N'',N''',N''''-hexaacetic acid, and combinations thereof.

Suitable emollients include, but are not limited to, myristyl lactate, isopropyl palmitate, light liquid paraffin, cetearyl alcohol, lanolin, lanolin derivatives, mineral oil, petrolatum, cetyl esters wax, cholesterol, glycerol, glycerol monostearate, isopropyl myristate, lecithin, and combinations thereof.

Suitable humectants include, but are not limited to, glycerin, butylene glycol, propylene glycol, sorbitol, triacetin, and combinations thereof.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. Liquid sprays are conveniently delivered from pressurized packs, for example, via a specially shaped closure. Oil-In-Water emulsions can also be utilized in the compositions, patches, bandages and articles. These systems are semisolid emulsions, micro-emulsions, or foam emulsion systems. Usually such a system has a "creamy white" appearance. Typically, the internal oil phase is in the range in percentage composition of about 10% to about 40% oil by weight and the external phase may contain 80% or more water. The oleaginous phase may contain, but is not limited to, long-chain alcohols (cetyl, stearyl), long-chain esters (myristates, palmitates, stearates), long-chain acids (palmitic, stearic), vegetable and animal oils and assorted waxes. These can be made with anionic, cationic, nonionic or amphoteric surfactants, or with combinations especially of the nonionic surfactants.

In some embodiments, the active ingredients can be formulated with oleaginous bases or ointments to form a semisolid composition with a desired shape. For example, the composition can be shaped for easy application to, or insertion into, a wound, ulcer, puncture wound or surgical site. This class of formulations includes the active ingredients and semisolids. In addition to the active ingredients, these semisolid compositions can contain dissolved and/or suspended bactericidal agents, preservatives and/or a buffer system. The petrolatum component in many of these bases can be any paraffin ranging in viscosity from mineral oil employing incorporated isobutylene, colloidal silica, or stearate salts to paraffin waxes. White and yellow petrolatums are examples of such systems. Bases of this class can be made by incorporating high-melting waxes into a fluid mineral oil via fusion or by incorporation of polyethylene into mineral oil at elevated temperature. Polysiloxanes (also known as silicones) are suitable for use in these bases and typically have a viscosity in the range of about 0.5 to lo6 centistokes. The organic entities attached to the polysiloxane are preferably lower molecular weight hydrocarbon moieties having from 1 to 8 carbons each, such as lower alkyl, lower alkenyl, phenyl and alkyl substituted phenyl, and phenyl (lower)alkyl, such as benzyl. In such a moiety, each lower alkyl or alkenyl group preferably has 1 to 3 carbons inclusive, such as in a dimethylsiloxane polymer.

Absorption bases can be used with such an oleaginous system. In addition to the active ingredients, additional ingredients with the capacity to emulsify a significant quantity of water can be employed. Water-in-oil (w/o) emulsions can be formed wherein the external phase is oleaginous in character. Preservatives/bacteriostats, such as the parabens, buffer systems, etc. can be incorporated into these bases as emulsified aqueous solutions together with the active ingredient. Diverse additives are conveniently used as the emulsifier, and these include, but are not limited to, cholesterol, lanolin (which contains cholesterol and cholesterol esters and other emulsifiers), lanolin derivatives, beeswax, fatty alcohols, wool wax alcohols, low HLB (hydrophobellipophobe balance) emulsifiers, and assorted ionic and nonionic surfactants, singularly or in combination.

Articles containing the disclosed miRNA compositions for application to inflammatory skin lesions, for example psoriatic leasions, are also provided. For example, transdermal patches, dressings, pads, wraps, matrices and bandages are provided that are capable of being adhered or otherwise associated with the skin of a subject and capable of delivering a therapeutically effective amount of one or more disclosed miRNA inhibitors.

The miRNA compositions can be impregnated in wound dressings known in the art of wound healing such as, but not necessarily restricted to, a cream, ointment, gel, solution, lotion, liniment, viscous emulsion, powder, paste, beads, a film dressing such as polyurethane film, a foam dressing such as a polyethane or polyurethane foam dressing, a hydrocolloid dressing, a hydrogel, alginate, gauze, paraffin gauze, hypertonic-saline-gauze, wet-dry-saline gauze, continuously-moist-saline gauze, expanding dressings, or Silver nanotech. The selection of dressing depends on the specific condition, grade, description, characteristics and bacterial profile.

Topical formulations, also known as transdermal formulations, may be prepared by incorporating the nucleic acid or miRNA in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, formulations of this invention may further include one or more accessory ingredient(s) selected from, for example, diluents, buffers, flavoring agents, binders, disintegrants, surface active agents, thickeners, lubricants, preservatives (including antioxidants), and the like.

The formulations of the present invention can have immediate release, sustained release, delayed-onset release or any other release profile known to one skilled in the art.

Treatment methods may include various "unit doses." A unit dose is defined as containing a predetermined quantity of a therapeutic composition(s). The quantity to be administered, and the particular route and formulation, are within the skill of those in the clinical arts. A unit dose need not be administered as a single administration but may comprise multiple applications over a set period of time. With respect to a viral component of the present invention, a unit dose may conveniently be described in terms of µg or mg of miRNA or miRNA mimetic. Alternatively, the amount specified may be the amount administered as the average daily, average weekly, or average monthly dose.

miRNA can be administered to the patient in a dose or doses of about or of at least about 0.005, 0.05, 0.5, 1, 5, 10, 15, 20, 25, 30, 35, 40, 45, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 µg, ng, or mg, or more, or any range derivable therein. Alternatively, the amount specified may be the amount administered as the average daily, average weekly, or average monthly dose, or it may be expressed in terms of mg/kg, where kg refers to the weight of the patient and the mg is specified above.

Dosing is dependent on severity and responsiveness of the inflammatory disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on EC.sub.50s found to be effective in in vitro and in vivo animal models.

Dosage levels on the order of about 1 µg/kg to 100 mg/kg of body weight per administration are useful in the treatment of a disease. One skilled in the art can also readily determine an appropriate dosage regimen for administering the disclosed to a given subject. For example, the miRNA composition can be administered to the subject once, e.g., as a single injection. Alternatively, the miRNA composition can be administered once or twice daily to a subject for a period of from about three to about twenty-eight days, or from about seven to about ten days.

Thus, the miRNA composition can be administered at a unit dose less than about 75 mg per kg of bodyweight, or less than about 70, 60, 50, 40, 30, 20, 10, 5, 2, 1, 0.5, 0.1, 0.05, 0.01, 0.005, 0.001, or 0.0005 mg per kg of bodyweight, and less than 200 nmol of miRNA composition per kg of bodyweight, or less than 1500, 750, 300, 150, 75, 15, 7.5, 1.5, 0.75, 0.15, 0.075, 0.015, 0.0075, 0.0015, 0.00075, 0.00015 nmol of miRNA composition per kg of bodyweight.

Certain factors may influence the dosage required to effectively treat a subject, including, but not limited to, the severity of the inflammatory skin disease or disorder, previous treatments, the general health and/or age of the subject, and other diseases present. The effective dosage of an miRNA used for treatment may increase or decrease over the course of a particular treatment. Changes in dosage may result and become apparent from the results of diagnostic assays. For example, the subject can be monitored after administering an miRNA composition. Based on information from the monitoring, an additional amount of the miRNA composition can be administered.

Where a dosage regimen comprises multiple administrations, it is understood that the effective amount of miRNA composition administered to the subject can include the total amount of miRNA composition administered over the entire dosage regimen. One skilled in the art will appreciate that the exact individual dosages may be adjusted somewhat depending on a variety of factors, including the specific miRNA composition being administered, the time of administration, the route of administration, the nature of the formulation, the rate of excretion, the particular disorder being treated, the severity of the disorder, the pharmacodynamics of the oligonucleotide agent, and the age, sex, weight, and general health of the patient. Wide variations in the necessary dosage level are to be expected in view of the differing efficiencies of the various routes of administration. For instance, oral administration generally would be expected to require higher dosage levels than administration by intravenous injection. Variations in these dosage levels can be adjusted using standard empirical routines of optimization, which are well-known in the art. The precise therapeutically effective dosage levels and patterns are preferably determined by the attending physician in consideration of the above-identified factors.

In one embodiment, the unit dose is administered less frequently than once a day, e.g., less than every 2, 4, 8 or 30 days. In another embodiment, the unit dose is not administered on a regular schedule. For example, the unit dose may be administered a single time. Because oligonucleotide agent-mediated silencing can persist for several days after administering the miRNA composition, in many instances, it is possible to administer the composition with a frequency of less than once per day, or, for some instances, only once for the entire therapeutic regimen.

In some embodiments, a subject is administered an initial dose, and one or more maintenance doses of an miRNA composition. The maintenance dose or doses are generally lower than the initial dose, e.g., one-half less of the initial dose. A maintenance regimen can include treating the subject with a dose or doses ranging from 0.01 µg to 75 mg/kg of body weight per day, e.g., 70, 60, 50, 40, 30, 20, 10, 5, 2, 1, 0.5, 0.1, 0.05, 0.01, 0.005, 0.001, or 0.0005 mg per kg of bodyweight per day. The maintenance doses are preferably administered no more than once every 5, 10, or 30 days. Further, the treatment regimen may last for a period of time which will vary depending upon the nature of the particular disease, its severity and the overall condition of the patient. In certain embodiments the dosage may be delivered no more than once per day, e.g., no more than once per 24, 36, 48, or more hours, e.g., no more than once every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

In one embodiment, administration may be at least a once a day administration for at least one day. In another embodiment, administration may be at least a twice a day administration for at least one day. In other embodiments, administration may be at least once a day, at least twice a day, at least three times a day, at least four times a day. In another embodiment, administration is on an add-need basis throughout the day. In yet another embodiment, administration may be at least a once a day for at least one week. In still another embodiment, administration may be at least a twice a day for at least one week. In a further embodiment, administration may be for an extended period of time. In one embodiment, an extended period of time is greater than one week, is two weeks, is three weeks, is at least one month, is at least two months, is at least three months, is at least four months is at least six months, is at least one year, is at least two years, is at least the time period necessary for an effective therapy.

The disclosed miRNA compositions can be administered topically or subcutaneously at or adjacent to the site of a lesion or a wound. In one embodiment, the miRNA compositions are administered topically. Topical administration may be in any suitable form, such as liquids, ointments, lotions, creams, gels, drops, sprays, patches or powders, as described above. The miRNA compositions may also be incorporated into inserts, wound dressings, or other materials that come into contact with the wound. Each possibility represents a separate embodiment of the present invention.

The miRNA compositions may be administered using any method that facilitates transdermal delivery. For example, the miRNA compositions may be administered using compositions and methods that open channels within the stratum corneum, including, but not limited to laser assisted delivery (LAD), tape stripping, ultrasound and cold plasma.

The miRNA compositions may be administered using laser assisted delivery (LAD). Generally, in LAD, a pulsed laser removes micrometers (μm) of the stratum corneum per pulse. The laser can stop at the start of wet viable epidermis and not violate the skin's blood vessels, so there is no bleeding. The hole created in the stratum corneum can then facilitate delivery of drugs or collection of biochemical from the skin site. The treated area of the skin can be illuminated with very short pulses of light which is preferentially absorbed by the absorber causing a very large number of tiny explosions. The tiny explosion forces portions of the drug to penetrate into the skin.

The miRNA compositions may be administered using tape stripping. A tape stripping method typically involves applying an adhesive tape to the skin of a subject and removing the adhesive tape from the skin of the subject one or more times. In certain examples, the adhesive tape is applied to the skin and removed from the skin about one to ten times. Alternatively, about ten adhesive tapes can be applied to the skin and removed from the skin.

The miRNA compositions may be administered using electroporation. For example, the miRNA compositions are administered to the skin and a pulsed electric field applied to the skin to cause electrotransport of the miRNA compositions into cells of the skin.

The miRNA compositions may be for formulated into sustained release formulations such as polymeric delivery systems, mini-pumps, and hydrogels, as described above. These can be loaded with miRNA compositions, injected or implanted into the lesions, where the miRNA may be released over a therapeutically effective time period.

The miRNA compositions may be administered in a single dose, in multiple doses, in a continuous or intermittent manner, depending, for example, upon the recipient's physiological condition. Administration of the compositions may be essentially continuous over an indeterminate period of time, for example, at regular intervals. Alternatively, the compositions can be administered continuously for a preselected period of time or in a series of spaced doses. Each possibility represents a separate embodiment of the present invention.

In one embodiment, the term "about", refers to a deviance of between 0.0001-5% from the indicated number or range of numbers. In one embodiment, the term "about", refers to a deviance of between 1-10% from the indicated number or range of numbers. In one embodiment, the term "about", refers to a deviance of up to 25% from the indicated number or range of numbers.

In some embodiments, the term "comprise" or grammatical forms thereof, refers to the inclusion of the indicated active agent, such as the nucleic acids and/or miRNAs of this invention, as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredient is the indicated active ingredient, however, other nucleic acids and/or miRNA may be included which are for stabilizing, preserving, etc. the formulation, but are not involved directly in the therapeutic effect of the indicated active ingredient. In some embodiments, the term "consisting essentially of" may refer to components, which exert a therapeutic effect via a mechanism distinct from that of the indicated active ingredient. In some embodiments, the term "consisting essentially of" may refer to components, which exert a therapeutic effect and belong to a class of compounds or nucleic acids distinct from that of the indicated active ingredient (nucleic acid and/or miRNA). In some embodiments, the term "consisting essentially of" may refer to components, which exert a therapeutic effect and belong to a class of compounds distinct from that of the indicated active ingredient, by acting via a different mechanism of action. In some embodiments, the term "consisting essentially of" may refer to components which facilitate the release of the active ingredient. In some embodiments, the term "consisting" refers to a composition, which contains the active ingredient and a pharmaceutically acceptable carrier or excipient.

Further, as used herein, the term "comprising" is intended to mean that the system includes the recited elements, but not excluding others which may be optional. By the phrase "consisting essentially of" it is meant a method that includes the recited elements but exclude other elements that may have an essential significant effect on the performance of the method. "Consisting of" shall thus mean excluding more than traces of other elements. Embodiments defined by each of these transition terms are within the scope of this invention.

In one embodiment, the term "a" or "one" or "an" refers to at least one. In one embodiment the phrase "two or more" may be of any denomination, which will suit a particular purpose. In one embodiment, "about" may comprise a deviance from the indicated term of +1%, or in some embodiments, −1%, or in some embodiments, ±2.5%, or in some embodiments, ±5%, or in some embodiments, ±7.5%, or in some embodiments, ±10%, or in some embodiments, ±15%, or in some embodiments, ±20%, or in some embodiments, ±25%.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub ranges as well as individual numerical values within that range. For example, description of a range such as from 1 to 6 should be considered to have specifically disclosed sub ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

The following examples are presented in order to more fully illustrate embodiments of the invention. It should in no way, however, be construed as limiting the broad scope of the invention.

EXAMPLES

Materials and Methods

Cells Cultures:
293T (human embryonic kidney cells), HaCaT (human keratinocyte cells), and PHK (primary human kidney cells)

cells were grown as described (Lerman G, Avivi C, Mardoukh C et al. MiRNA expression in psoriatic skin: reciprocal regulation of hsa-miR-99a and IGF-1R. *PloS one* 2011; 6: e20916; Sonnenberg G F, Fouser L A, Artis D. Functional biology of the IL-22-IL-22R pathway in regulating immunity and inflammation at barrier surfaces. *Adv Immunol*; 107: 1-29). In some experiments HaCaT immortalized keratinocytes (KC) were used rather than primary human KC (PHK), due to the fact that miRNA mimics are diluted and lost during cell division.

Cell Proliferation-BrdU Incorporation:

Cell growth was assessed by seeding 3000 cells per well in 96-well plates. Viable cell counts were monitored from seeding time (t=0) to 72 h. Cell counts were determined using the MTT (3-[4, 5-dimethylthiazol-2-yl]-2, 5-diphenyl tetrazolium bromide)-based Cell Growth Determination Kit TOX-1 (Sigma-Aldrich, Israel Ltd. Rehovot 76100 ISRAEL) and the BrdU colorimetric kit (cat. 11 647 229001 Roche), according to the manufacturer's instructions Each experiment was performed in triplicate.

Quantitative Real Time PCR (qPCR):

Total RNA of cells was extracted using Norgen total RNA purification Kit (Norgenbioteccorp #17200). Quantification of miRNA was performed by TaqManH Real-Time PCR was performed on 10 ng RNA using the ABI 7900HT thermocycler (Applied Biosystems) for 40 cycles. Target miR/gene expression was normalized between different samples based on the values of RNU48/Rplpo expression respectively. For CCL20 assay number Hs01011368-ml from Applied Biosystems was use.

Plasmids:

The plasmids pMSCV-miR-197 and pMSCV-HTR were as per Vorhoeve et al. (Voorhoeve P M, le Sage C, Schrier M et al. A genetic screen implicates miRNA-372 and miRNA-373 as oncogenes in testicular germ cell tumors. *Cell* 2006; 124: 1169-8). Luciferase-IL22RA-3'UTR (HmiT016091-MT01), Luciferase-IL10RB-3'UTR (HmiT009687-MT01), and the control no-3'UTR (CmiT000001-MT01) plasmids were purchased from GeneCopoeia, (GeneCopoeialnc, Rockville, Md. 20850USA). The WT psiCHECK-Luciferase-IL22RA-3'UTR was generated by amplifying by PCR reaction fragment of ~1000 bp containing the 3'UTR of IL22RA1 mRNA from the HmiT016091-MT01 plasmid. The primers used are listed in Table 1 below (marked is the restriction enzyme site). The fragment was cut with XhoI and NotI and ligated into psiCHECK-2 that was cut with the same enzymes.

fragment was cut with XhoI and NotI and ligated into psiCHECK-2 that was cut with the same enzymes.

Luciferase-IL17RA-3'UTR (HmiT070362-MT06), plasmids was purchased from GeneCopoeia, (GeneCopoeialnc, Rockville, Md. 20850USA).psiCHECK-Luciferase-IL17RA-3'UTR was generated by amplifying by PCR reaction fragment of ~1400 bp containing the 3'UTR of IL17RA mRNA using forward primer; gcgcCTCGAGCCAGCTTT-GAGAGAGGAGTG [SEQ ID NO: 75] which include XhoI site and revers primer atGCGGCCGCGAGGCTCATCA-GACGAAAGG [SEQ ID NO: 76], which include NotI site. (both restriction enzyme sites is marked). The fragment was cut with XhoI and NotI and ligated into psiCHECK-2 that was cut with the same enzymes. The IL17RA-3'UTR mutant for the hsa-mir-197 seed sequence was created using the Megaprimer Mutagenesis assay using the same forward primer and mutant primer; GTGGAGATGGGGTATGTG-GATGAAGGGGAGGATCGCTCAAACTCC[SEQ ID NO: 77] for the first amplification generated a fragment of ~500 bp that was used for the second amplification with the same reverse primer The ~1400 fragment was cut with XhoI and NotI and ligated into psiCHECK-2 that was cut with the same enzymes.

Transfections:

293T cells were seeded at 0.5-1×10$^5$ cells per well and transfected by calcium phosphate in HEPES buffer method. HaCaT cells were transfected using Lipofectamine™ 2000 Reagent (Invitrogen, USA). PHK cells were transfected using FugeneHD or X-tremeGENE Transfection Reagent (Roche, CH-4070, Basel, Switzerland).

Stably transfected HaCaT cells were generated by transfecting with plasmids pMSCV-miR-197 or pMSCV-HTR and lines were achieved after selection for 4 weeks with Blasticidin at a final concentration of 16 μg/ml.

Luciferase Assay:

Luciferase assays were performed using the Dual-Luciferase® Reporter (DLR) Assay System (Promega Corporation Madison, Wis. 53711 USA), or with Luc-Pair™ miR Luciferase Assay (GeneCopoeia Rockville, Md. 20850 USA).

Determination of Proteins Expression by Western Blots:

Western blots (WB) were performed using monoclonal Mouse IgG1 Clone #305405, anti-Human IL22RA1 antibody (R&D Systems, Inc. MN 554193 USA) and β-Actin AC-15 antibody (ab276) (abcam Cambridge, CB4 OFW, UK). anti IL17RA Rabbit monoclonal to IL7A Receptor, (ab134086) (Abcam Cambridge, CB4 OFW, UK). For

TABLE 1

| Primers | | |
|---|---|---|
| Primer | SEQ ID NO: | Sequence |
| Forward primer with XhoI | SEQ ID NO: 1 | 5'-CCG*CTCGAG*CGGGGAATGGGAAAGGCTTGGTGC-3' |
| Reverse primer with NotI | SEQ ID NO: 2 | 5'-ATAGTTTA*GCGGCCGC*ATTCTTATGCTACCGTTTATTGGGCACTG-3' |
| Mutant primer | SEQ ID NO: 3 | 5'-CTCATGGAGTTGTAACAAAGATGAAATG-3' |

The IL22RA1-3'UTR mutant for the hsa-mir-197 seed sequence was created using the Megaprimer Mutagenesis assay using primer forward (SEQ ID NO: 1) and mutant primer (SEQ ID NO: 3) for the first amplification generated a fragment of ~100 bp that was used for the second amplification with the reverse primer (SEQ ID NO: 2). The ~1000 immune staining of IL22RA1 in the FFPE, Rabbit polyclonal to IL22 Receptor Alpha (ab5984) from (abcam Cambridge, CB4 OFW, UK) was used.

Chromatin Immunoprecipitation (ChIP) Assay:

The ChIP assay was performed as follows: 10$^7$ primary human keratinocytes were treated or not with 0.5 ng/ml of IL-22 for 30'. Next, formaldehyde (Sigma) was added to final concentration of 1%, for 10'. To quench the cross-linking, glycine was added to final concentration of 0.125M was added for 5'. Cells were collected and washed twice in PBS, containing protease inhibitors (Complete mini, Roche Applied Science) and Pepstatin (Sigma). Next, the pellet was washed sequentially for 10 min each in 5 ml of buffers. Lysates were sonicated 6×10 sec bursts to generate DNA fragment ~1000 bp. Debris were removed by centrifugation for 10 min at 1000 g, at 40° C. 15-20 µg of DNA from each treatment was first diluted in dilution buffer (0.01% SDS, 1.1% Triton X-100, 1.2 mM EDTA, 16.7 mM Tris-HCl (pH 8.1) and 167 mM NaCl). Lysates were pre-cleared in 40 µl of protein A+ salmon sperm beads (Upstate Biotechnology) for 30 min at 40 C. Equal amount from each treatment was taken as input control. Equal aliquots of each treatment was subject to immuno-precipitation with either control human Ab (IgG) or with Phospho-Stat3 (Tyr705) Antibody (Cell Signaling #9131). After overnight at 40° C., 60 µl of protein A+ salmon sperm beads was added, for 2 h at 40° C. Next pellets were washed sequentially for 5 min each in 2.5 ml of buffers. The immune complexes were eluted.

Next cross-linking was performed by adding 16 µl of 5M NaCl, 8 µl of 0.5M EDTA (pH 6.5) and 16 µl of 1M Tris-HCl (pH 8.1) and incubated O.N. at 65° C. DNA was purified by first, adding Proteinase K (10 mg/ml) for 2 h at 55° C. follow by phenol/chloroform (sigma) extraction and ethanol precipitation. Equal aliquots of each sample were analyzed by quantitative real time PCR.

The ChIP qRT of miR-197 promoter: The results present the amount measured by PCR of immune precipitated DNA with the anti pSTAT3 divided to the amount of measured by PCR of input DNA. All PCR reactions were performed with qPCR SYBR® Green dye. The mean−/+SD was calculated from 4 independent experiments (t test *P=0.016). Primers that were used in the ChIP are the following primers:

```
Forward:
                                        (SEQ ID NO: 4)
5'AGTGGGTGGTCTTTTACAGCA3'

Reverse:
                                        (SEQ ID NO: 5)
5'GACCTTTTCACCCTGCTTCA3'
```

Tm=60° C. according to the manufactures protocol (Applied Biosystems Inc Foster City Calif. 94404).

Migration Assay:

Migration assays were performed using Oris™ Cell Migration Assay (Platypus Technologies Madison Wis. 53711 USA). Microscope model: OlympusSZX16 Research Stereomicroscope. Olympus SDF PLAPO objective lenses extra-wide zoom range of 7.0×-115×. Camera model: Nikon DSD-Fil. Acquisition software: AnalySIS getIT. Image processing software: Image-J program.

Methylation Assay:

DNA was extracted using the AlPrep DNA/RNA FFPE Kit (USA QIAGEN Inc. 27220, CA 91355) for biopsies or by Archive Pure DNA Cell/Tissue Kits (5 PRIME, Inc.) for PHK. Bisulfate reactions were done with EZ DNA Methylation-Gold Kit (ZYMO research). PCR and sequencing was performed with the specific primers.

```
Forward
                                        (SEQ ID NO: 6)
5':TTTTATTAAAAATATAAAAATTAGTTAGGTATGGT Reverse
                                        (SEQ ID NO: 7)
5':ATAGAGTGAGTTTGTTTTTTTTTTGTT
```

The sequencing was analyzed by BioEdit.

MiRNA Array

Total RNA including miRNAs from normal skin (n=3), psoriatic lesion (n=3), or psoriatic patient uninvolved skin (n=3), was isolated using Ambion mirVana™ miRNA Isolation Kit. Total RNA (2 mg) from each sample was labeled with the mirVana miRNA Labeling Kit (Applied Biosystems/AmbionUSA). The fluorescently-labeled RNA samples were hybridized to an expression array. The array was scanned and analyzed using Genepix pro 4000b Axon and JMP statistic software.

Materials

Recombinant Human IL-22 cytokine and Recombinant Human IL17A cytokine were purchase from (PeproTech, Rocky Hill, N.J.). STAT3 inhibitor (VI, S3I-201) was purchased from form Santa Cruz Biotechnology, Inc. Anago-miR-197 (Anti-miR miRNA Inhibitors, 5 nmol ID AMI0354) was purchased from Applied Biosystems). miRNAs used throughout the examples were supplied by a number of outside sources including: Sigma (miR-197 catalog # HMI0327-5NMOL)—This is a ready-to-use MISSION miRNA mimic, which is a small, double-stranded RNA molecules designed to mimic endogenous mature miRNA molecules when introduced into cells; Dharmacon Research, Inc. (catalog # C-300531-05-0002 2 nmol) miRIDIAN microRNA hsa-miR-197-3p mimic; Applied Biosystems (catalog #4464066) miRBase Accession Number: MI0000239; and Exiqon (Product #471956-001) escription: miRCURY LNA™ microRNA Mimic, 5 nmol.

Patients—Skin Samples

All skin donors were of Caucasian origin aged 18 to 85 years. All patients were clinically diagnosed with Psoriasis Vulgaris, and did not receive systemic immunosuppressive treatment, phototherapy (Psoralen and UVA (PUVA)/solarium/UVB), or topical therapy for at least 3 weeks prior to skin biopsy. Three mm punches were taken mostly from upper and lower limbs. The uninvolved samples were taken from the same area, about 5 cm away from the lesion biopsy. Normal skin biopsies were taken from full thickness skin remaining after plastic surgery. All the biopsies were evaluated by a dermatopathologist for histological diagnosis. Half of each biopsy was snap-frozen and the other half was embedded in paraffin. The study was approved by both the Tel Aviv University and Sheba Medical Center Helsinki Ethics Committees. All participants provided written informed consent.

Preparation of Mouse Model

Mice Psoriasis and Psoriasis-Form Preparation:

All experiments were done under ethics committee approval to use human skin obtained in operations of skin reduction (number 815) and a permit to perform these animal experiment from the Council for Experiments on animals at the Israeli health ministry (application number 5528).

Female mice at the age between 4-6 week, strains C.B-17/IcrHsd-Prkdc-scid were purchased from Harlan Laboratories in Israel.

Preparation of the Skin:

Skin is wash consecutively ten time in PBS+Antibiotics (Penicillin-Streptomycin Amphotericin B Solution, 10,000 units/ml Penicillin G Sodium Salt, 10 mg/ml Streptomycin Sulfate, 25 microgram/ml Amphotericin B) purchased from Biological Industries Israel Beit-Haemek Ltd. Kibbutz Beit-Haemek, 25115, Israel). Skin was then cut into pieces of 1×2 cm.

Preparation of the Mice for Surgery:

Two days before transplantation and for three days after surgery mice were given drinking water which added with 2 ml of optalgin 1 gram/2 ml. (Teva Pharmaceutical Industries Ltd.)

Mice were anesthetized with injection 1% microliter of the weight with solution of Xylasin 1.25 mg/ml+Ketamin 12.5 mg/ml in PBS.

A part of the mice skin was removed from their back and the human skin was implanted instead. The human skin was cover with cover plast elastic 8×5 HYPORPLAST for one week.

After the human skin was accepted activated psoriasis lymphocyte were injected into to transplant skin.

Activation of T Cells:

Peripheral blood mono-nuclear cells (PBMC) from psoriatic patients were isolated by density centrifugation from heparinized blood diluted 1:1 with Hank's (GIBCO) over layered on Histopaque 1.077 mg per ml (Sigma, St Louis, Mo.) and washed twice in RPMI-1640 (GIBCO). Immunocytes (1-2×10$^6$ cells per ml) were then transferred to serum-RPMI (15% heat-inactivated autologous serum in RPMI-1640, 2 mM L-glutamine, 100 U penicillin per ml, 100 g streptomycin per ml, and 1 mg gentamicin per liter (GIBCO) containing 1 g Staphylococcal enterotoxin B (SEB) per ml (Toxin Technologies, Sarasota, Fla.) and 20 unit per liter of human IL-2 (Boehringer Mannheim Biochemicals, Indianapolis, Ind.) and cultured (37° C., 5% CO2) in six well tissue culture clusters (Costar, Cambridge, Mass.) for 48 h. The cells were pipetted off the plates, gently washed in cold medium to release adherent cells, washed twice in RPMI-1640 Finally the cells were removed, washed twice in RPMI-1640, resuspended (10-15×10$^6$ cells per ml) in PBS (GIBCO), and transferred to 1 ml syringes (Becton Dickinson) for injection into the grafts.

The miRNAs molecules were labeled with Cy5 to create fluorescent miRNAs; Mimic Catalog #CN-0010000-01 (negative control); 3' Cy-5 on Antisense strand; and Mimic Catalog #C-300531-05, miRIDIAN miRNA hsa-197-3p-Mimic3' Cy-5 on Antisense strand; were purchased from GE Dharmacon Inc.

At given time points, mice were sacrificed and the human skin was removed and fixed to FFPE.

Statistical Analysis:

Statistical significance was done using the Student's t-test. For a single comparison, a p-value <0.05 was considered significant.

Example 1

MiR-197 Over-Expression Decreases Proliferation and Induces Differentiation of Keratinocytes Results:

The immortalized keratinocytes (KC) cell line HaCaT was stably transfected with miR-197 (SEQ ID NO: 9). The plasmid expresses the pre-miR-197 but once in the cells, the pre-cursor form is processed into the mature miR-197 (SEQ ID NO: 8) (HaCaTmiR-197) (FIG. 1A). Stably expressing miR-197 HaCaT cells were chosen as a model system, rather than primary human KC (PHK), due to the fact that miRNA mimics are diluted and lost during cell division. Moreover, according to the results, the replication rate of cells which absorb the miRNA is diminished, and therefore, if non-stably transfected cells were used, in few hours the non-transfected cell would populate the culture.

Figure 1B:
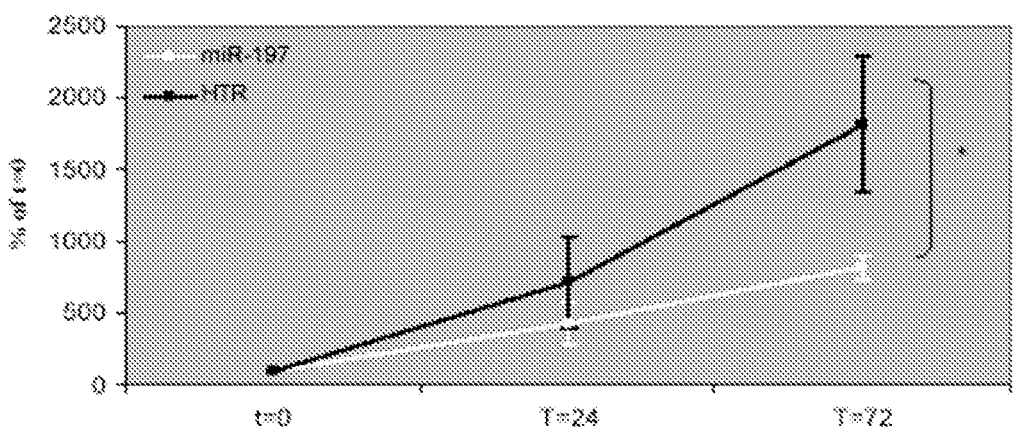
Figure 1C:
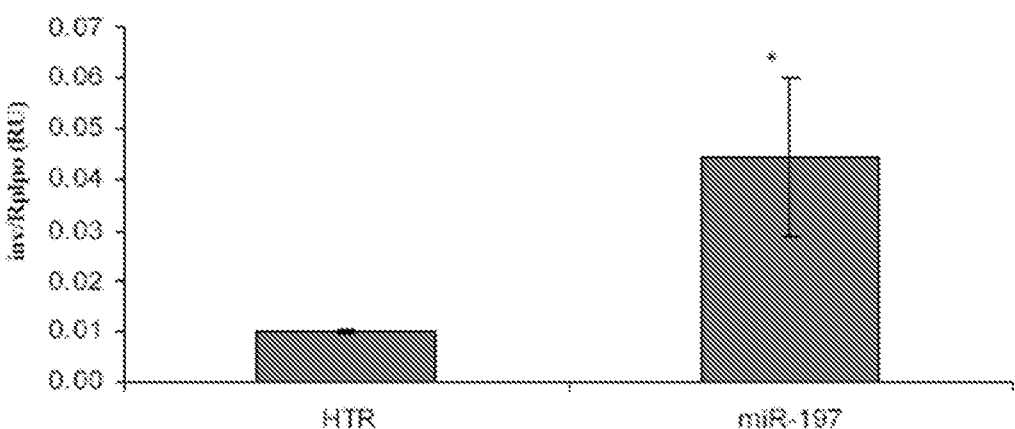

The results showed that BrdU incorporation was decreased in HaCaT-miR-197 cells relative to HaCaT cells transfected with HTR control RNA (HaCaT-HTR) at both the 24 h and 72 h time points (FIG. 1B). The expression of involucrin, a marker for KC differentiation, was higher in HaCaT-miR-197 cells vs. control cells (FIG. 1C). These results indicate that miR-197 slows KC proliferation rate and directs them towards differentiation.

Figure 11B:
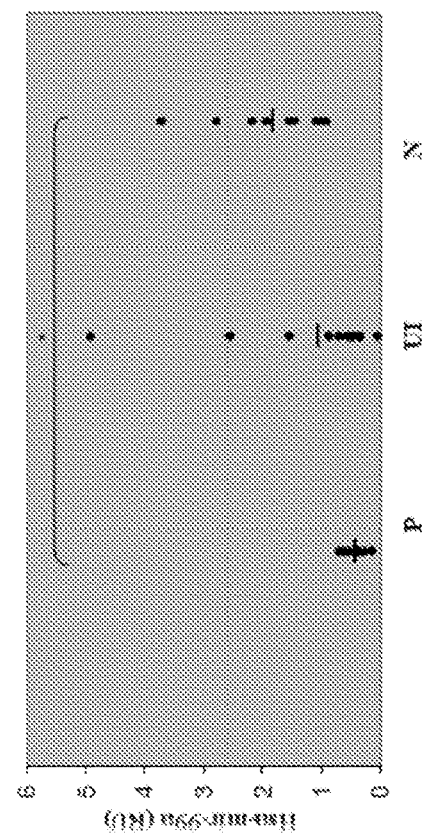
FIGS. 11A-G present the results of expression quantification of human miRNAs from normal healthy skin (N), psoriatic lesions (P) or psoriatic uninvolved skin (UI). Quantitative PCR was performed and normalized by Rnu48 for Hsa-miR-99a (11A) ("Hsa"=*Homo sapiens*), Hsa-miR-150 (11B), Hsa-miR-423 (11C), Hsa-miR-197 (11D), Hsa-miR-203 (11E), Hsa-Let7c (11F) and Has-miR-125b-2 (11G).
Figure 11A:
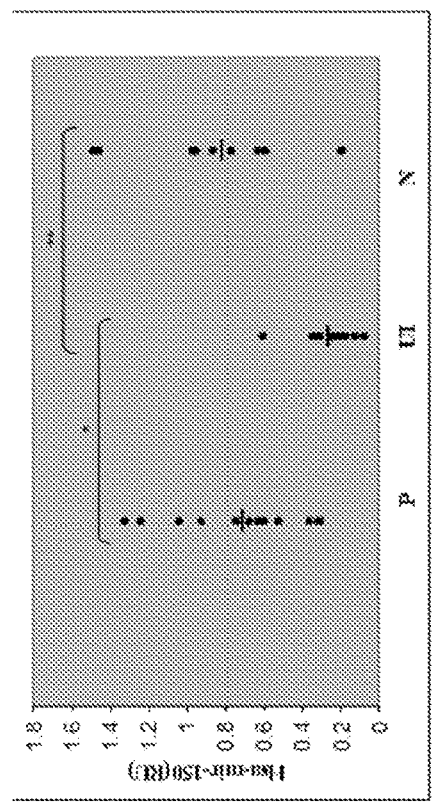
Figure 11D:
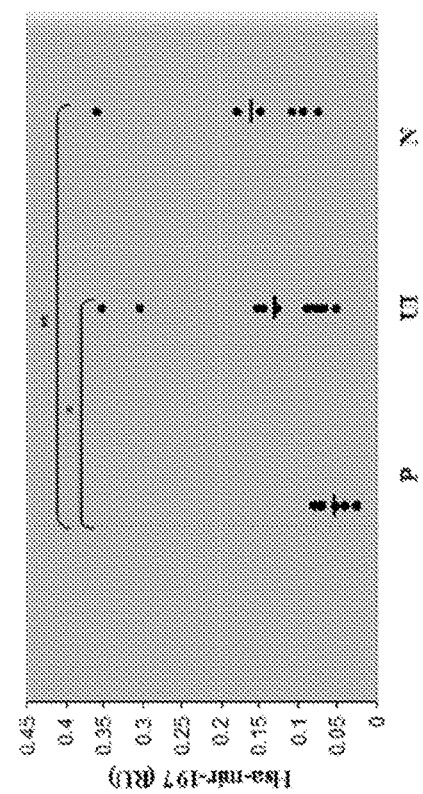
Figure 11C:
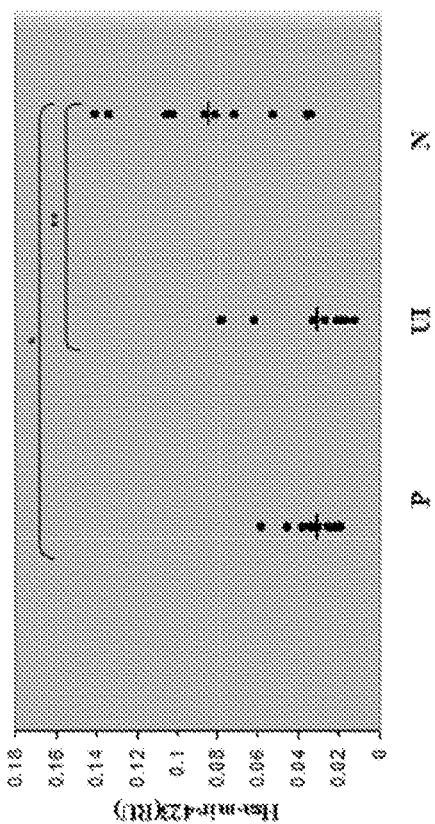
Figure 11F:
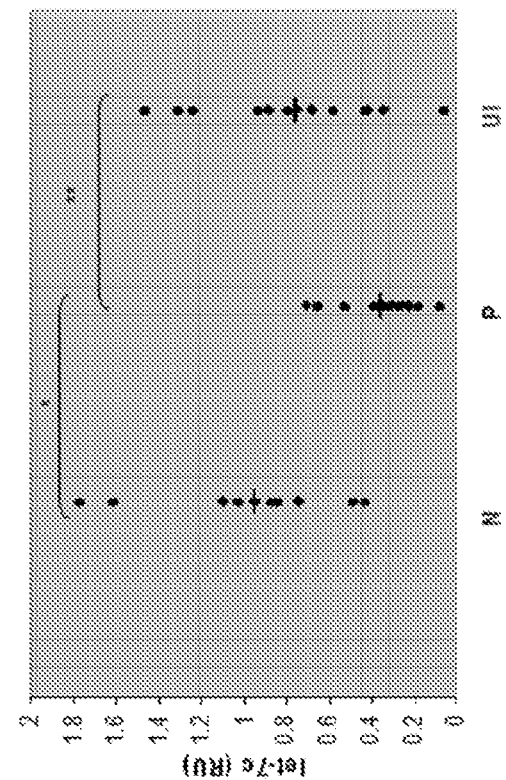
Figure 11E:
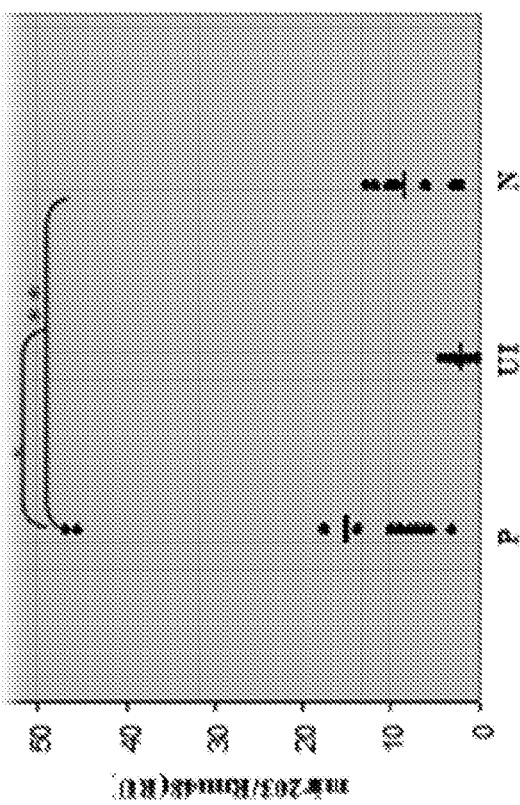
Figure 11G:
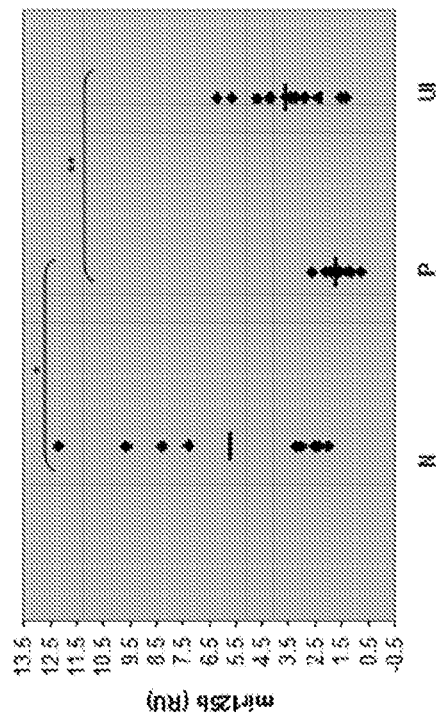

The results in psoriatic lesion showed a decrease in the expression of miR-197 (FIG. 11D) therefore it was important to determine the effect of hsa-miR-197 depletion on KC proliferation.

A knockdown of miR-197 using antago-miR (SEQ ID NO.: 71) did not affect the growth or proliferation of PHK cells (FIG. 2). The antago sequence acts as an miRNA inhibitor. The antago-miR, as purchased is a chemically modified, single-stranded nucleic acid designed to specifically bind to and inhibit endogenous microRNA (miRNA) molecules.

Example 2

IL-22 Enhances the Expression of miR-197

To study the cross-talk between miR-197 and IL-22 pathway, the expression of miR-197 was monitored in primary human KC (PHK) cells treated with different concentrations of IL-22.

Figure 3A:
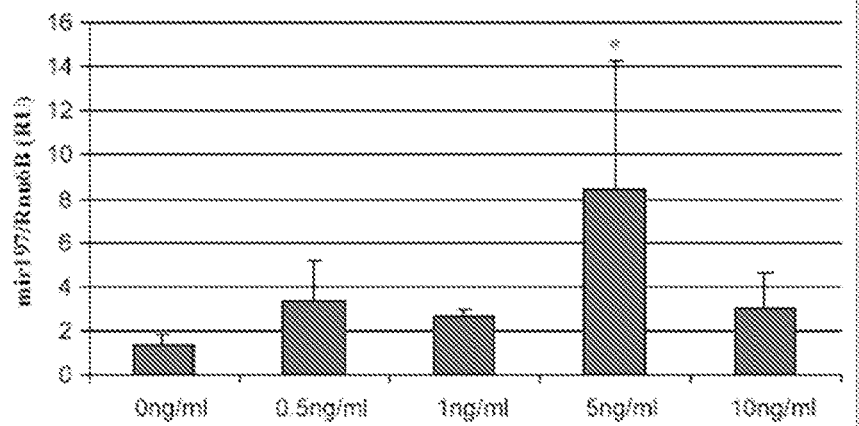
FIGS. 3A-B show the results of qPCR assays detecting mature miR-197 demonstrating that IL-22 enhances miR-197 [SEQ ID NO: 8] expression. IL-22 was added to PHK cells at the indicated concentrations. Cells were harvested and subjected to miR-197 specific qPCR (TaqMan-ABI).
Figure 3B:
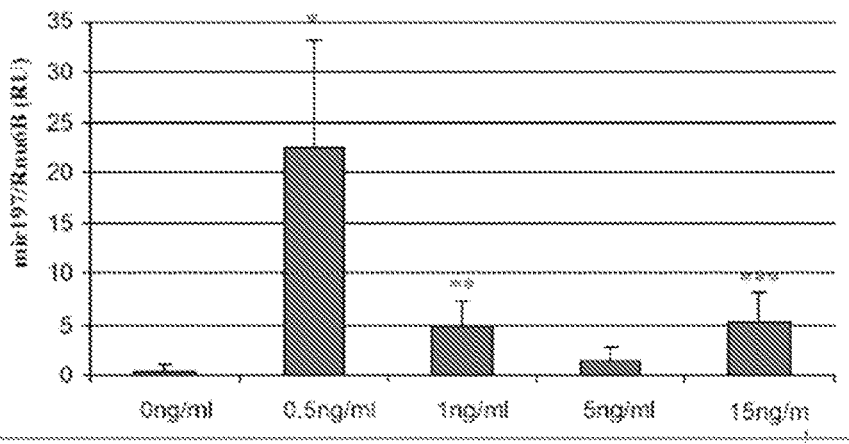

Results:

The levels of miR-197 increased significantly in cells treated with 5 ng/ml of IL-22 for 1 h or 0.5 ng/ml IL-22 for 48 h as compared to untreated cells (FIGS. 3A-B). These results indicate that IL-22 signaling enhances the expression of miR-197.

Example 3

STAT3 Mediates Between IL-22 and miR-197 Expression

Similar to other members of the IL-10 cytokine family, IL-22 utilizes JAK/STAT signaling, predominantly through activation of STAT3 24. To study whether miR-197 expression is directly regulated by the IL-22-STAT3 pathway, PHK were treated with a specific STAT3 inhibitor, S3I-201 31.

Figure 4A:
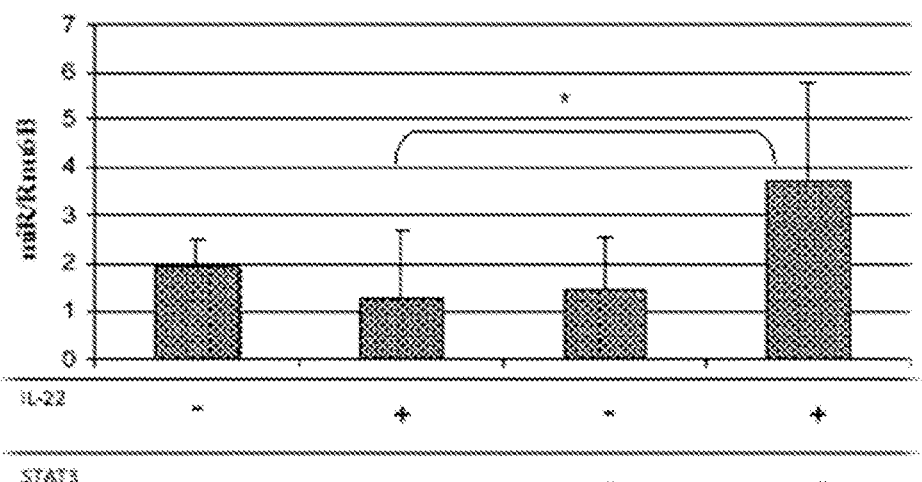
FIGS. 4A-C show that STAT3 binds to the putative promoter region of miR-197 after IL-22 treatment. STAT3 inhibitor (final concentration of 100 μM) was added to PHK 30 min after 5 ng/ml IL-22 was added.

Results:

S3I-201 prevents the IL-22-induced expression of miR-197 (FIG. 4A). These results indicate that the increase in miR-197 expression in response to IL-22 is mediated through STAT3. STAT3 is known to undergo phosphorylation and dimerization following IL-22 signaling, after which it binds to promoters and activates transcription of target genes. It was unknown if the promoter of miR-197 is a target of activated STAT3. The miR-197 gene is located on human chromosome 1p13.3, in a region distinct from other known transcription units.

Figure 4B:
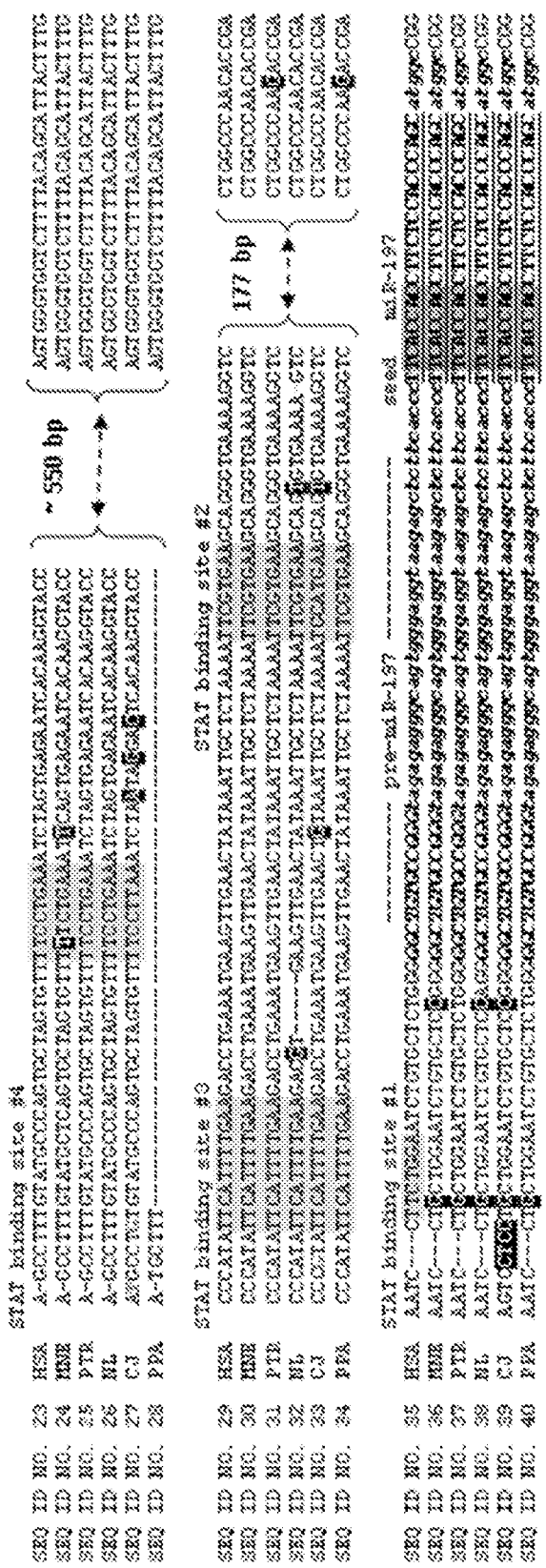
Figure 4C:
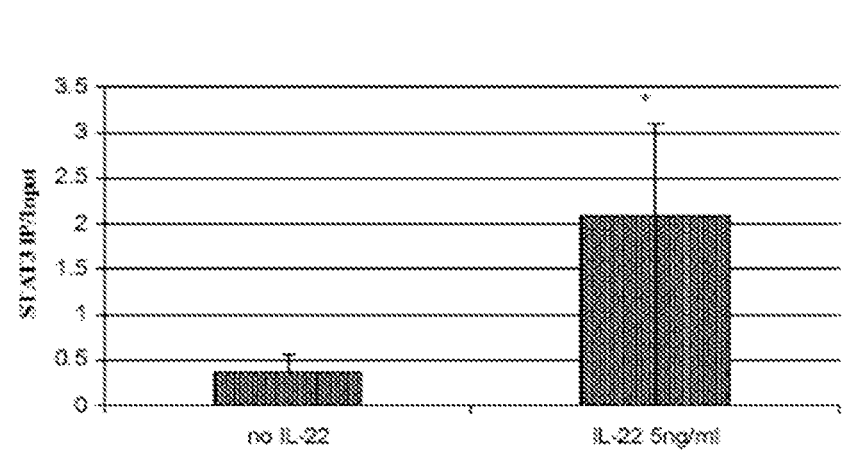

The bioinformatics tools Tfsitescan (Ghosh D. Object-oriented transcription factors database (ooTFD). *Nucleic acids research* 2000; 28: 308-10) and TFSEARCH (Heinemeyer T, Wingender E, Reuter I et al. Databases on transcriptional regulation: TRANSFAC, TRRD and COMPEL. *Nucleic acids research* 1998; 26: 362-7) mapped four putative STAT binding sites (TTN(4-6)AA) 35 within the ~2000 bases upstream of the miR-197 gene, its potential promoter (FIG. 4B). The sites designated #2, #3 and #4 are highly conserved among primates, suggesting that they are of evolutionary significance. Chromatin immunoprecipitation (ChIP) assay was used to examine if activated p-STAT3 binds to the putative miR-197 promoter sites following IL-22 treatment. The addition of IL-22 resulted in significant enrichment of precipitation of the miR-197 promoter area by p-STAT3 antibodies (FIG. 4C).

These results indicate that upon treatment of PHK by IL-22, activated STAT3 binds to the putative miR-197 promoter region.

Example 4

The IL22RA1 Subunit is a Direct Target of miR-197

IL-22 exerts its effects through a heterodimeric receptor complex consisting of IL22RA1 and IL-10RB. Bioinformatics analysis using the Web-based tool 'target scan' (www.targetscan.org) revealed that both subunits are potential targets of miR-197. Putative interactions of miR-197 with the IL22RA1 3'UTR and IL-10RB 3'UTR are shown in FIG. 5A and FIG. 6A-C.

To determine whether IL22RA1 or IL10RB are miR-197 targets, cells were co transfected with a plasmid containing the IL22RA1 3'UTR or the IL-10RB 3'UTR downstream of the luciferase reporter together with a miR-197 expressing plasmid, and luciferase reporter assay was performed 72 h later.

Figure 5B:
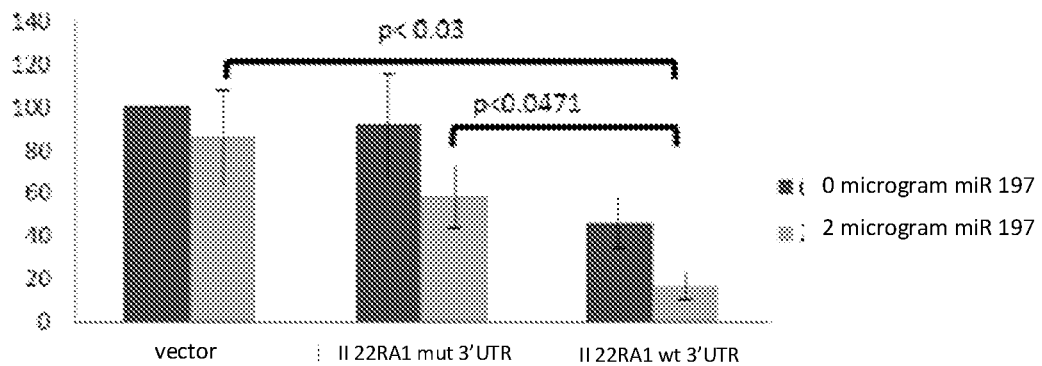

Luciferase expression was significantly lower in cells transfected with the luciferase-IL22RA1-3'UTR plasmid together with miR-197 expressing plasmid than in cells transfected with a plasmid lacking the 3'UTR of IL22RA1 (FIG. 5B).

To further explore miR-197 effect on IL22RA1, an IL22RA1-3'UTR-luc mutant was generated in which four nucleotides in the seed response sequence were changed from GUGGUGAA to GUaacaAA. The mutant was co-transfected with the miR-197 expression plasmid as before and luciferase activity was assessed. FIG. 5B (IL22RA1 mutant 3'UTR panel) clearly demonstrates that miR-197 has less effect on the mutated IL22RA1-3'UTR, proving that miR-197 seed sequence at the IL22RA1 3'UTR is essential for the regulation of IL22RA1 by miR-197. The same results were observed with 5 nM of pre-miR-197 RNA, as seen in FIG. 6C. This miR-197 repression was released in cells transfected with pre-miR-197 RNA together with antgo-miR-197 (FIG. 6C).

Figure 6B:
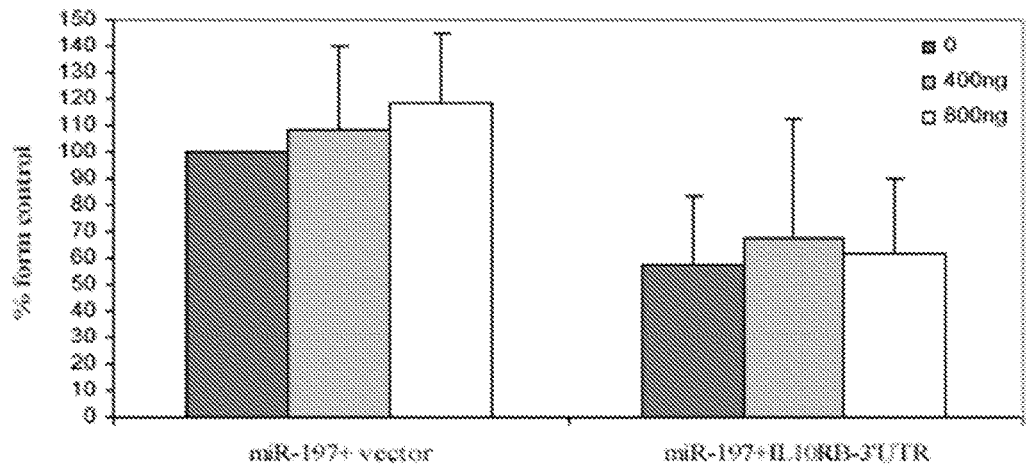
Figure 6C:
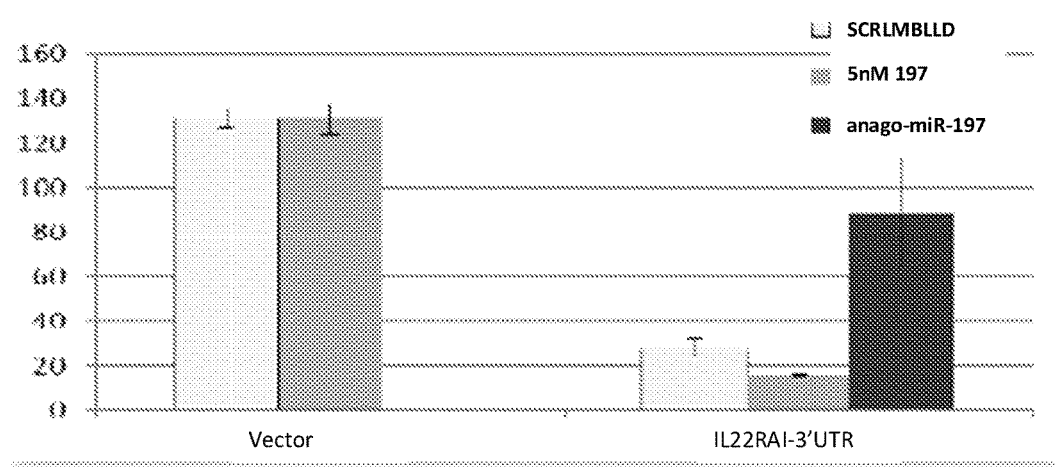

In contrast, the other subunit of the receptor to IL-22, IL10RB, seems not to be a target of miR-197, as indicated by the luciferase reporter assays with the IL10RB 3'UTR and miR-197 (FIG. 6B).

Figure 5C:
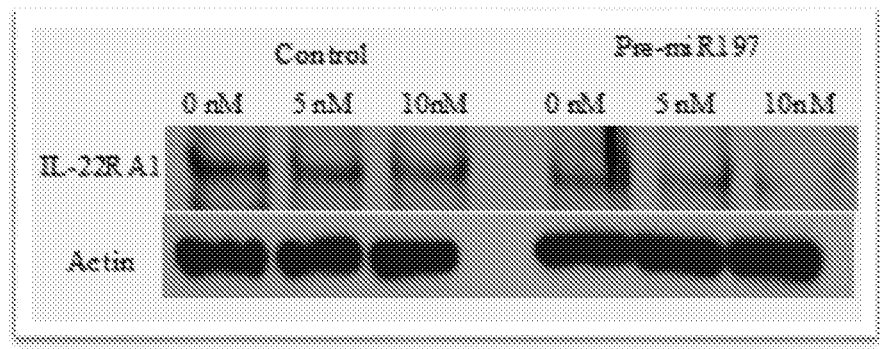
Figure 5D:
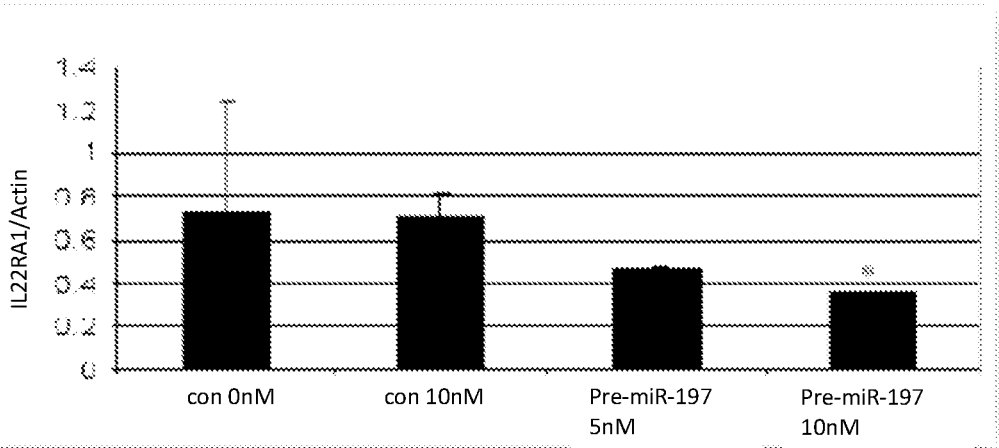

The effect of miR-197 on IL22RA1 expression was further examined by Western blot (WB) analysis. Over expression of pre-miR-197 in PHK cells led to a dramatic decrease in the level of IL22RA1 protein (FIGS. 5C and 5D). These results, taken together, indicate that IL22RA1 and not IL-1 ORB is a direct biochemical target of miR-197.

Example 5 miR-197 Inhibits the Effects of IL-22 on Keratinocyte (KC) Phenotypes

The results revealed that IL22RA1 is regulated by miR-197; moreover, the results strongly suggest that IL-22, activates the transcription of miR-197 through STAT3 signaling, thus generating a biochemical feedback loop as summarized in FIG. 7.

IL-22 enhances KC proliferation, increases the thickness of reconstituted human epidermis, inhibits KC differentiation and enhances KC migration. The results below show that these biological effects of IL-22 are affected by miR-197 overexpression.

Results:

The BrdU incorporation in IL-22 treated HaCaT-miR-197 or HaCaT-HTR was measured, and found to be significantly higher in the HaCaT-HTR cells (FIG. 8A).

Figure 8B:
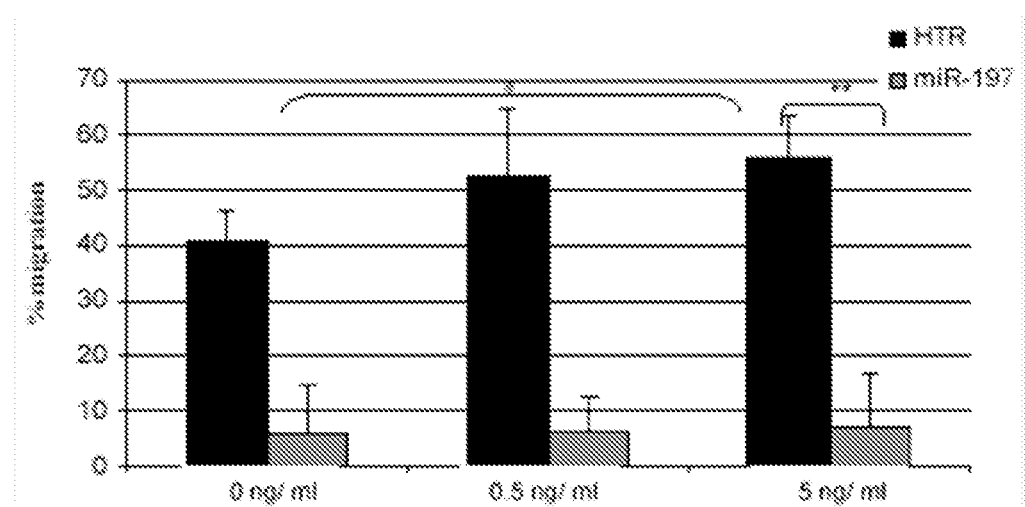
Figure 8C:
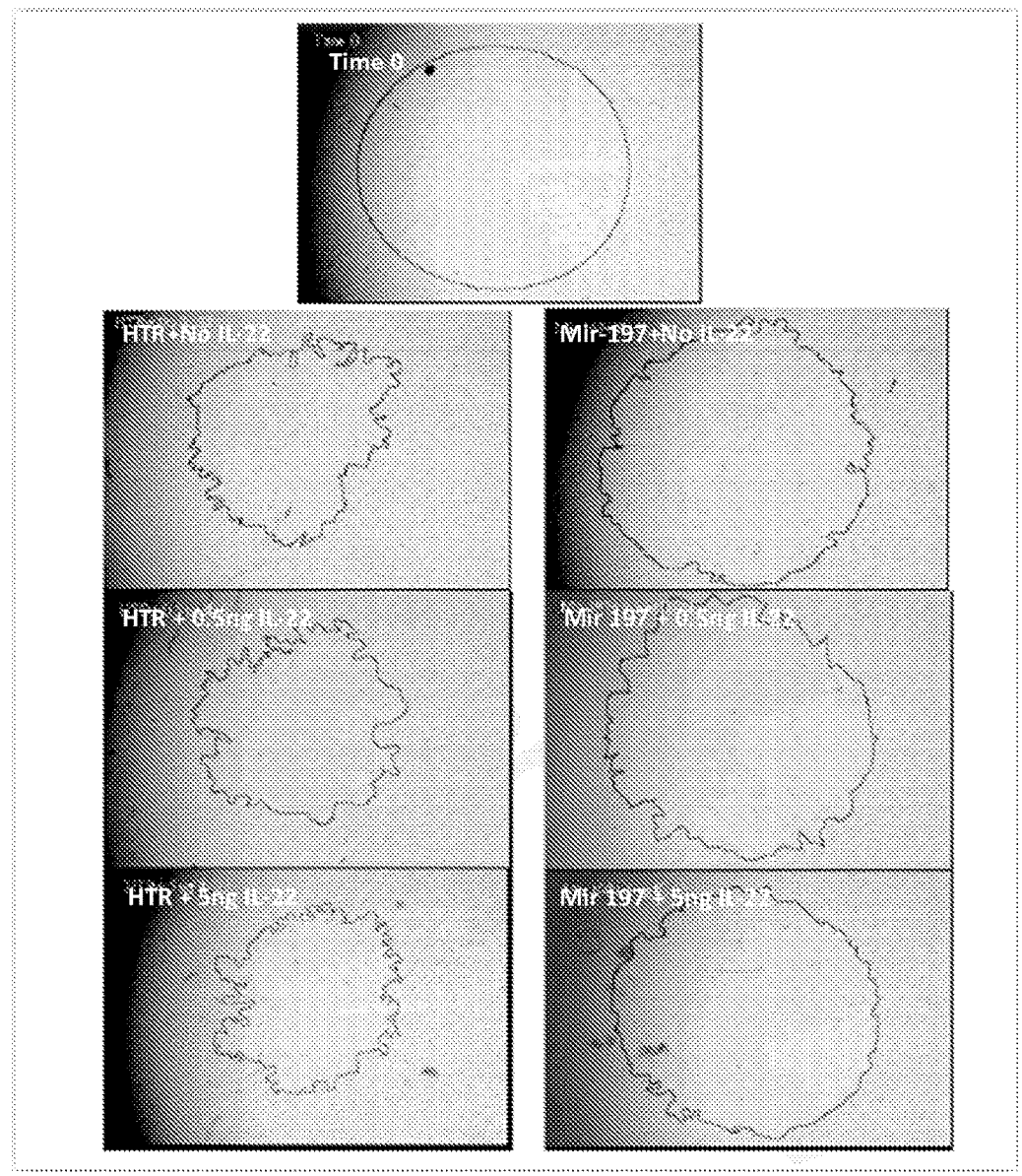

In order to evaluate the effect of miR-197 over-expression on IL-22-induced cellular migration, an in vitro cell migration assay in HaCaT-miR-197 vs. HaCaT-HTR was conducted. After seeding, cells were serum starved for 24 h, next IL-22 was added for additional 48 h and cells were fixed. The control HTR-HaCaT migrated to cover 40% of the empty area. The addition of 0.5 or 5 ng/ml IL-22 in the serum free medium led to an increase in the covered area of 52% and 56%, respectively, signifying IL-22-induced motility. HaCaT-miR-197 had a significantly lower level of baseline migration, covering only 5-10% of the empty area at 48 h, without any significant change in migration following IL-22 treatment (FIG. 8B).

Figure 2A:
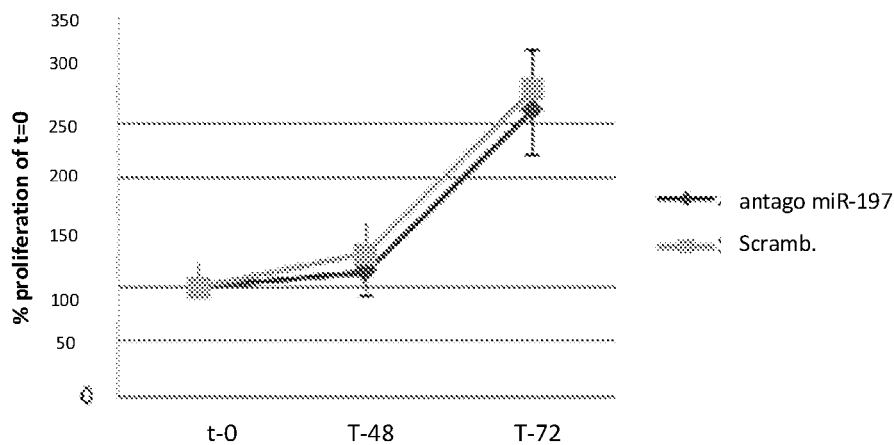
FIGS. 2A-C show the effect of antago-miR-197 on keratinocyte (KC) proliferation. Antago-miR-197 (SEQ ID NO.: 71; Life Technologies # MH10354) is an inhibitor miRNA comprising a chemically modified, single-stranded nucleic acids designed to specifically bind to and inhibit endogenous microRNA (miRNA) molecules. Primary human keratinocytes (PHK) cells were transfected with antago-miRNA-197 or scramble control. 24 h later cells were treated or not with the indicated IL-22 concentrations. Next, BrdU incorporation assays were performed.
Figure 2B:
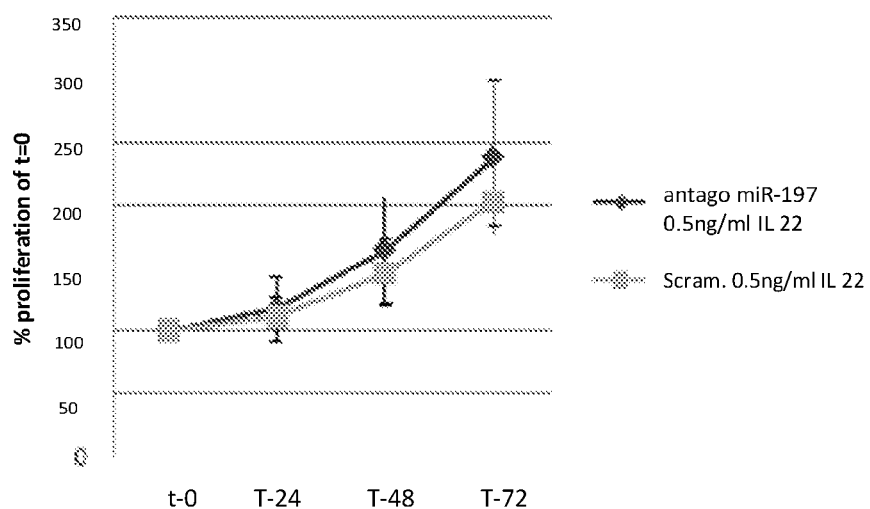
Figure 2C:
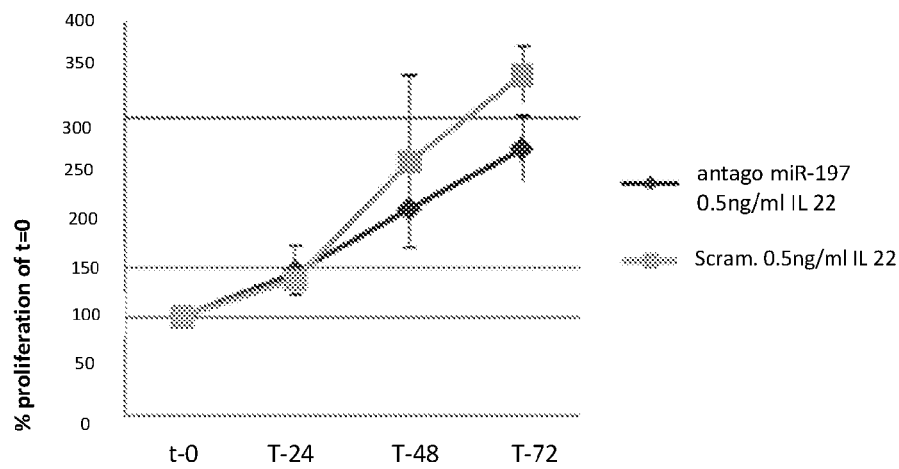

In parallel PHK cells were treated with antago-miR-197 (SEQ ID NO.: 71), in the presence or absence of IL-22. The results suggest that the antago-miR-197 had no significant effect on KC proliferation (FIGS. 2A-C).

The miRNAs role as "fine-tuner" might explain the fact that in high over-expression of repressor miRNA, e.g., miR-197, induced biological effects, however down regulation of one out of many "fine tuners" had no biological effect.

Example 6

DNA Methylation of the miR-197 Promoter Regions

Array studies showed mir-197 expression is significantly decreased in psoriatic lesions. The above results suggested the existence of a novel biochemical inhibition loop; IL-22, as previously shown, through IL22RA1-IL10RB, activates STAT3 which then enhanced the expression of miR-197, and miR-197 targets the expression of IL22RA1, thereby closing the biochemical feedback loop. However, despite the high levels of IL-22 in the blood of psoriatic patients and high expression of IL22RA1 in psoriatic patients' skin, the expression of miR-197 is decreased in their KC.

Recent work suggests that DNA methylation in the skin is dynamic and it changes along the epidermal layers and in specific genes. DNA methylation is capable of regulating both gene repression and activation, and the basal status of promoter methylation is important for individual genes expression. A recent study comparing differences in the DNA methylation, between psoriatic lesions and uninvolved or normal skin revealed many CpG sites with differential methylation levels.

Figures 9A, 9B:
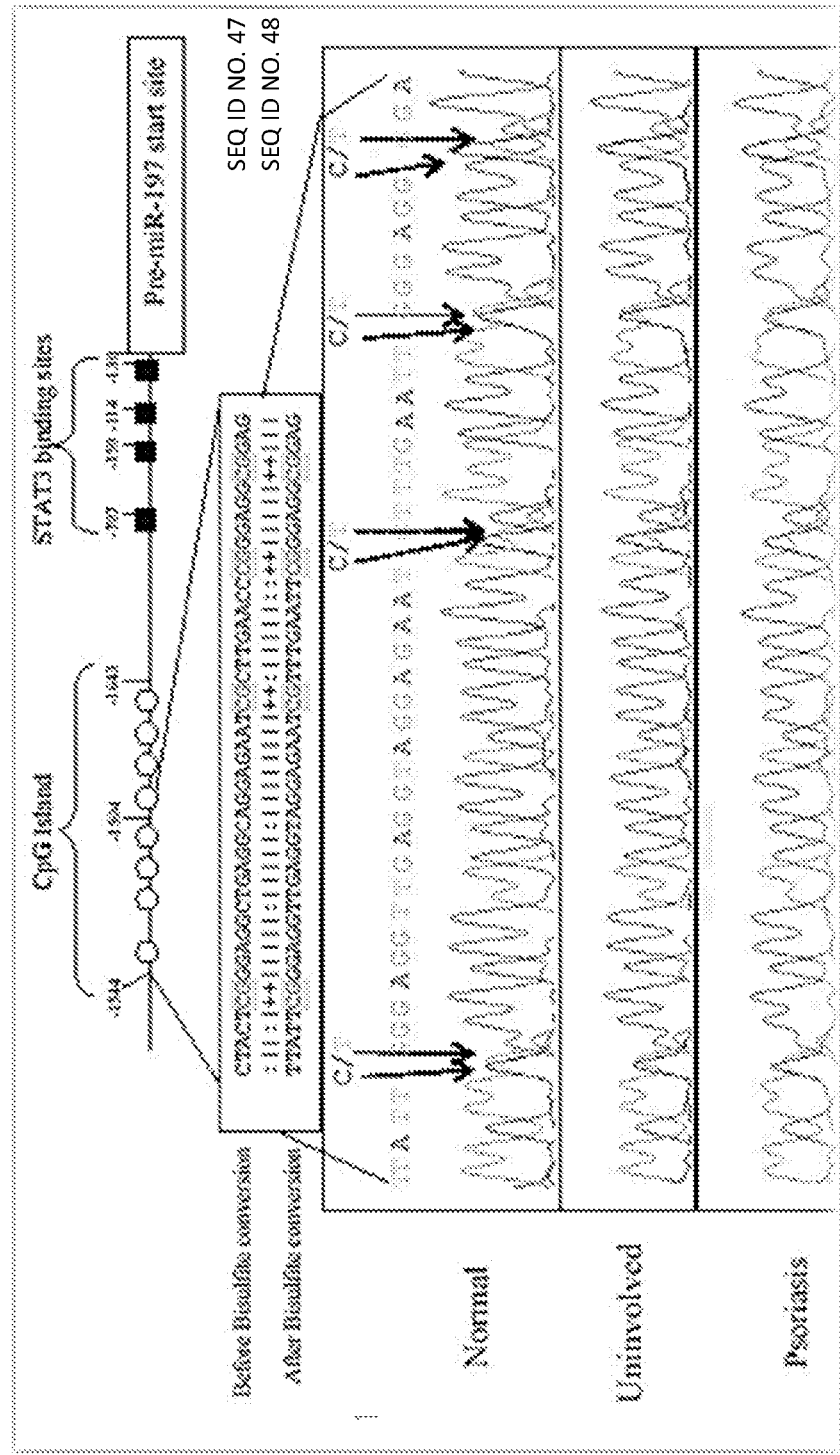
FIGS. 9A-B show the cytosine methylation pattern in psoriatic and normal skin.
Figure 10A:
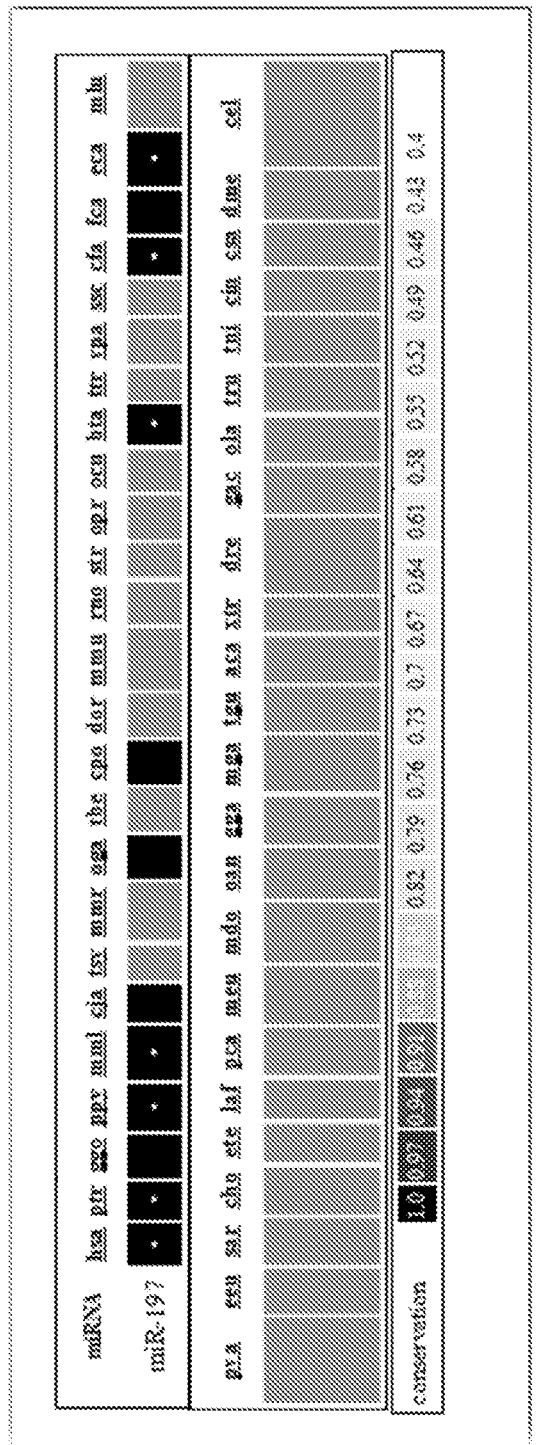

The next step was to test how cytosine methylation of the miR-197 promoter in psoriatic lesion compared to normal skin might be different and thereby explain why miR-197 is silenced in psoriasis despite the high levels of IL-22 in the patients' blood. The ~2000 bases up stream of the pre-miR-197 sequences comprise the regulatory elements of promoter and contain one CpG island (FIG. 9A).

The DNA methylation state of this region was analyzed in biopsies from formalin fixed paraffin embedded (FFPE), of psoriatic lesions, uninvolved psoriatic skin and normal skin. Each sample was subjected to at least two sequencing analyses. FIG. 9B clearly shows that the methylation pattern of the mapped CpG islands in the miR-197 promoter, in psoriatic samples is similar to that found in normal skin.

Example 7

Quantification of miRNA Expression in Psoriatic Lesions or Psoriatic Uninvolved Skin Initial qualitative PCR array studies showed up-regulation and down-regulation of a number of specific MiRNAs in psoriasis lesions compared with normal skin (data not shown). Since the expression levels provided by the arrays were not quantified results, real time quantitative real-time-PCR (QRT-PCR) was performed in a follow-up study on some of the miRNAs in large number of samples; 13 psoriasis samples and 10 normal skins.
Results:
The QRT-PCR results are shown in FIGS. 11A-G: (FIG. 11A) miR-99a, (FIG. 11B) miR-150, (FIG. 11C) mir-423-3p, (FIG. 11D) miR-197, (FIG. 11E) miR-203, (FIG. 11F) Let7c, and (FIG. 11G) miR-125b-2. RNA from normal skin (N), psoriatic lesion (P), or psoriatic uninvolved skin (UI) was isolated. QRT-PCR analysis was performed and normalized by Rnu48. Calculations were done with Data Assist software (Applied Biosystems). Y axis bars are arbitrary units that define fold change. Each dot represents one sample and the average is denoted by a horizontal line. Standard errors were calculated from the means of 13 psoriasis samples and 10 normal skins (asterisks represent statistical significance change).

As can been seen, the expression pattern is not homogeneous, some miRNAs were down regulated in the psoriatic lesions ((FIG. 11A) miR-99a; (FIG. 11B) miR-150, (FIG. 11C) miR-423; (FIG. 11D) miR-197, (FIG. 11F) miR-Let7c and (FIG. 11G) miR-125b-2) while others were up regulated ((FIG. 11E) miR-203) in the psoriatic lesions compared to normal skin or uninvolved skin.

Example 8

Let-7c Regulates IGF1R

IGF1 signaling and IL-22 signaling are both over active in psoriasis lesions. Further, IGF-1R has been shown to be a target of miR-99a. miRNA is transcribed as a cluster along with has-let-7c and has-mir-125b-2 from a common intron of the LINC00478 long intergenic non-protein coding RNA also known as C21orf34, whose function is unknown (data not shown).

Figure 12A:
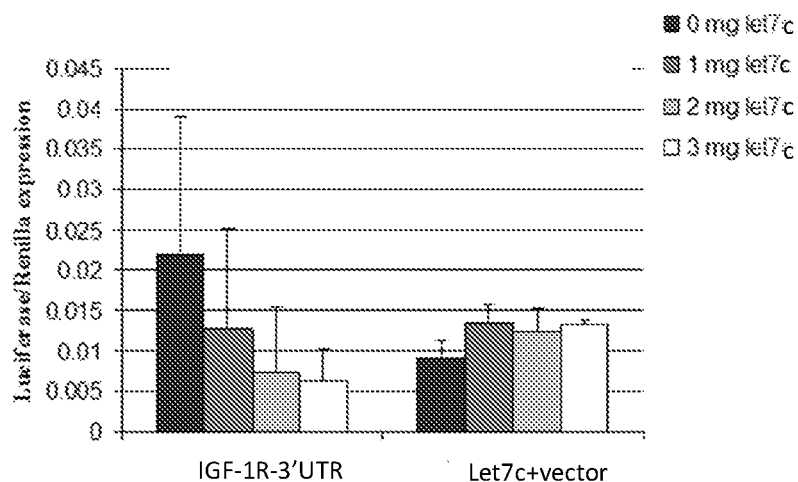
FIGS. 12A and 12B show that IGF-1R 3'UTR is a target of Let7c.

To understand the biological role of Let-7c and its involvement in psoriasis, regulation of IGF1R as a possible targets mRNA was investigated. MiRNAs regulate gene expression mainly through interaction with the UTR of a specific target mRNA. The binding specificity is directed by what is known as the miRNA 'seed' sequence: miRNA seeds are 7 to 8 nucleotides at the end that serve as the primary determinant of target specificity.
Results:
FIG. 12A presents data from cells that were co-transfected with a Luciferase-vector (let7c+vector) or a Luciferase-IGF1R-3'UTR vector (IGF1R-3'UTR), concomitant with a Let-7c expressing plasmid at different concentrations, 0 mg, 1 mg, 2 mg and 3 mg. Each experiment was done in triplicates. The results show down regulation of expression from the IGF1R-3'UTR in the presence of Let-7c expression at all concentrations.

Figure 12B:
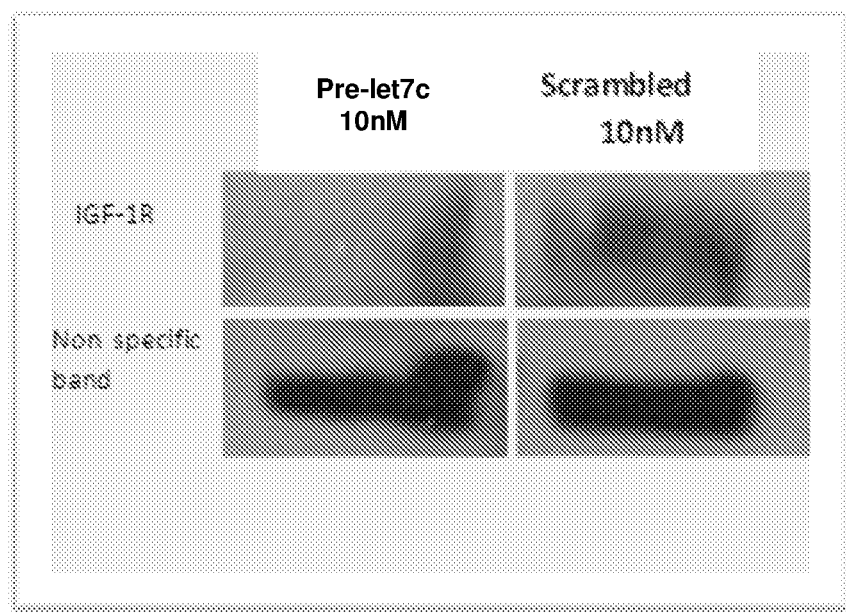

FIG. 12B presents data from primary human keratinocytes (PHK) transfected with 10 nM pre-let7c [SEQ ID NO: 12] or an S-scrambled oligo (Ambion) and harvested 120 hours post transfection. Based on information available from Ambion, the scrambled sequence is a random miRNA mi I molecule that has been extensively tested in human cell lines and tissued and validated to not produce identifiable effects on known miRNA function. Cell samples were subjected to Western Blot analysis with IGF-1R antibodies (top row). The results show an absence of IGF-1R expression in PHK transfected with pre-let7c [SEQ ID NO: 12] These results show that Let7c regulates IGF-1R expression and suggests that Let7c miRNA may be a key regulator of skin homeostasis since IGF-1R has been shown to have a major role in keratinocyte differentiation.

Example 9

Correlation Between miRNA Expression and IGF1 Concentration

Figure 13A:
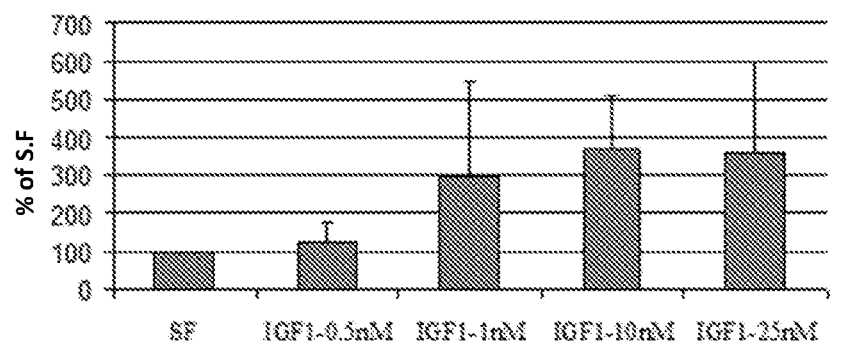
FIGS. 13A-C show the miRNA expression of human mir-99a (13A), mir-125b-2 (13B) and mir-Let7c (13C) with increasing concentrations of IGF1. Mir-99a (13A) and mir-125b-2 (13B) showed significant increase of expression with increasing IGF1 concentrations.
Figure 13B:
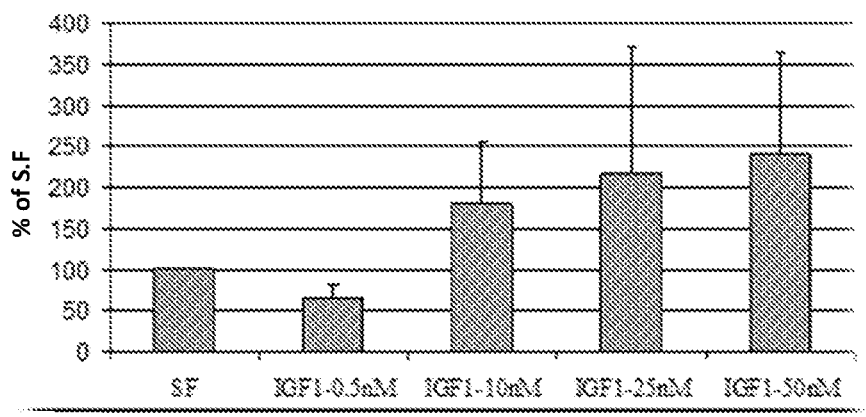
Figure 13C:
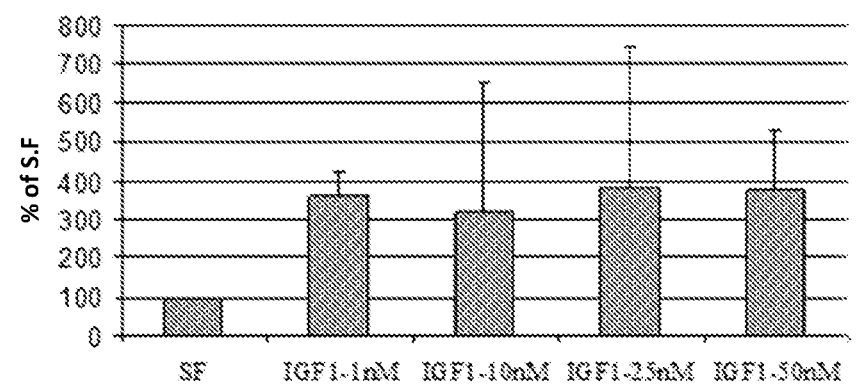

Next, the relationship between the clustered miRNAs: mir-99a, mir-125b-2 and mir-Let7c and IGF-1R was investigated. FIGS. 13A-C present the results of mir-99a, mir-125b-2 and mir-Let7c expression in serum starved PHK cells treated with increasing concentrations of IGF1 (0.5 nM, 1 nM, 10 nM and 25 nM). PHK cells were serum starved for 48 h, at which time IGF1 at the indicated concentration was added, or not (SF). Seventy-two (72) hours following the addition of IGF1, cells were harvested, total RNA extracted and subjected QRT-PCR for hsa-mir-99a expression (13A; *p=0.0027 **p=0.04510), hsa-mir-125b2 expression (13B; *p=0.0414) or has-mir-let7c expression (13C).
Results:
The expression of miR-99a and mir-125b-2 were significantly increased in cells treated with 1-25 nM of IGF1 as compared to untreated cells (FIGS. 13A and 13B). These results suggest that miR-99a and mir-125b-2, and IGF-1R are co-regulated, functioning together to maintain the balance between keratinocyte proliferation and differentiation. The change in expression of mir-Let7c, while greater than in the absence of IGF1, did not appear to be correlated with increasing concentrations of IGF1 (FIG. 13C).

Example 10

Correlation Between miRNA Expression and IL-22 Concentration

Figure 14A:
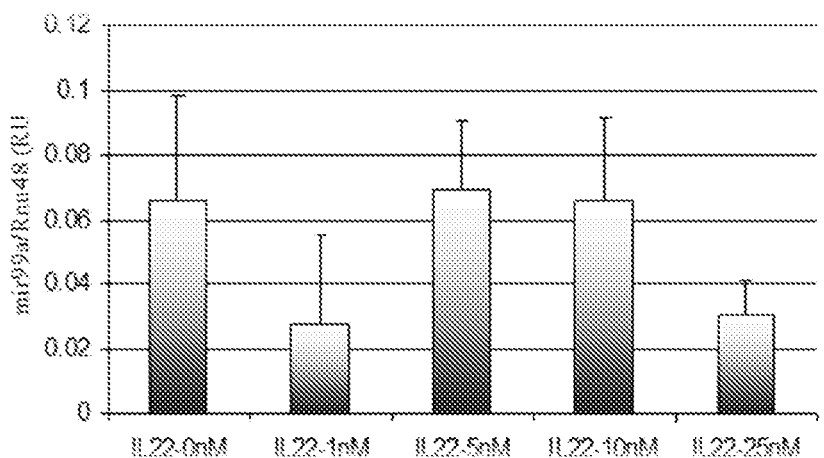
FIGS. 14A-D show the miRNA expression of human mir-99a (14A), mir-125b-2 (14B) and mir-Let7c (14C) with increasing concentrations of IL-22 after 48 hours incubation.
Figure 14B:
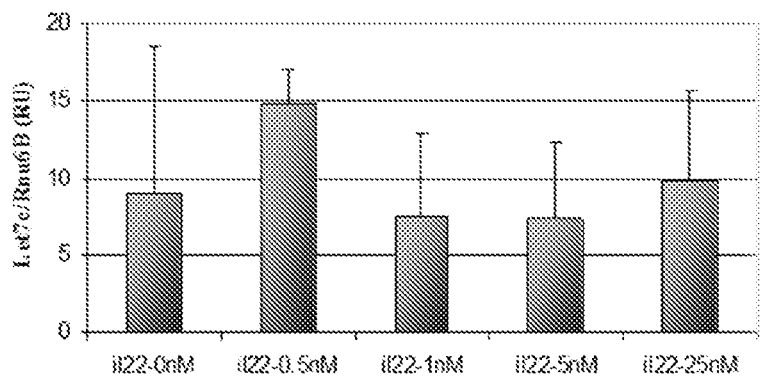
Figure 14C:
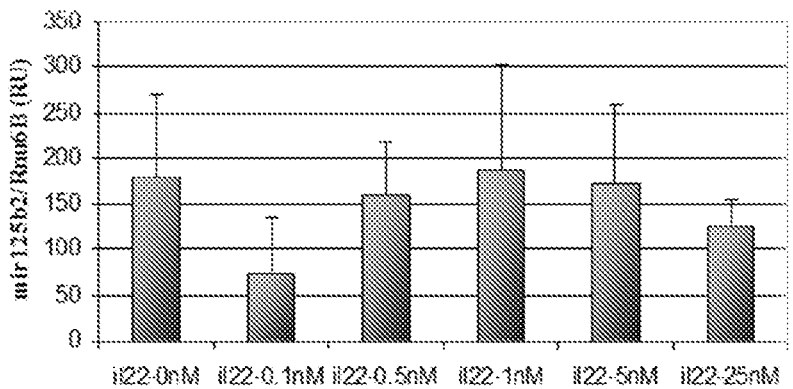
Figure 14D:
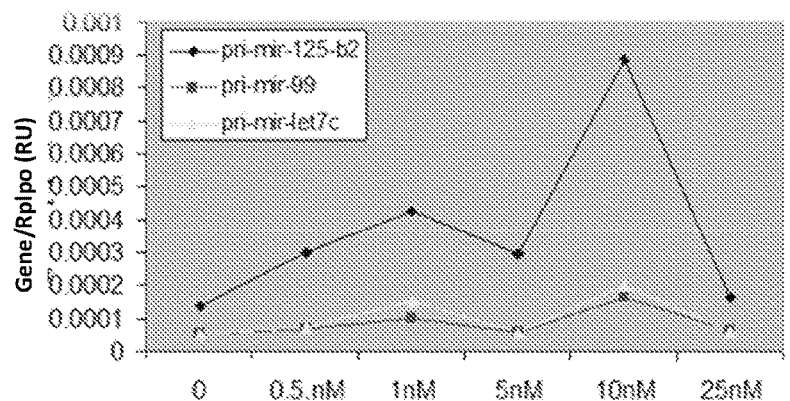

The relationship between the clustered miRNAs: mir-99a, mir-125b-2 and mir-Let7c and IL-22 was investigated in PHK cells. FIGS. 14A-D present the results of mir-99a, mir-125b-2 and mir-Let7c expression in PHK cells treated with increasing concentrations of IL-22 (0.00 nM, 0.1 nM, 0.5 nM, 1 nM, 5 nM, 10 nM and 25 nM) for 48 hours. Cells were then harvested, total RNA was extracted and subjected to QRT-PCR for hsa-mir-99a expression (14A), has-mir-let7c expression (14B), or mir-125b2 expression (14C). QRT-PCR was performed with a Taqman qPCR kit specifically designed for the listed genes, and normalized by Rnu48 or Rnu6B. FIG. 14D shows all three miRNAs expression after just 1 hour of treatment with IL-22 at the indicated concentrations. The results presented are based on three (3) independent experiments.

Results:

The results presented in FIGS. 14A-D show that miR-197 is activated by IL-22 at a specific range of concentrations. Small changes in IL-22 concentration have a dramatic effect on the expression levels of miR-197 and thereby on the levels of IL22RA1 protein.

Example 11

Correlation Between IGF1 Signaling and IL-22 Signaling and Some miRNAs

Figure 15:
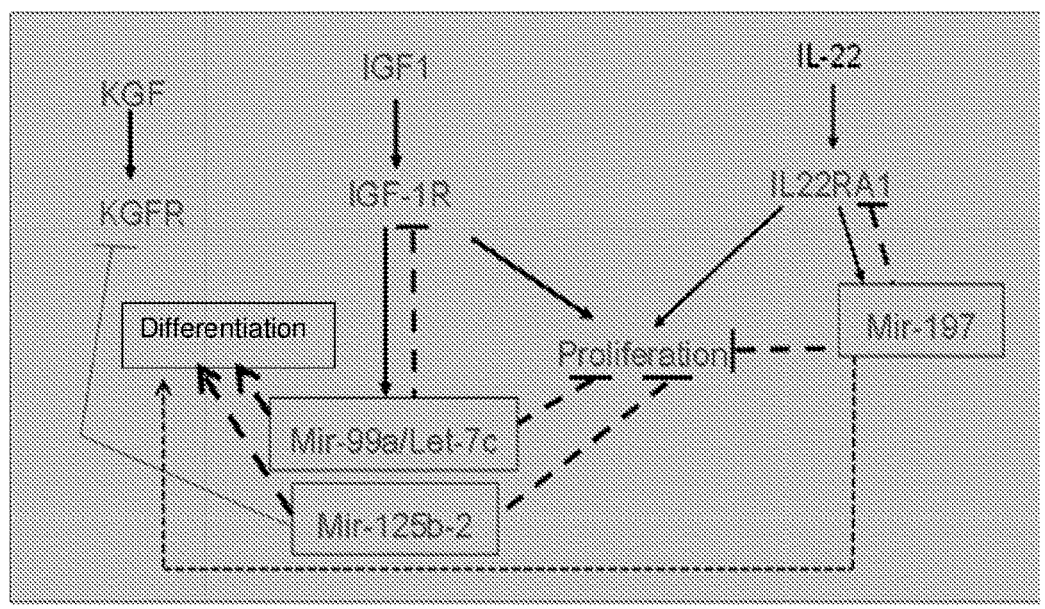
FIG. 15 presents a schematic model representing the correlation between IGF1 signally, IL-22 signaling and four different human miRNAs: Mir-99a, Let7c, Mir-125b-2 and Mir-197.

FIG. 15 summaries the results on the correlation between IGF1 signaling and IL-22 signaling and some of the miRNAs: Mir-991, Let-7c, Mir-125b-2 and Mir-197, found show differential expression in psoriasis compared to normal skin. The results presented in Example 7, FIGS. 11A, 11D, 11F, 11G, show that these miRNAs are each down regulated in psoriasis lesion.

FIG. 15 presents a scheme model representing the correlation between IGF1 signaling and IL-22 signaling and miRNAs. IGF1 actives the IGF-1R that was shown to inhibit keratinocytes differentiation and have activating role in the keratinocytes proliferation. The results suggest that IGF-1R signaling enhances the expression of mir-99a, let7c and miR-125b-2. MiR-99a, and Let-7c can target IGF-1R and inhibit its expression; in parallel both inhibit proliferation and active differentiation. Mir-125b-2 was also activated by IGF1 and has been shown to target the keratinocytes growth hormone receptor (KGFR). The IL-22 signaling activated through the 11-22 receptor (IL22RA1 is of its one subunit). In parallel it was found that this signaling up regulated the expression of mir-99a, Let-7c, miR-125b-2 and miR-197. miR-197 can regulate the expression of the IL22RA1, and repress proliferation and active differentiation.

Example 12

The IL17RA Subunit is a Direct Target of miR-197

Figure 16A:
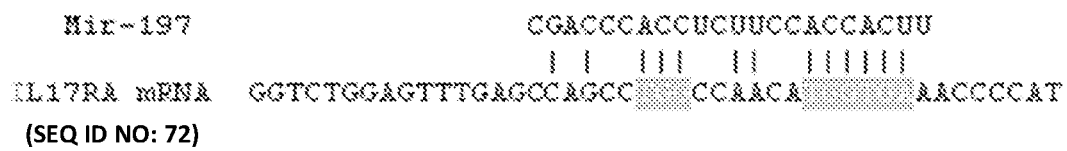
FIGS. 16A-16C show that IL17RA, a subunit of the receptor to IL-17A, is a biochemical target of miR-197. Putative interactions sites between miR-197 and IL17RA 3'UTR are shown in FIG. 16A, wherein the shaded areas indicate putative clusters of interaction sites.

Putative interactions of miR-197 with the IL17RA 3'UTR is shown in FIG. 16A.

To determine whether IL17RA is a real miR-197 target, cells were co transfected with a plasmid containing the IL17RA 3'UTR downstream of the luciferase reporter together with a miR-197 expressing plasmid, and luciferase reporter assay was performed 72 h later.

Figure 16B:
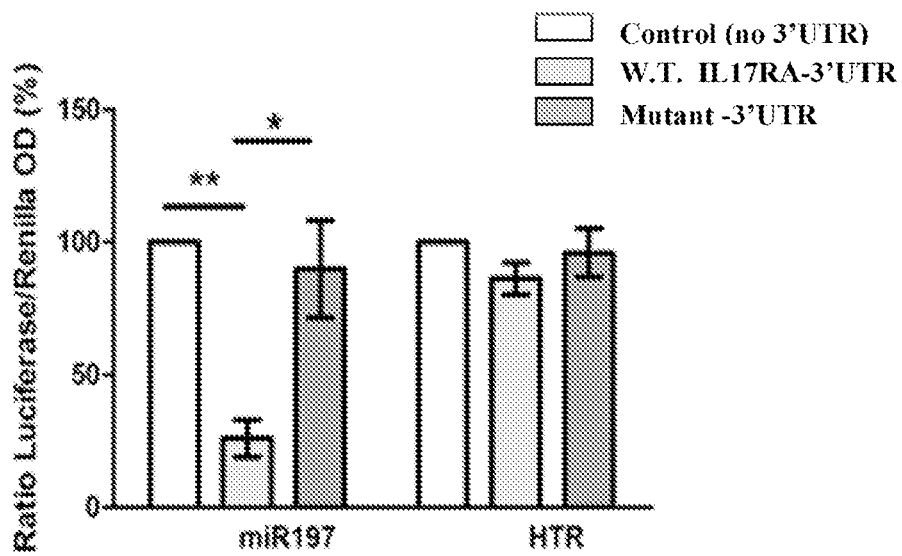

Luciferase expression was significantly lower in cells transfected with the luciferase-IL117RA-3'UTR plasmid together with miR-197 expressing plasmid and in cells transfected with a plasmid lacking the 3'UTR of IL17RA (FIG. 16B).

To further explore miR-197 effect on IL17RA, an IL17RA-3'UTR-luc mutant was generated in which 11 nucleotides in the seed and the putative binding site response sequence were changed from GCCAGCCTGGC-CAACATGGTGAAACCCCAT (SEQ ID NO: 73) to GCGATCCTCCCCTTCATCCACATACCCCAT (SEQ ID NO: 74). The mutant was co-transfected with the miR-197 expression plasmid as before and luciferase activity was assessed. FIG. 16B (IL17RA mutant 3'UTR panel) clearly demonstrates that miR-197 has a lost its effect on the mutated IL17RA-3'UTR, proving that miR-197 seed sequence at the IL17RA 3'UTR is essential for the regulation of IL17RA by miR-197.

Figure 16C:
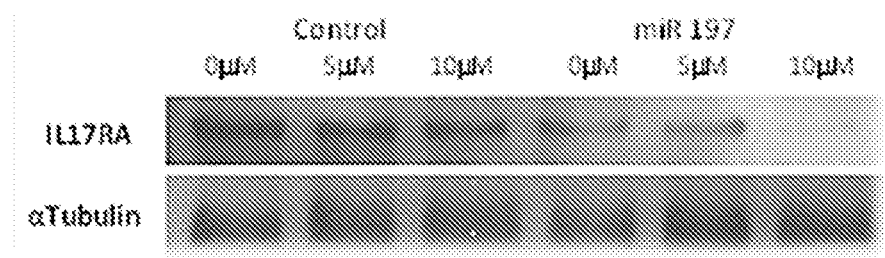

The effect of miR-197 on IL17RA expression was further examined by Western blot (WB) analysis. Over transfection of pre-miR-197 mimic RNA into cells led to a dramatic decrease in the level of IL17RA protein (FIG. 16C). These results, taken together, indicate that IL17RA is a direct biochemical target of miR-197.

As described above IL-17A up-regulates the expression of numerous inflammation-related genes in target cells, one of the main target of IL-17A is the CCL20 gene.

Figure 17:
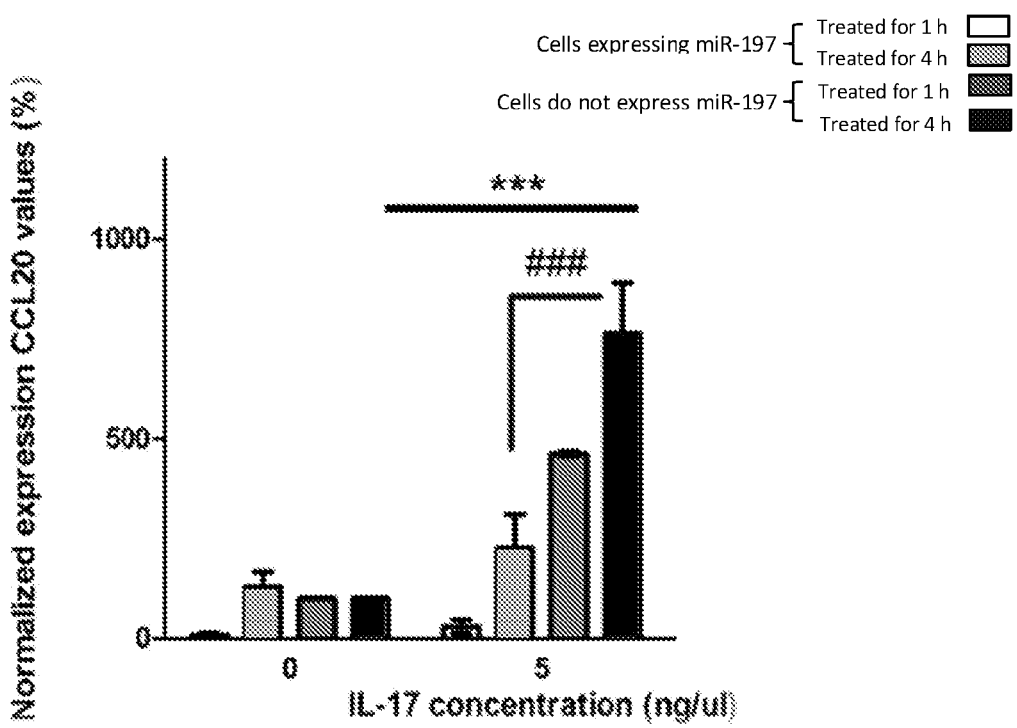
FIG. 17 shows induction of CC120 expression by IL-17A is inhibited by miR-197.
Figure 18:
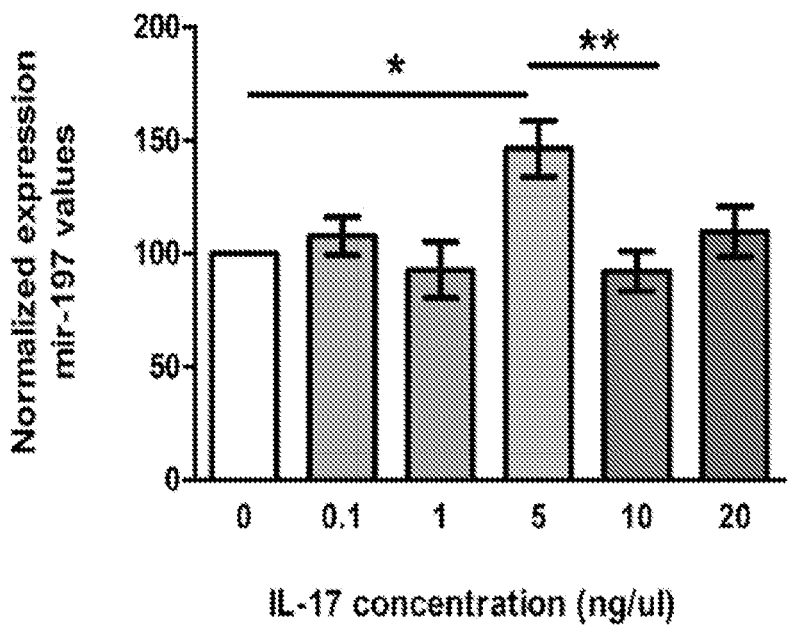
FIG. 18 shows that IL-17A activates the transcription of miR-197.

The results presented in FIG. 17 show that miR-197 inhibits the effect of IL-17A on the expression of CCL20 in keratinocyte (KC).

The results revealed that IL17RA is regulated by miR-197. Moreover, it was found that IL-17A, activates the transcription of miR-197 thus generating a biochemical feedback loop as summarized in and FIG. 7, which broadens the scheme for miR-197 mechanism of action.

Example 13

Establishing and Validating an Animal Model of Human Psoriasis in SCID Mice

Figure 19A:
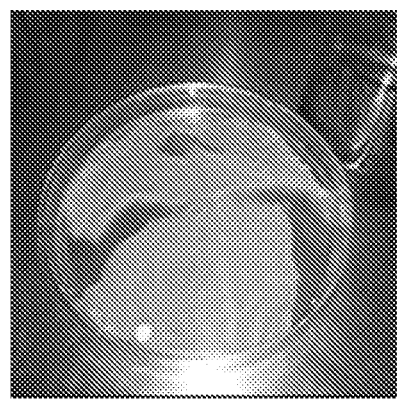
FIGS. 19A-19C present stages of establishing and validating a model of human psoriasis in SCID mice.
Figure 19B:
Figure 19C:

The current understanding of the role of miRNAs in skin biology comes from primary human keratinocytes (PHK) studies. To better understand the role of miRNAs in psoriasis and to pave the way for therapeutic application of these findings, in vivo research must be done. In the study described here, a model of human psoriasis was established and validated in the model SCID mice (FIGS. 19A-19C).

A Helsinki permit to use human skin obtained in operations of skin reduction was acquired and a permit (number 815) to perform these animal experiments was acquired from the Council for Experiments on animals at the Israeli health ministry application number 5528.

One of the phenotypes of psoriasis lesion is the very thick epidermis. Human skin that had been removed from, either psoriasis patient, or form healthy individual was transplanted onto mice lacking part of their immune system (C.B-17/IcrHsd-scid). 4-6 weeks after transplantation when the skin had been fully accepted into the transplant $3\times10^6$ activated psoriasis lymphocytes were injected into to transplanted skin. About two weeks later the formation of the psoriasis like plaques were observed.

The human skin present in the SCID mice develops typical psoriasis phenotype of scaled skin, as can be seen in FIG. 20A and FIG. 20B; histologically the skin resembles a psoriasis phenotype.

For the results presented in FIGS. 20A-20B, human psoriatic skin was used and activated T cells from psoriasis patient. From 250 ml of psoriatic patient' blood we isolated Peripheral blood mono-nuclear cells (PBMC) by regulate method (centrifugation overlayered on Histopaque 1.077). Next the cells were activated by adding to their growing medium 1 g Staphylococcal enterotoxin B (SEB) human IL-2, Cultured (37° C., 5% CO2) for 48 h.

However, the model could also be generated by transplanting normal human skin onto the mice and inject into it activated T cells from a psoriatic patient. This is an established model for psoriasis known as psoriatiform model. As can be seen in FIGS. 21A-21F, which is a comparison of the two models. Comparison of the full psoriatic (FIGS. 21A, 21C, 21E) and the psoriatiform (FIGS. 21B, 21D, 21F) models reveals the marked similarity between them. One of the phenotypes of the psoriasis lesion is the epidermal thickness. Towards this end, the epidermal area in the two models (psoriasis and psoriatiform) was measured. As can be seen in FIGS. 22A-22D), the epidermal thickness in the two models is similar.

Figure 23A:
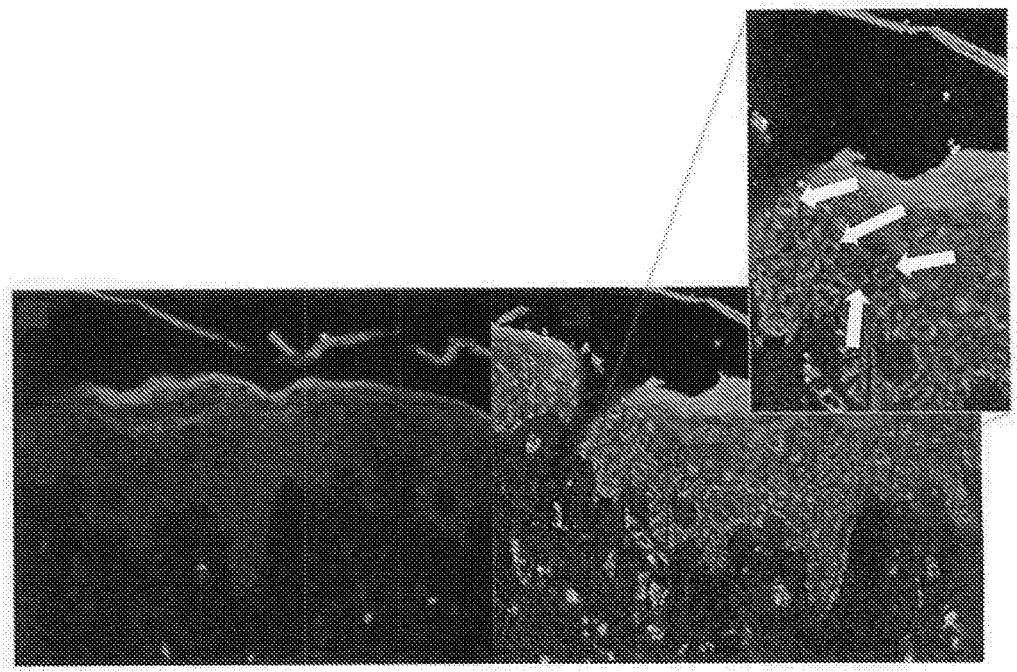
FIGS. 23A-23B shows fluorescent micrographs examining miR-197 penetration into implanted human skin models.
Figure 23B:
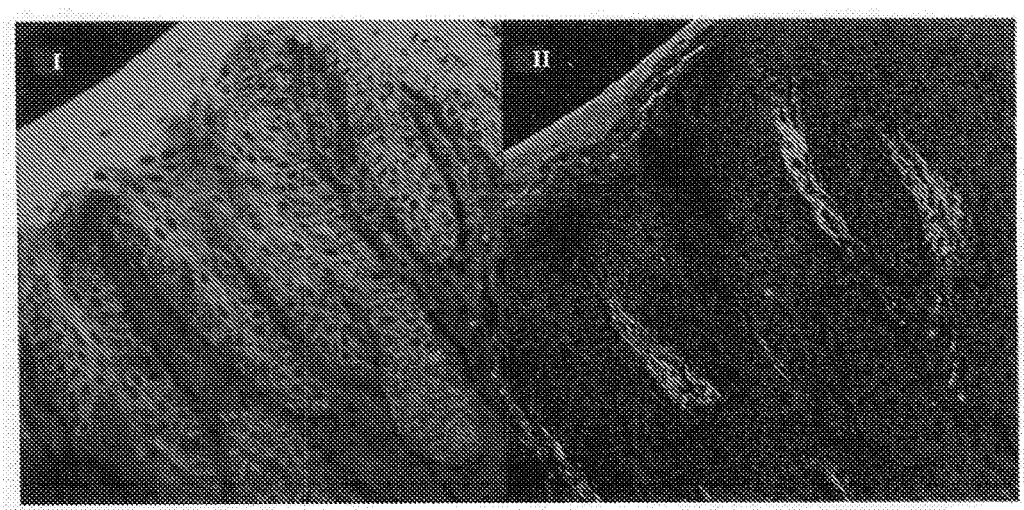
Figure 24:
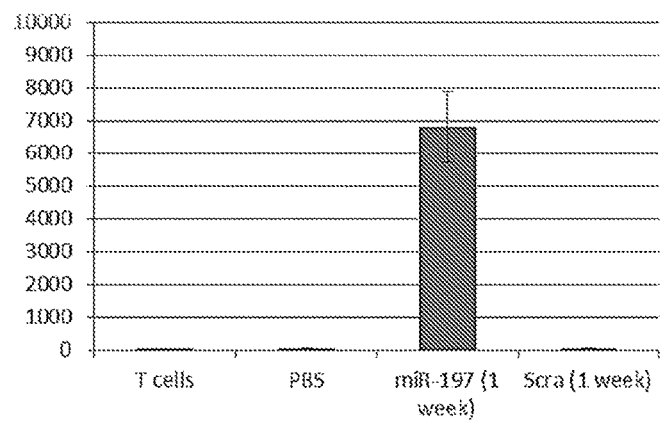
FIG. 24 presents a bar graphs showing the expression of miR-197 in the biopsies taken from the mouse model 1 week after the specified treatment. Mice were divided into 4 groups, 3 mice in each. In the first group activated psoriatic T cells were injected to the implanted skin, without further treatment (T cell). In the second group PBS was injected into the implanted skin (PBS). In the third group of mice activated psoriatic T cells were injected in the implanted skin and the lesions were pre-sonicated until the right conductivity was achieved and next miR-197 was applied on top of the lesions (miR-197). In the fourth group of mice activated psoriatic T cells were injected to the implanted skin, the lesions were pre-sonicated and scrambled RNA was applied on top of the lesions (Scra). All treatments were as single exposures. All groups were sacrificed after a week; biopsies were taken from the implanted skins and RNA was extracted and subjected to qRT-PCR with specific primers to miR-197.

The next step was to insert miR-197 into the psoriasis lesion and observe the results. As can be seen in FIGS. 23A-23B, successful penetration was observed (FIG. 23B) compared to no penetration of the labeled miRNA (red) in the control (FIG. 23A). The same result was confirmed through the direct measurement of miR-197 in the skin biopsies in the same model (FIG. 24). Moreover, it was observed that in cells transfected by the miRNA (red) there is a significant reduction of the IL22RA1 staining (green), (compare FIG. 23A to FIG. 23B).

The findings presented here prove that the delivered mir-197 is biochemically active.

Example 14 miR-197 Provides a Biological and Therapeutic Effect on Psoriasis Lesions

After it was determined that once miR-197 had penetrated the skin, it remained biochemically active, that experiments were begun to find out whether miR-197 has a biological therapeutic effect on psoriasis lesions. In the next experiment the psoriasis model was generated in 19 mice which were divided into 4 groups. In the first group, activated psoriatic T cells were injected to the implanted skin, without further treatment. In the second group, PBS was injected into the implanted skin. In the third group of mice, activated psoriatic T cells were injected in the implanted skin and the lesions were pre-sonicated until the right conductivity was achieved and next miR-197 in Q Starch delivery agent was applied on top of the lesions as a single exposure. In the fourth group of mice, activated psoriatic T cells were injected into the implanted skin, the lesions were pre-sonicated and scrambled RNA (scra) in Q Starch delivery agent, which was applied on top of the lesions as a single exposure. All groups were sacrificed after a week; biopsies were taken from the implanted skins of all mice and Formalin-Fixed, Paraffin-Embedded (FFPE) blocks were prepared and stained with Hematoxylin and eosin stain (H&E). Each biopsy was analyzed in an absolutely blinded manner by a derma-pathologist and was evaluated by the use of five criteria; (1) the epidermal thickness, (2) the uniform shape of the epidermis, (3) the magnitude of the parakeratosis (the retention of nuclei in the stratum corneum), (4) the presence of neutrophils in the dermis and epidermis, and (5) the number of blood vessels. The detailed results for each mouse are depicted in Table 2.

TABLE 2

| Mouse number | Treatment | The epidermis thickness | Uniform shape of the epidermis | Parakeratosis is a mode of keratinization characterized by the retention of nuclei in the stratum corneum | Neutrophils in the dermis and epidermis | Multiple blood vessels | Score summary |
|---|---|---|---|---|---|---|---|
| Mouse number within the Group | | (1-5) | No = 0 Half/ half = 1 Yes = 2 | No = 0 Yes = 1 | No = 0 Yea = 1 | No = 0 Half/ half = 1 Yes = 2 | |
| 1 | T cells | 5 | 1 | 1 | 1 | 2 | 10 |
| 2 | T cells | 5 | 2 | 1 | 0 | 1 | 9 |
| 3 | T cells | 5 | 1 | 1 | 1 | 1 | 9 |
| 1 | PBS | 2 | 1 | 0 | 1 | 0 | 4 |
| 2 | PBS | 1 | 2 | 0 | 1 | 0 | 4 |
| 3 | PBS | 1 | 2 | 0 | 0 | 0 | 3 |
| 4 | PBS | 2 | 2 | 0 | 0 | 1 | 5 |
| 1 | miR197 (1 week) | 2 | 1 | 1 | 0 | 1 | 5 |
| 2 | miR197 (1 week) | 3 | 1 | 1 | 0 | 1 | 6 |
| 3 | miR197 (1 week) | 2 | 2 | 1 | 1 | 0 | 6 |
| 4 | miR197 (1 week) | 4 | 1 | 1 | 0 | 2 | 8 |
| 5 | miR197 (1 week) | 3 | 0 | 0 | 0 | 2 | 5 |
| 6 | miR197 (1 week) | 2 | 1 | 0 | 0 | 0 | 3 |
| 7 | miR197 (1 week) | 4 | 0 | 1 | 0 | 2 | 7 |
| 1 | Scra (1 week) | 3 | 2 | 1 | 1 | 0 | 7 |
| 2 | Scra (1 week) | 3 | 2 | 1 | 1 | 1 | 8 |
| 3 | Scra (1 week) | 3 | 2 | 1 | 0 | 2 | 8 |
| 4 | Scra (1 week) | 5 | 1 | 1 | 1 | 1 | 9 |
| 5 | Scra (1 week) | 3 | 0 | 1 | 0 | 2 | 6 |

Figure 25:
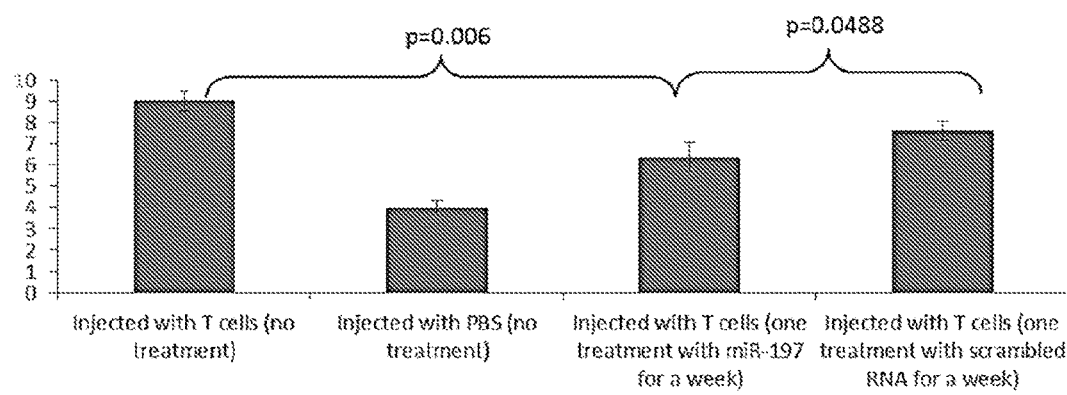
FIG. 25 presents the biological effects of miR-197 treatment on psoriasis lesions, summarizing the final score (as summarized in Table 2) in each of the experimental groups. It can be seen that miR-197 treatment improved markedly the psoriasis scoring of the skin, as the relative score became more similar to PBS treated normal skin tissue.

FIG. 25 summarizes the final score in each of the experimental groups. It can be seen that miR-197 treatment improved markedly the psoriasis scoring of the skin. The skin treated in Group 3, became similar to the results observed for normal skin treated with PBS of Group 2.

Summary of Examples 12-14

1) miR-197 regulates the signaling of IL-17, through targeting one of the IL17 receptor (IL17RA) subunit of IL-17 receptor. Thus miR-197 regulates the signaling of two cytokines: IL-22 and IL-17, which both play major role in the pathogenesis of psoriasis.

2) miR-197 could be applied topically on the psoriatic lesion with very efficient penetration efficiency.

3) Once penetration of the miR-197 to the epidermis was achieved, it is biochemically active, as it down-regulated the expression of its biochemical target, IL22RA1.

4) miR-197 could be detected in the implanted skin at least one week after applying it on the skin.

5) miR-197 treatment of human psoriatic skin in the mouse model improved markedly the psoriasis scoring of the skin.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method of treating an inflammatory skin disease, condition or lesion in a human subject, comprising the step of administering to the subject a therapeutically effective amount of a composition comprising, as the only active ingredient, at least one sequence selected from mature miR-197 [SEQ ID NO: 8], mature miR-99a [SEQ ID NO: 17], or a combination thereof, and, optionally, at least one additional sequence selected from the group consisting of pre-miR-197 [SEQ ID NO: 9], pre-miR-99a [SEQ ID NO: 16], pre-miR-Let7c [SEQ ID NO: 12], mature miR-Let7c [SEQ ID NO: 13], pre-miR-125b-2 [SEQ ID NO: 14], mature miR-125b-2 [SEQ ID NO: 15], or any combination thereof.

2. The method of claim 1, wherein said method reduces at least one symptom of the inflammatory skin disease, condition or lesion in the human subject.

3. The method of claim 1, wherein said method reduces or inhibits keratinocyte proliferation in the human subject.

4. The method of claim 1, wherein the composition comprises mature miR-197 [SEQ ID NO: 8] and mature miR-99a [SE ID NO: 17] as the only active ingredients.

5. The method of claim 1, wherein the inflammatory skin disease, condition or lesion is psoriasis.

6. The method of claim 5, wherein said psoriasis comprises plaque psoriasis, guttate psoriasis, inverse psoriasis, pustular psoriasis, erythrodermic psoriasis, or any combination thereof.

7. The method of claim 5, wherein the psoriasis is mild, moderate or severe.

8. The method of claim 2, wherein the at least one symptom comprises scaly patches on the skin, itchy skin, burning skin, stinging skin or pain, abnormal scar formation, abnormal pigmentation, skin creases, sun exposure damage or any combination thereof.

9. The method of claim 1, wherein the inflammatory skin disease, condition or lesion is present at least on an outside surface of skin.

10. The method of claim 9, wherein the surface of skin is on an elbow, knee, hand, finger, leg, foot, face, nail, genital or scalp, or any combination thereof.

11. The method of claim 1, wherein the treating reduces the number of lesions, reduces the size of the lesions, reduces the spread of a lesion, increases healing of a lesions, reduces the depth of the lesions, or promotes wound healing, or any combination thereof.

12. The method of claim 1, wherein the administration is topical administration.

13. The method of claim 12, wherein the topical administration comprises use of a cream, gel, ointment, spray, lip-balm, balm, emulsion, liposome, liquid crystal preparation or lotion, or any combination thereof.

14. The method of claim 1, wherein the administration comprises an at least a once a day administration for at least one day, an at least a twice a day administration for at least one day, an at least a once a day administration for at least one week, an at least a twice a day administration for at least one week, comprises an at least a once a day administration for at least one month, or an at least a twice a day administration for at least one month, or any combination thereof.

15. The method of claim 3, wherein said reducing or inhibiting keratinocyte proliferation treats, reduces the severity of, reduces the incidence or, delays the onset of, or reduces the pathogenesis of at least one symptom of an inflammatory skin disease.

16. The method of claim 3, wherein the reducing or inhibiting keratinocyte proliferation reduces the number of lesions, reduces the size of the lesions, reduces the spread of a lesion, increases healing of a lesion, reduces the depth of the lesions, or promotes wound healing in an inflammatory skin disease or any combination thereof.

17. The method of claim 12, further comprising a step of sonicating the skin comprising the lesion, condition, or disease, prior to the step of administration of said composition.

18. The method of claim 5, wherein said composition comprises mature miR-197 [SEQ ID NO: 8] as the only active ingredient.

19. The method of claim 18, wherein said composition is administered topically on the lesion.

* * * * *